US011352658B2

(12) United States Patent
Landegren et al.

(10) Patent No.: US 11,352,658 B2
(45) Date of Patent: Jun. 7, 2022

(54) METHOD FOR SELECTING A TARGET NUCLEIC ACID SEQUENCE

(71) Applicant: Olink Bioscience AB, Uppsala (SE)

(72) Inventors: Ulf Landegren, Uppsala (SE); Rachel Yuan Nong, Uppsala (SE)

(73) Assignee: NAVINCI DIAGNOSTICS AB, Uppsala (SE)

(*) Notice: Subject to any disclaimer, the term of this patent is extended or adjusted under 35 U.S.C. 154(b) by 676 days.

(21) Appl. No.: 15/500,418

(22) PCT Filed: Jul. 31, 2015

(86) PCT No.: PCT/EP2015/067725
§ 371 (c)(1),
(2) Date: Jan. 30, 2017

(87) PCT Pub. No.: WO2016/016452
PCT Pub. Date: Feb. 4, 2016

(65) Prior Publication Data
US 2018/0327818 A1 Nov. 15, 2018

(30) Foreign Application Priority Data
Aug. 1, 2014 (GB) .................................. 1413718

(51) Int. Cl.
*C12Q 1/68* (2018.01)
*C12P 19/34* (2006.01)
*C12N 9/00* (2006.01)
*C07H 21/04* (2006.01)
*C12Q 1/6813* (2018.01)
*C12Q 1/6844* (2018.01)

(52) U.S. Cl.
CPC ......... *C12Q 1/6813* (2013.01); *C12Q 1/6844* (2013.01)

(58) Field of Classification Search
None
See application file for complete search history.

(56) References Cited

U.S. PATENT DOCUMENTS

| 6,444,661 B1* | 9/2002 | Barton .................. C07F 15/008 514/185 |
| 6,558,928 B1 | 5/2003 | Landegren |
| 6,858,412 B2 | 2/2005 | Willis et al. |
| 6,867,028 B2 | 3/2005 | Janulaitis et al. |
| 7,883,849 B1 | 2/2011 | Dahl |
| RE44,265 E | 6/2013 | Landegren et al. |
| 8,518,640 B2 | 8/2013 | Drmanac et al. |
| 9,273,349 B2* | 3/2016 | Nguyen ............... C12Q 1/6816 |
| 2002/0065609 A1* | 5/2002 | Ashby .................. C12Q 1/6809 702/20 |
| 2002/0119455 A1* | 8/2002 | Chan .................... C12Q 1/6809 435/6.12 |
| 2003/0022167 A1 | 1/2003 | Alsmadi et al. |
| 2006/0166245 A1 | 7/2006 | Potter et al. |
| 2006/0286570 A1* | 12/2006 | Rowlen ................ C12Q 1/6816 435/6.12 |
| 2007/0009954 A1* | 1/2007 | Wang .................... C12Q 1/6823 435/6.12 |
| 2007/0031829 A1* | 2/2007 | Yasuno ................. C12Q 1/6886 435/6.12 |
| 2007/0042400 A1* | 2/2007 | Choi ...................... C12N 15/10 435/6.12 |
| 2007/0042419 A1* | 2/2007 | Barany ................. C12Q 1/6813 435/6.12 |
| 2007/0248965 A1 | 10/2007 | Carstens et al. |
| 2009/0011943 A1* | 1/2009 | Drmanac .............. C12N 15/64 506/4 |
| 2012/0014977 A1* | 1/2012 | Furihata ............. C07K 14/4748 424/185.1 |

(Continued)

FOREIGN PATENT DOCUMENTS

| WO | 03/012119 A2 | 2/2003 |
| WO | 03/044229 A1 | 5/2003 |
| WO | 2005/108608 A1 | 11/2005 |

(Continued)

OTHER PUBLICATIONS

"Archaea," Wikipedia.com, accessed May 11, 2016. (Year: 2018).*
"Oligonucleotide definition," Merriam-Webster.com; accessed Aug. 23, 2017. (Year: 2017).*
"Oligonucleotide", Wikipedia.com, accessed Feb. 17, 2019. (Year: 2019).*
"Viruses", Wikipedia.com, accessed Nov. 24, 2012. (Year: 2012).*
"How many species of bacteria are there", Wisegeek.com; accessed Jan. 21, 2014. (Year: 2014).*
"Fungi," Wikipedia.com; accessed Jun. 3, 2013. (Year: 2013).*
"Plant," Wikipedia.com; accessed Aug. 28, 2015. (Year: 2015).*
"Mammal," Wikipedia.com; accessed Sep. 22, 2011. (Year: 2011).*

(Continued)

*Primary Examiner* — Bradley L. Sisson
(74) *Attorney, Agent, or Firm* — Porter Wright Morris & Arthur LLP

(57) ABSTRACT

The present invention relates to a method for selecting a target region of interest (ROI) in a target nucleic acid molecule using a nucleic acid probe comprising a 3' sequence capable of hybridising to a target nucleic acid molecule and acting as a primer for the production of a complement of the target ROI (i.e. by target templated extension of the primer), and a sequence capable of templating the circularisation and ligation of the extended probe comprising the reverse complement of the target ROI and a portion of the probe. The circularised molecule thus obtained contains the reverse complement of the target ROI and may be subjected to further analysis and/or amplification etc. The probe may be provided as an oligonucleotide comprising a stem-loop structure or as a partially double-stranded construct and comprises a single-stranded 3' end region containing the target-binding site. A second binding site provided in the probe serves as the ligation template for circularisation, and the stem-loop structure, if present, is cleaved to render the second binding site available for (Continued)

Figure 1A:
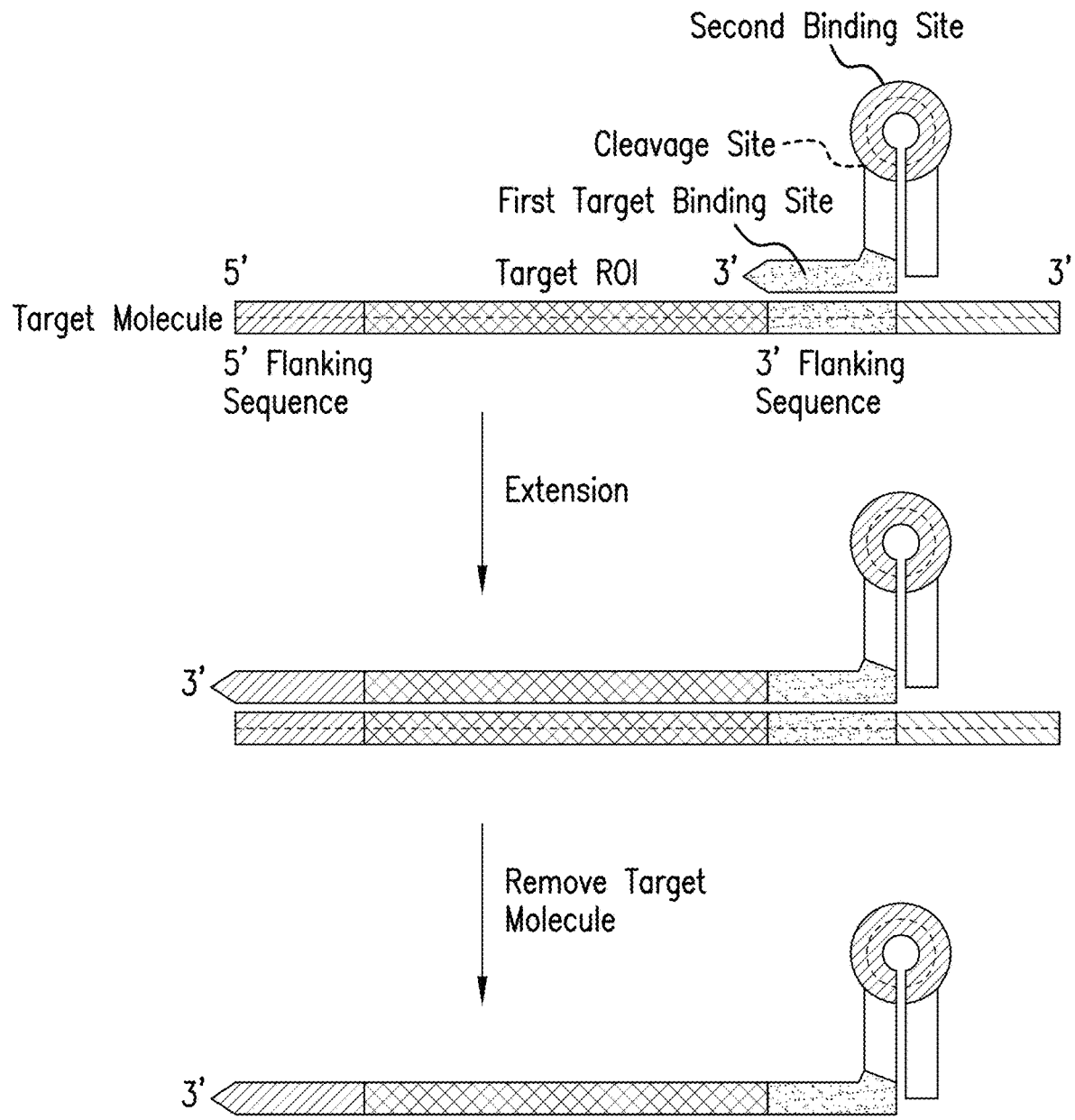

hybridisation to the target complement. Also provided are probes and kits for carrying out such a method.

52 Claims, 17 Drawing Sheets

Specification includes a Sequence Listing.

(56) References Cited

U.S. PATENT DOCUMENTS

| | | | | |
|---|---|---|---|---|
| 2012/0165219 | A1* | 6/2012 | Van Der Zaag | C12Q 1/6834 506/9 |
| 2012/0231972 | A1* | 9/2012 | Golyshin | C12Q 1/00 506/11 |
| 2012/0252012 | A1* | 10/2012 | Armougom | C12Q 1/689 435/6.11 |
| 2012/0253689 | A1* | 10/2012 | Rogan | G16B 30/00 702/20 |
| 2013/0177915 | A1 | 7/2013 | Too et al. | |
| 2013/0225623 | A1* | 8/2013 | Buxbaum | A61K 31/44 514/277 |
| 2014/0170654 | A1 | 6/2014 | Landegren et al. | |
| 2018/0057868 | A1* | 3/2018 | Walder | C12Q 1/6869 |
| 2019/0002971 | A1* | 1/2019 | Koslover | G01N 33/48 |

FOREIGN PATENT DOCUMENTS

| | | |
|---|---|---|
| WO | 2007/018601 A1 | 2/2007 |
| WO | 2011/067378 A1 | 6/2011 |
| WO | 2011/161549 A3 | 12/2011 |
| WO | 2012/152942 A1 | 11/2012 |
| WO | 2014/076209 A1 | 5/2014 |
| WO | 2014/076214 A1 | 5/2014 |
| WO | 2015/071445 A1 | 5/2015 |

OTHER PUBLICATIONS

"Murinae," Wikipedia.com, accessed Mar. 18, 2013. (Year: 2013).*
"Fish," Wikipedia.com, accessed Nov. 2, 2014. (Year: 2014).*
"Archaea," Wikipedia.com, accessed May 11, 2016. (Year: 2016).*
"Algae," Wikipedia.com, accessed Mar. 4, 2016. (Year: 2016).*
"Protozoa," Wikipedia.com, accessed May 11, 2016. (Year: 2016).*
Zhang etal., Bioinformatics, vol. 19, No. 1, 2003, pp. 14-21. (Year: 2003).*
"List of sequenced bacterial genomes", Wikipedia.com; accessed Jan. 24, 2014. (Year: 2014).*
Sommer and Tautz, "Minimal homology requirements for PCR primers", Nucleic Acids Research, vol. 17, No. 16, 1989, p. 6749. (Year: 1989).*
Forster et al., "A human gut bacterial genome and culture collection for improved metagenomic analyses" Nature Biotechnology, vol. 37, Feb. 2019, pp. 186-192. (Year: 2019).*
Drmanac et al., Human Genome Sequencing Using Unchained Base Reads on Self-Assembling DNA Nanoarrays, Science, 327:78-81 (Jan. 1, 2010).
Fredriksson et al., Multiplex amplification of all coding sequences within 10 cancer genes by Gene-Collector, Nucleic Acids Research, 35(7):1-6 (published online Feb. 22, 2007).
Dr. H. C. Kolb et al., Click Chemistry: Diverse Chemical Function from a Few Good Reactions, Angew. Chem. Int. Ed., 40:2004-2021 (2001).
Ali, M. Monsur et al., Rolling circle amplification: a versatile tool for chemical biology, materials science and medicine, Chem. Soc Rev. vol. 43, pp. 3324-3341 (2014).
Official Action from corresponding Chinese Application No. 201580053894.3 dated Jun. 3, 2020, with English Translation.
Official Action from corresponding Chinese Application No. 201580053894.3 dated Oct. 28, 2020, with English Translation.

* cited by examiner

Positive Sample

Sequenced PCR Product   NCAAGGCACTCTTGCCTACGCCACCAGCTCCAACTACCACCAAGTTTATATTCAGTCATTT
Expected PCR Product    -CAAGGCACTCTTGCCTACGCCACCAGCTCCAACTACCACCAAGTTTATATTCAGTCATTT
                         ************************************************************

Sequenced PCR Product   TCAGCAGGCACNGCACAAGCACGGAATTGTTGGANCATATATTCGTCCACAAAATGATTCTG
Expected PCR Product    TCAGCAGGCACTGCACAAGCACGGAATTGTTGGATCATATATTCGTCCACAAAATGATTCTG
                         *********,************ ********************************

Sequenced PCR Product   AATTAGCTGTATCGTCAAGGCACGA 145
Expected PCR Product    AATTAGCTGTATCGTCAAGGCACG- 143
                         ************************

—phi29

Sequenced PCR Product   NCAAGGCACTCTTGCCTACGCCACCAGCTCCAACTACCACNNGTTTATATTCAGTCNTTT
Expected PCR Product    -CAAGGCACTCTTGCCTACGCCACCAGCTCCAACTACCACCAAGTTTATATTCAGTCATTT
                         **************************************  * ***************

Sequenced PCR Product   TCAGCAGGCACTGCACAAGCACGGAATTGTTGGANCATATATTCGTCCNCNNAANGATTCTG
Expected PCR Product    TCAGCAGGCACTGCACAAGCACGGAATTGTTGGATCATATATTCGTCCACAAAATGATTCTG
                         ********************************.********* * ..****

Sequenced PCR Product   AATTAGCTGTATCGTCAAGGCACGA 145
Expected PCR Product    AATTAGCTGTATCGTCAAGGCACG- 143
                         ************************

FIG.7C

Cell Line: BJhTERT (40x Object)
Target: hTERT mRNA
Color Code:
Specific Signal = Target Specific Label + Probe Label All Mix No Extension No Cutting (AluI)

+microRNA

−microRNA

Detection 1:1000

SEQUENCE LISTING

<160> NUMBER OF SEQ ID NOS: 16

<210> SEQ ID NO 1
<211> LENGTH: 119
<212> TYPE: DNA
<213> ORGANISM: Artificial Sequence
<220> FEATURE:
<223> OTHER INFORMATION: ExCirc_1

<400> SEQUENCE: 1
cattattttt attataaggc ctggcgcatg cgtcctcctg ctgaaaatga ctgggggac      60 tcgaaaacga gtcccccccag gacgcatgcg ccctctattg ttggatcata ttcgtccac    119

<210> SEQ ID NO 2
<211> LENGTH: 106
<212> TYPE: DNA
<213> ORGANISM: Artificial Sequence
<220> FEATURE:
<223> OTHER INFORMATION: ExCirc_2

<400> SEQUENCE: 2
gtcacatttt cattattttt attataaggc ctgcgtgctt gtgcagtgcc tgctgaaaat    60
gaccaggcac tgcacaagca cggaattgtt ggatcatatt cgtcca                    106

<210> SEQ ID NO 3
<211> LENGTH: 140
<212> TYPE: DNA
<213> ORGANISM: Homo sapiens

<400> SEQUENCE: 3
cattattttt attataaggc ctgctgaaaa tgactgaata taaacttgtg gtagttggag    60
ctggtggcgt aggcaagagt gccttgacga tacagctaat tcagaatcat tttgtggacg    120
aatatgatcc aacaatagag                                                 140

<210> SEQ ID NO 4
<211> LENGTH: 150
<212> TYPE: DNA
<213> ORGANISM: Homo sapiens

<400> SEQUENCE: 4
gtcacatttt cattattttt attataaggc ctgctgaaaa tgactgaata taaacttgtg    60
gtagttggag ctggtggcgt aggcaagagt gccttgacga tacagctaat tcagaatcat    120
tttgtggacg aatatgatcc aacaatagag                                      150

<210> SEQ ID NO 5
<211> LENGTH: 22
<212> TYPE: DNA
<213> ORGANISM: Artificial Sequence
<220> FEATURE:
<223> OTHER INFORMATION: CLR_KRAS_1

<400> SEQUENCE: 5
cgtgccttga cgatacagct aa                                              22

<210> SEQ ID NO 6
<211> LENGTH: 19
<212> TYPE: DNA
<213> ORGANISM: Artificial Sequence
<220> FEATURE:
<223> OTHER INFORMATION: CLR_KRAS_2

<400> SEQUENCE: 6
caaggcactc ttgcctacg                                              19

<210> SEQ ID NO 7
<211> LENGTH: 149
<212> TYPE: DNA
<213> ORGANISM: Artificial Sequence
<220> FEATURE:
<223> OTHER INFORMATION: ExCirc_hTERT

<400> SEQUENCE: 7
tacggcgaca tggagaacaa gctgtttttt tttttttttt tttttttcgt gcttgtgcag    60
tgctgtttgc gggattaca gcactgcaca agcacggaag agtgaatgcg agtccgtctc   120
aacaagaaat catccaccaa acgcaggag                                    149

<210> SEQ ID NO 8
<211> LENGTH: 72
<212> TYPE: DNA
<213> ORGANISM: Homo sapiens

<400> SEQUENCE: 8
tacggcgaca tggagaacaa gctgtttgcg gggattcggc gggacgggct gctcctgcgt    60
ttggtggatg at                                                       72

<210> SEQ ID NO 9
<211> LENGTH: 15
<212> TYPE: DNA
<213> ORGANISM: Artificial Sequence
<220> FEATURE:
<223> OTHER INFORMATION: ExCirc_hTERT_Detection1
<220> FEATURE:
<221> NAME/KEY: misc_feature
<222> LOCATION: (1)..(1)
<223> OTHER INFORMATION: Cy3

<400> SEQUENCE: 9
cagcccgtcc cgccg                                                   15

<210> SEQ ID NO 10
<211> LENGTH: 16
<212> TYPE: DNA
<213> ORGANISM: Artificial Sequence
<220> FEATURE:
<223> OTHER INFORMATION: ExCirc_hTERT_Detection2
<220> FEATURE:
<221> NAME/KEY: misc_feature
<222> LOCATION: (1)..(1)
<223> OTHER INFORMATION: Cy5

<400> SEQUENCE: 10
tgcgagtccg tctuuu                                                  16

<210> SEQ ID NO 11
<211> LENGTH: 118
<212> TYPE: DNA
<213> ORGANISM: Artificial Sequence
<220> FEATURE:
<223> OTHER INFORMATION: ExCirc_miR208b

<400> SEQUENCE: 11
tttttttttt tttttttttt tctctctctc agctcactgg cagtgataag acgaattatc    60
actgccagtg agctagactt attgcggagt gaatgcgagt ccgtctacaa accttttg    118

<210> SEQ ID NO 12
<211> LENGTH: 22
<212> TYPE: RNA
<213> ORGANISM: Artificial Sequence
<220> FEATURE:
<223> OTHER INFORMATION: Synthetic_RNA_miR208b

<400> SEQUENCE: 12
auaagacgaa caaaagguuu gu                                              22

<210> SEQ ID NO 13
<211> LENGTH: 20
<212> TYPE: DNA
<213> ORGANISM: Artificial Sequence
<220> FEATURE:
<223> OTHER INFORMATION: ExCirc_miR208b_Detection
<220> FEATURE:
<221> NAME/KEY: misc_feature
<222> LOCATION: (1)..(1)
<223> OTHER INFORMATION: Cy3

<400> SEQUENCE: 13
cagtgaatgc gagtccgtct                                                 20

<210> SEQ ID NO 14
<211> LENGTH: 145
<212> TYPE: DNA
<213> ORGANISM: Artificial Sequence
<220> FEATURE:
<223> OTHER INFORMATION: PCR Product
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t

<400> SEQUENCE: 14
ncaaggcact cttgcctacg ccaccagctc caactaccac aagtttatat tcagtcatttt     60 tcagcaggca cngcacaagc acggaattgt tggancatat tcgtccacaa aatgattctg    120
aattagctgt atcgtcaagg cacga                                          145

<210> SEQ ID NO 15
<211> LENGTH: 143
<212> TYPE: DNA
<213> ORGANISM: Artificial Sequence
<220> FEATURE:
<223> OTHER INFORMATION: Reference sequence

<400> SEQUENCE: 15
caaggcactc ttgcctacgc caccagctcc aactaccaca gtttatatt cagtcatttt      60 cagcaggcac tgcacaagca cggaattgtt ggatcatatt cgtccacaaa atgattctga    120
attagctgta tcgtcaaggc acg                                            143

<210> SEQ ID NO 16
<211> LENGTH: 145
<212> TYPE: DNA
<213> ORGANISM: Artificial Sequence
<220> FEATURE:
<223> OTHER INFORMATION: PCR Product

```
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (109)..(110)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t

<400> SEQUENCE: 16
ncaaggcact cttgcctacg ccaccagctc caactaccac nngtttatat tcagtcnttt      60
tcagcaggca ctgcacaagc acggaattgt tggancatat tcgtccncnn aangattctg    120
aattagctgt atcgtcaagg cacga                                          145
```

METHOD FOR SELECTING A TARGET NUCLEIC ACID SEQUENCE

The Sequence Listing submitted herewith, entitled "121033-02-seq-list_st25.txt", created Jan. 30, 2017 and having a size of 5328 bytes, is incorporated herein by reference.

The present invention relates to a method for selecting a target nucleic acid sequence. In particular, the present invention relates to a method of selecting a target region of interest (ROI) in a target nucleic acid molecule using a particular nucleic acid probe comprising a 3' sequence capable of hybridising to a target nucleic acid molecule and acting as a primer for the production of a complement of the target ROI (i.e. by target templated extension of the primer), and an internal sequence capable of templating the circularisation and ligation of the extended probe comprising the reverse complement of the target ROI and a portion of the probe. The circularised molecule thus obtained contains the reverse complement of the target ROI and may be subjected to further analysis and/or amplification etc. The selection method of the invention thus provides a method not only for selectively isolating or separating a desired target sequence (ROI), but also for detecting a target nucleic acid sequence (ROI), or for amplifying a target sequence (ROI).

There are several methods described for selection and subsequent amplification of selected parts of a nucleic acid. Examples include so-called selector probes (U.S. Pat. No. 7,883,849, or general circularisation of genomic fragments as described in Drmanac et al 2010. Science, 327, 78-81 and U.S. Pat. No. 8,518,640).

Selector probes as described in U.S. Pat. No. 7,883,849 are designed to bind in a sequence-specific manner to a desired target sequence hence allowing it to be "selected" from a nucleic acid molecule, or indeed from a sample containing nucleic acid molecules. In the method of U.S. Pat. No. 7,883,849 partially double-stranded selector probes (either a single symmetrical molecule in which the longer strand overhangs at both ends, or two asymmetrical molecules each having a single-stranded overhang at only one end) are hybridised via their single-stranded overhangs in a target-specific manner to both ends of single-stranded (denatured) target fragments resulting from fragmentation of the nucleic acid sample. In a particular embodiment of the method using the symmetrical selector probe, only one end of the target fragment hybridises to an end of the selector probe, the other end of the selector probe hybridising internally of the target nucleic acid fragment and requiring a structure-specific endonuclease to resolve the resulting structure by cleaving off the portion of the target fragment protruding beyond the internal hybridised region. In all cases, therefore, the selected portion of the target fragment is delineated by the regions (whether both end regions or one end and one internal region) of known sequence to which the selector probe(s) has been designed to hybridise. Following hybridisation (and, where appropriate, resolution of the secondary structure) the selector(s) and target nucleic acid fragment are joined by ligation to give (i) in the case of the symmetrical selector probe, a circular nucleic acid molecule and (ii) in the case of the two asymmetrical selectors a linear molecule comprising the target fragment flanked by selector probe sequences. The double-stranded region of the selector probe(s) contains a primer pair motif which is common to the plurality of different target-specific selectors used in a multiplex assay. Hence, amplification of multiple target fragments can be achieved simultaneously whilst avoiding amplification artefacts which can result from the use of multiple, different primer pairs.

A particular problem identified in the selection methods of U.S. Pat. No. 7,883,849 is the requirement to carefully select which restriction enzymes are used to digest a target nucleic acid molecule prior to selection, in order to avoid selecting enzymes which can cleave a target nucleic acid molecule within the target sequence to be interrogated. This places limits on the degree of multiplexing that is possible according to this method, and can lead to the amplification of unduly long nucleic acid fragments, thereby increasing the cost of analysing the target nucleic acids selected.

In contrast to methods disclosed in the prior art, the present invention does not require the prior cleavage of a sample nucleic acid prior to selection (although this is not precluded), and in particular it does not require cleavage in a manner to create specific binding sites for the probe in the target molecule. Instead, it directs the production of a complement of a specific region of a single-stranded target nucleic acid molecule (via target templated extension of the probe) and, following cleavage of the probe and optionally cleavage of the target, templates the circularisation of the resulting complement of the target nucleic acid molecule. Thus, the present invention may be seen to minimise the need for the precise selection of restriction enzymes to be used and, in some embodiments, circumvent the need for the precise selection of restriction enzymes to be used. Thus the present invention provides an improved method for the selection of target nucleic acid molecules, and allows for the more precise selection of which sequences are to be interrogated or analysed, e.g. by sequencing, but without requiring target nucleic acid molecules containing specific probe binding sites at their ends.

The invention accordingly provides a new kind of probe for selecting a desired or target nucleic acid sequence, which provides a new way of generating a circular molecule containing the target sequence (more particularly, a complement of the target sequence). Circular molecules may readily be separated and handled (e.g. by digesting any linear non-circularised nucleic acid molecules using exonuclease enzymes) and may also be readily amplified and/or detected using rolling circle amplification (RCA) or other amplification procedures. They are thus a very convenient way of providing a selected target sequence for further handling or processing, or analysis or detection etc.

The new probe for use according to the invention is a single stranded nucleic acid molecule (i.e. an oligonucleotide) that is capable of forming a stem-loop structure with a single-stranded region at the 3' end. Thus the probe comprises a first target binding site at its 3' end capable of hybridising to a complementary binding site in the target molecule flanking the 3' end of the ROI, and a stem-loop structure comprising a second binding site which is homologous to a flanking sequence flanking the 5' end of the ROI and is capable of hybridising to a complement of said 5' flanking sequence, and also comprising a cleavage site 3' of the second binding site in the stem-loop structure such that cleavage allows the loop to open (e.g. a cleavage site in the stem or loop of the stem-loop structure). The first target binding site serves to produce a complement of the target ROI via target templated extension of the probe. The second binding site serves as a template for circularisation of the extended probe once the stem-loop structure has been opened by cleavage. Sequence elements (or spacer sequences or elements) can be placed between the first target binding site and the stem-loop structure, within the loop of the stem-loop structure (e.g. at the 5' end of the loop), or 5' of the stem-loop structure to enable or facilitate various downstream applications, e.g. elements serving as tag or detection or identification sequences or sequences for the capture (e.g. immobilisation) or amplification of the target sequence/ROI, e.g. detection or ID tags or motifs (e.g. barcodes etc.), binding sites for detection probes or primers or for amplification primers, or a capture (or "anchor") sequence able to bind to a complementary sequence or cognate binding partner, e.g. provided on a solid support. Such elements (or tags) may also be present within the stem sequence of the stem-loop structure, and thereby will be incorporated into the nucleic acid when it is circularised (e.g. when the element or tag is 3' of the cleavage site in the stem-loop structure).

After extension of the probe to produce the target complement comprising the ROI, the target molecule is removed, to leave the extended probe. Although this may be done in various ways, conveniently the probe/target hybrid may be denatured. It will be seen that in such an embodiment, the stem-loop structure serves to hold together various particular regions of the probe (specifically the second binding site in the loop) whilst the probe undergoes the steps of binding to the target molecule, extension and removal of the target molecule. However, in other embodiments the target molecule may be removed in other ways, for example by enzymatic digestion (e.g. using Rnase to remove a RNA target molecule) and in such an embodiment, a stem-loop structure is not essential and the probe may be cleaved prior to contact with the target molecule or alternatively it may be provided as a partially double-stranded construct. In such an embodiment, the target molecule may be removed in a manner which does not involve denaturation, and particularly which does not involve denaturation of the probe. Thus, the second binding site, present on a second strand of the probe, may remain in the probe.

The method of the invention allows the use of single stranded target molecules and target fragments without the need to know the end-sequence of the target. However, whilst the need to create fragments with target-specific ends is avoided and the method does not require a fragmentation step, it may be convenient and desirable to include an initial fragmentation step in the method.

It will be evident from the discussion of the invention below that a complement of the target molecule is circularised in the methods and probes of the invention. Accordingly, references to the circularised target sequence or target ROI etc., in the context of the invention will be understood to mean the complement of the target sequence or target ROI. Hence, the skilled person would understand from the context of the discussion herein that references to the detection, analysis etc. of the target sequence or target ROI encompasses the detection, analysis etc. of the complement thereof, wherein a detection probe may need to hybridise to the complement of the target sequence (e.g. where the captured or selected target fragment is analysed directly) or to the "original" target sequence (e.g. where the captured or selected sequence has been amplified, e.g. by RCA, such that the amplification product contains a complement of the captured complementary sequence). As double stranded nucleic acid molecules are antiparallel, a complementary sequence, when oriented 5' to 3', may be referred to as the reverse complement sequence and these terms may be used interchangeably herein.

At its broadest, the invention accordingly provides a method of selecting a target region of interest (ROI) in a target nucleic acid molecule, said ROI being flanked by a 3' flanking sequence and a 5' flanking sequence in the target molecule, said method comprising:

(a) providing a probe comprising
  (i) a first target-binding site at a 3' end region of said probe, which binding site is capable of hybridising to a complementary binding site in the target molecule, said complementary binding site being the 3' flanking sequence flanking the 3' end of the ROI, and is capable of being extended to generate a complement of the target molecule in a target-templated extension reaction, said target complement comprising the complement of said 3' flanking sequence and at least of the ROI and the 5' flanking sequence; and
  (ii) a second binding site which is homologous to the 5' flanking sequence flanking the 5' end of the ROI and is capable of hybridising to a complement of said 5' flanking sequence in said target complement;
    wherein said probe is provided as an oligonucleotide comprising a stem-loop structure which comprises the second binding site in the loop of the structure and further comprises a cleavage site 3' of the second binding site which is cleavable to open the loop to render the second binding site available for binding, and a single-stranded region at the 3' end comprising the first binding site; or
    wherein said probe is provided as a partially double-stranded construct comprising a first strand comprising a single-stranded 3' end region comprising the first binding site at the 3' end thereof and a second strand hybridised at the 5' end of said first strand and comprising a single-stranded 3' end region comprising the second binding site;
(b) contacting the probe with the target molecule and allowing the first target-binding site at the 3' end of the probe to hybridise to its complementary binding site in the target molecule, wherein the target molecule is at least partially single stranded including in the region comprising the complementary binding site, and optionally the ROI and the 5' flanking sequence;
(c) extending the hybridised 3' end of the probe using the target molecule as an extension template to generate a complement of the target molecule;
(d) removing the target molecule, leaving an extended probe comprising 3' to 5' in the extended region complements of the 5' flanking sequence, the ROI and the 3' flanking sequence of the target molecule, wherein the second binding site remains in the probe;
(e) allowing the extended probe to undergo an intramolecular rearrangement such that the second binding site hybridises to its complementary binding site in the target complement, being the complement of the 5' flanking sequence of the target molecule,
  wherein if said probe comprises a stem-loop structure the rearrangement comprises cleavage of the extended probe at the cleavage site in the stem-loop structure of the probe to release a 3' end of the probe comprising the second binding site thereby generating a partially double-stranded construct comprising a first extended strand comprising the target complement and a second strand hybridised to the first strand in the stem and comprising the released 3' end which is then able to hybridise to its complementary binding site in the first strand, and
  wherein if said 5' flanking sequence is internal to the 5' end of the target molecule and the target complement in the first extended strand contains an additional sequence 3' of the complement of the 5' flanking sequence, the rearrangement comprises a cleavage in or of the additional sequence to release the 3' end of the first strand comprising the complementary binding site for the second binding site, such that the, optionally released, 5' end of the first, extended, strand and the, optionally released, 3' end of the first, extended, strand are brought into juxtaposition for ligation directly or indirectly to each other, using the second binding site as ligation template;

(f) ligating the ends of the extended strand of the probe directly or indirectly to one another to circularise the extended strand of the probe;

(g) amplifying or separating the circularised extended strand, thereby to select the ROI.

However, in one preferred embodiment, the probe is provided as an oligonucleotide comprising a stem-loop structure.

Thus, in a particular first aspect the invention provides a method of selecting a target region of interest (ROI) in a target nucleic acid molecule, said method comprising;

(a) providing a probe comprising a stem-loop structure and a single-stranded region at the 3' end, wherein said 3' end region comprises a first target-binding site which is capable of hybridising to a complementary binding site in the target molecule, said complementary binding site being a flanking sequence flanking the 3' end of the ROI, and said loop comprises a second binding site which is homologous to a flanking sequence flanking the 5' end of the ROI and is capable of hybridising to a complement of said 5' flanking sequence, and wherein said stem-loop structure further comprises a cleavage site 3' of said second binding site such that cleavage allows the loop to open;

(b) contacting the probe with the target molecule and allowing the first target-binding site at the 3' end of the probe to hybridise to its complementary binding site in the target molecule, wherein the target molecule is at least partially single stranded including in the region comprising the complementary binding site, and optionally the ROI and the 5' flanking sequence;

(c) extending the hybridised 3' end of the probe using the target molecule as an extension template to generate a complement of the target molecule;

(d) removing the target molecule, leaving an extended probe comprising 3' to 5' in the extended region complements of the 5' flanking sequence, the ROI and the 3' flanking sequence of the target molecule;

(e) allowing the extended probe to undergo an intramolecular rearrangement such that the second binding site is able to hybridise to its complementary binding site in the target complement, being the complement of the 5' flanking sequence of the target molecule, wherein the rearrangement comprises cleavage of the extended probe at least at the cleavage site in the stem-loop structure of the probe to release a 3' end of the probe comprising the second binding site thereby generating a partially double-stranded construct comprising a first extended strand comprising the target complement and a second strand hybridised to the first strand in the stem and comprising the released 3' end which is then able to hybridise to its complementary binding site in the first strand, and if said 5' flanking sequence is internal to the 5' end of the target molecule and the target complement in the first extended strand contains an additional sequence 3' of the complement of the 5' flanking sequence, also a second cleavage in or of the additional sequence to release the 3' end of the first strand comprising the complementary binding site for the second binding site, such that the released 5' end of the first, extended, strand and the optionally released 3' end of the first, extended, strand are brought into juxtaposition for ligation directly or indirectly to each other, using the second binding site as ligation template;

(f) ligating the ends of the extended strand of the probe directly or indirectly to one another to circularise the extended strand of the probe;

(g) amplifying or separating the circularised extended strand, thereby to select the ROI.

In a further aspect there is provided a probe for use in the method of the invention. More particularly, in this further aspect the invention provides an oligonucleotide probe for selecting a target ROI in a target nucleic acid molecule, said probe comprising a stem-loop structure and a single-stranded region at the 3' end, wherein said 3' end region comprises a first target-binding site which is capable of hybridising to a complementary binding site in the target molecule, said complementary binding site being a flanking sequence flanking the 3' end of the ROI, and said loop comprises a second binding site which is homologous to a flanking sequence flanking the 5' end of the ROI and is capable of hybridising to a complement of said 5' flanking sequence, and wherein said stem-loop structure further comprises a cleavage site 3' of said second binding site such that cleavage allows the loop to open.

In an alternative embodiment, the probe is provided as a partially double-stranded construct.

Thus, in a second particular aspect, the invention provides a method of selecting a target region of interest (ROI) in a target nucleic acid molecule, said method comprising;

(a) providing a probe being a partially double-stranded construct having a first strand comprising single-stranded 3' end region comprising a first target-binding site at the 3' end thereof, wherein said first target binding site is capable of hybridising to a complementary binding site in the target molecule, said complementary binding site being a flanking sequence flanking the 3' end of the ROI, and a second strand hybridised to said first strand at the 5' end thereof and comprising a single-stranded 3' end region comprising a second binding site, wherein the second binding site is homologous to a flanking sequence flanking the 5' end of the ROI and is capable of hybridising to a complement of said 5' flanking sequence;

(b) contacting the probe with the target molecule and allowing the first target-binding site at the 3' end of the first strand of the probe to hybridise to its complementary binding site in the target molecule, wherein the target molecule is at least partially single stranded including in the region comprising the complementary binding site, and optionally the ROI and the 5' flanking sequence;

(c) extending the hybridised 3' end of the first strand of the probe using the target molecule as an extension template to generate a complement of the target molecule;

(d) removing the target molecule without denaturing the probe, leaving an extended probe comprising 3' to 5' in the extended region complements of the 5' flanking sequence, the ROI and the 3' flanking sequence of the target molecule;

(e) allowing the extended probe to undergo an intramolecular rearrangement such that the second binding site in the second strand is able to hybridise to its complementary binding site in the target complement in the extended first strand, being the complement of the 5' flanking sequence of the target molecule, wherein if said 5' flanking sequence is internal to the 5' end of the target molecule and the target complement in the first extended strand contains an additional sequence 3' of the complement of the 5' flanking sequence, the rearrangement comprises a cleavage in or of the additional sequence to release the 3' end of the first strand comprising the complementary binding site for the second binding site,
such that the 5' end of the first, extended, strand and the optionally released 3' end of the first, extended, strand are brought into juxtaposition for ligation directly or indirectly to each other, using the second binding site as ligation template;
(f) ligating the ends of the extended strand of the probe directly or indirectly to one another to circularise the extended strand of the probe;
(g) amplifying or separating the circularised extended strand, thereby to select the ROI.

In a further aspect there is provided a probe for use in the method of the invention. More particularly, in this further aspect the invention provides an oligonucleotide probe for selecting a target ROI in a target nucleic acid molecule, said probe being a partially double-stranded construct having a first strand comprising single-stranded 3' end region comprising a first target-binding site at the 3' end thereof, wherein said first target binding site is capable of hybridising to a complementary binding site in the target molecule, said complementary binding site being a flanking sequence flanking the 3' end of the ROI, and a second strand hybridised to said first strand at the 5' end thereof and comprising a single-stranded 3' end region comprising a second binding site, wherein the second binding site is homologous to a flanking sequence flanking the 5' end of the ROI and is capable of hybridising to a complement of said 5' flanking sequence.

It will be understood from the above that the probe does not need to comprise a sequence which is capable of hybridising to the ROI or its complement, i.e. the first-target binding site comprises a sequence which is capable of hybridising to the sequence flanking the 3' of the ROI. Nevertheless, in some embodiments the first-target binding site may also contain a sequence that is capable of hybridising to a portion of the 3' end of the ROI.

In further embodiments, however, the probe (either a partially double-stranded probe or stem-loop probe) may also contain a sequence complementary to (or capable of hybridising to) the complement of the ROI (i.e. homologous to the ROI), or a part thereof, which sequence is capable of hybridising to the complement of the ROI following extension of the probe. Said sequence may be homologous to the entire ROI, or may be homologous to a portion (i.e. the 5' part) of the ROI. Said sequence may form at least a part of the second binding site (or may form the second binding site) in the probe, and may thus act to template the circularisation of the extended probe following a step of extension and molecular. The sequence complementary to the ROI may be viewed as forming either all or a portion of the second binding site a partially double-stranded probe or stem-loop probe) according to certain particular methods of the present invention.

Figure 13:
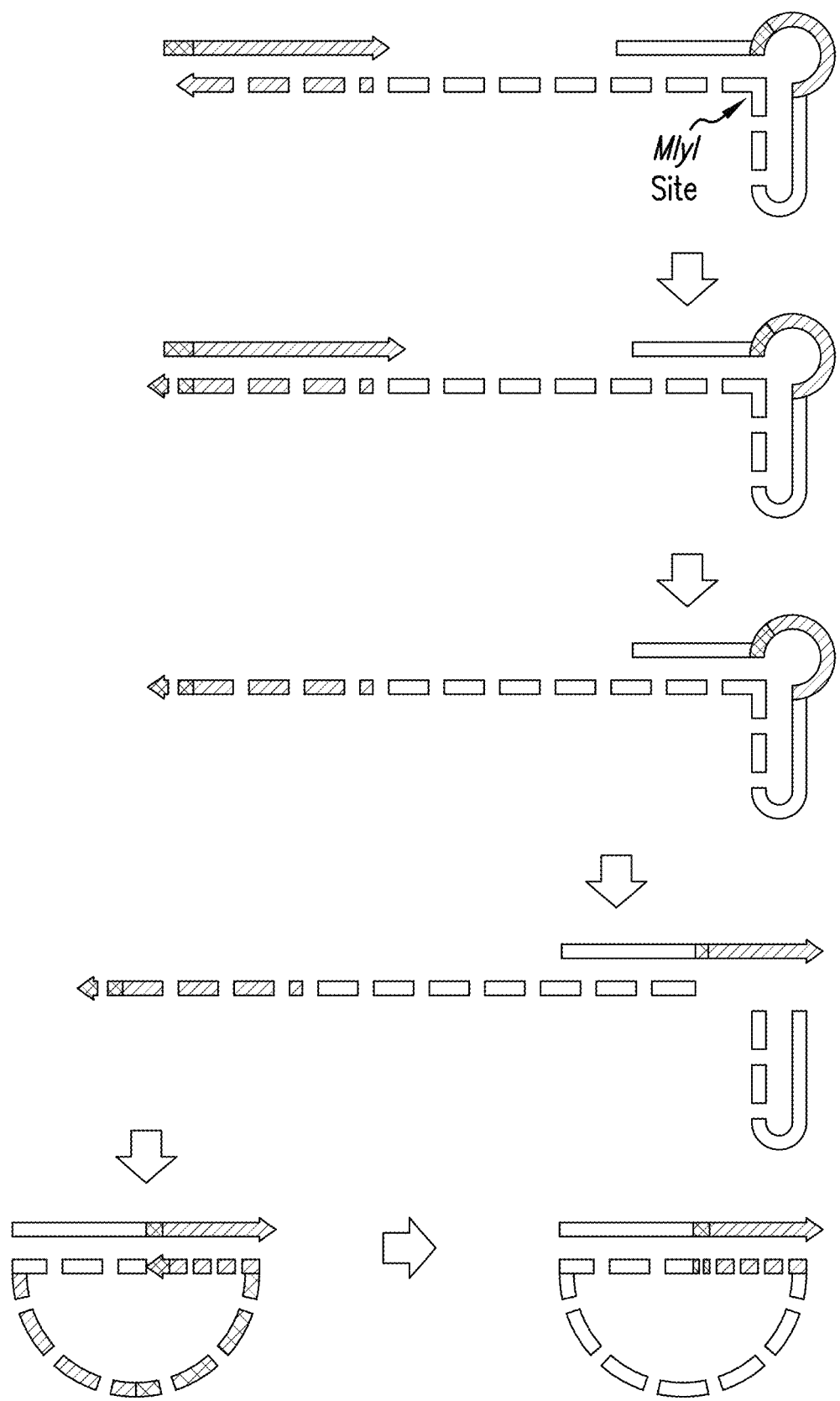

In another embodiment, the probe may further comprise a further probe sequence, lying 3' of the second binding site, which sequence is homologous to the 3' flanking sequence (in the target nucleic acid molecule) and thus complementary to the first binding site in the probe, wherein when said probe comprises a stem-loop structure said further probe sequence is located in the loop or when said probe is a double-stranded construct the further probe sequence is located at the 3' end of the second strand. In such an embodiment, the further probe sequence may hybridise to the first binding site and act as a ligation template together with the second binding site. FIG. 13 depicts such an arrangement.

Accordingly, looking at such embodiments of the invention in an alternative way, in an alternative aspect, the target nucleic acid molecule may alternatively be defined as comprising a region of interest and a 3' flanking region, wherein the probe is designed to hybridise to the complement of the 5' end of the region of interest (or the region of interest). In light of the above discussion, it will be seen that the ROI itself, or more particularly the 5' end thereof, functions as or comprises the 5' flanking region.

In a third particular aspect, the present invention thus provides a method of selecting a target region of interest (ROI) in a target nucleic acid molecule, said method comprising:
(a) providing a probe comprising
(i) a first target-binding site at a 3' end region of said probe, which binding site is capable of hybridising to a complementary binding site in the target molecule, said complementary binding site being a 3' flanking sequence flanking the 3' end of the ROI, and is capable of being extended to generate a complement of the target molecule in a target-templated extension reaction, said target complement comprising the complement of said 3' flanking sequence and the ROI; and
(ii) a second binding site which is homologous to the ROI, or to the 5' end thereof, and is capable of hybridising to a complement of the ROI, or of the 5' end thereof, in said target complement;
(iii) a further probe sequence, lying 3' of the second binding site, which is homologous to the 3' flanking sequence and complementary to the first binding site;
wherein said probe is provided as an oligonucleotide comprising a stem-loop structure which comprises the second binding site and the further probe sequence in the loop of the structure and further comprises a cleavage site 3' of the second binding site and further probe sequence, which is cleavable to open the loop to render the second binding site and further probe sequence available for binding, and a single-stranded region at the 3' end of the probe comprising the first binding site at the 3' end thereof; or
wherein said probe is provided as a partially double-stranded construct comprising a first strand comprising a single-stranded 3' end region comprising the first binding site at the 3' end thereof and a second strand hybridised at the 5' end of said first strand and comprising a single-stranded 3' end region comprising the second binding site and the further probe sequence at the 3' end of the single-stranded region;
(b) contacting the probe with the target molecule and allowing the first target-binding site at the 3' end of the probe to hybridise to its complementary binding site in the target molecule, wherein the target molecule is at least partially single stranded including in the region comprising the complementary binding site, and optionally the ROI;

(c) extending the hybridised 3' end of the probe using the target molecule as an extension template to generate a complement of the target molecule;
(d) removing the target molecule, leaving an extended probe comprising 3' to 5' in the extended region a complement of the ROI, and the 3' flanking sequence of the target molecule, wherein the second binding site remains in the probe;
(e) allowing the extended probe to undergo an intramolecular rearrangement such that the second binding site hybridises to its complementary binding site in the target complement, being the complement of the ROI, of the 5' end of the ROI, and the further probe sequence hybridises to the first binding site, wherein if said probe comprises a stem-loop structure the rearrangement comprises cleavage of the extended probe at the cleavage site in the stem-loop structure of the probe to release a 3' end of the probe comprising the second binding site and the further probe sequence, thereby generating a partially double-stranded construct comprising a first extended strand comprising the target complement and a released 5' end, and a second strand hybridised to the first strand in the stem and comprising the released 3' end which is then able to hybridise to its complementary binding sites in the first strand, and wherein if said ROI is internal to the 5' end of the target molecule and the target complement in the first extended strand contains an additional sequence 3' of the complement of the ROI, the rearrangement comprises a cleavage in or of the additional sequence to release the 3' end of the first strand comprising the complementary binding site for the second binding site, such that the, optionally released, 5' end of the first, extended, strand and the, optionally released, 3' end of the first, extended, strand are brought into juxtaposition for ligation directly or indirectly to each other, using the second binding site and further probe sequence as ligation template;

(f) ligating the ends of the extended strand of the probe directly or indirectly to one another to circularise the extended strand of the probe;
(g) amplifying or separating the circularised extended strand, thereby to select the ROI.

FIG. 13 can be seen to depict such a method.

In a more particular embodiment, the method comprises:
(a) providing a probe being a partially double-stranded construct having a first strand comprising single-stranded 3' end region comprising a first target-binding site at the 3' end thereof, wherein said first target binding site is capable of hybridising to a complementary binding site in the target molecule, said complementary binding site being a flanking sequence flanking the 3' end of the ROI, and a second strand hybridised to said first strand at the 5' end thereof and comprising a single-stranded 3' end region comprising a second binding site and 3' to the second binding site and at the 3' end of the single-stranded region a further probe sequence, wherein the second binding site is homologous to the ROI, or to the 5' end thereof, and is capable of hybridising to a complement of said ROI, or of the 5' end thereof, and said further probe sequence is homologous to the 3' flanking sequence and complementary to the first binding site;
(b) contacting the probe with the target molecule and allowing the first target-binding site at the 3' end of the first strand of the probe to hybridise to its complementary binding site in the target molecule, wherein the target molecule is at least partially single stranded including in the region comprising the complementary binding site, and optionally the ROI;
(c) extending the hybridised 3' end of the first strand of the probe using the target molecule as an extension template to generate a complement of the target molecule;
(d) removing the target molecule without denaturing the probe, leaving an extended probe comprising 3' to 5' in the extended region a complement of the ROI, and the 3' flanking sequence of the target molecule;
(e) allowing the second binding site and the further probe sequence in the second strand to hybridise to their complementary binding sites in the target complement in the extended first strand, thereby to bring the 5' and 3' ends of the first, extended, strand into juxtaposition for ligation, directly or indirectly to each other, using the second binding site and further probe sequence as ligation template, wherein if said ROI is internal to the 5' end of the target molecule and the target complement in the first extended strand contains an additional sequence 3' of the complement of the ROI, the rearrangement comprises a cleavage in or of the additional sequence to release the 3' end of the first strand comprising the complementary binding site for the second binding site;

(f) ligating the ends of the extended strand of the probe directly or indirectly to one another to circularise the extended strand of the probe;
(g) amplifying or separating the circularised extended strand, thereby to select the ROI.

In another embodiment, the method comprises:
(a) providing a probe comprising a stem-loop structure and a single-stranded region at the 3' end, wherein said 3' end region comprises a first target-binding site which is capable of hybridising to a complementary binding site in the target molecule, said complementary binding site being a 3' flanking sequence flanking the 3' end of the ROI, and said loop comprises a second binding site which is homologous to the ROI, or to the 5' end thereof, and is capable of hybridising to a complement of the ROI, or of the 5' end thereof, and, 3' to the second binding site, a further probe sequence which is homologous to the 3' flanking sequence and complementary to the first binding site, and wherein said stem-loop structure further comprises a cleavage site 3' of the second binding site and further probe sequence such that cleavage allows the loop to open;
(b) contacting the probe with the target molecule and allowing the first target-binding site at the 3' end of the probe to hybridise to its complementary binding site in the target molecule, wherein the target molecule is at least partially single stranded including in the region comprising the complementary binding site, and optionally the ROI;
(c) extending the hybridised 3' end of the probe using the target molecule as an extension template to generate a complement of the target molecule;
(d) removing the target molecule, leaving an extended probe comprising 3' to 5' in the extended region a complement of the ROI, and the 3' flanking sequence of the target molecule, wherein the second binding site remains in the probe;
(e) allowing the extended probe to undergo an intramolecular rearrangement such that the second binding site hybridises to the complement of the ROI, or to the 5' end thereof, and the further probe sequence hybridises to the first binding site, wherein the rearrangement comprises cleavage of the extended probe at the cleavage site in the stem-loop structure of the probe to release a 3' end of the probe comprising the second binding site and the further probe sequence, thereby generating a partially double-stranded construct comprising a first extended strand comprising the target complement and a released 5' end, and a second strand hybridised to the first strand in the stem and comprising the released 3' end which is then able to hybridise to its complementary binding sites in the first strand, such that the released 5' end of the first, extended, strand and the, optionally released, 3' end of the first, extended, strand are brought into juxtaposition for ligation directly or indirectly to each other, using the second binding site and further probe sequence as ligation template;

(f) ligating the ends of the extended strand of the probe directly or indirectly to one another to circularise the extended strand of the probe;

(g) amplifying or separating the circularised extended strand, thereby to select the ROI.

In the aspects of the invention in which the probe comprises a sequence homologous to the ROI, the ROI may be situated at the 5' end of the target molecule, or may be situated internal to the 5' end of the target molecule. If the ROI is internal to the 5' end of the target molecule and the target complement in the first extended strand contains an additional sequence 3' of the complement of the ROI, the rearrangement comprises a cleavage in or of the additional sequence to release the 3' end of the first strand comprising the complementary binding site for the second binding site (i.e. the complement of the ROI).

However, in a particular aspect, the ROI may lie at the 5' end of the target nucleic acid molecule and step (e) comprises allowing the second binding site in the second strand to hybridise to its complementary binding site in the target complement in the extended first strand, thereby to bring the 5' and 3' ends of the first, extended, strand in juxtaposition for ligation, directly or indirectly to each other, using the second binding site as a ligation template.

Thus in one embodiment, the probe may be a partially double-stranded construct having a first strand comprising a single-stranded 3' end region comprising a first target-binding site at the 3' end thereof, wherein said first target binding site is capable of hybridising to a complementary binding site in the target molecule, said complementary binding site being a flanking sequence flanking the 3' end of the ROI, and a second strand hybridised to said first strand at the 5' end thereof and comprising a single-stranded 3' end region comprising a second binding site and 3' to the second binding site and at the 3' end of the single-stranded region a further probe sequence, wherein the second binding site is homologous to the 5' end of the ROI, or to the ROI, and is capable of hybridising to a complement of said ROI, or of the 5' end thereof and said further probe sequence is homologous to the 3' flanking sequence and complementary to the first binding site.

In a further embodiment, the probe may comprise a stem-loop structure and a single-stranded region at the 3' end, wherein said 3' end region comprises a first target-binding site which is capable of hybridising to a complementary binding site in the target molecule, said complementary binding site being a 3' flanking sequence flanking the 3' end of the ROI, and said loop comprises the second binding site which is homologous to the 5' end of the ROI, or to the ROI, and is capable of hybridising to a complement of the ROI, or of the 5' end thereof, and, 3' to the second binding site, a further probe sequence which is homologous to the 3' flanking sequence and complementary to the first binding site, and wherein said stem-loop structure further comprises a cleavage site 3' of the second binding site and further probe sequence such that cleavage allows the loop to open.

The probe binds to the complementary binding site in the target nucleic acid molecule, wherein the complementary binding site is a flanking sequence flanking the 3' end of the ROI, in a selective manner via its 3' end. The target templated extension of the probe allows a complement of the "selected" target fragment comprising the ROI and flanking sequences to be generated. The extended probe is subsequently cleaved at least at the cleavage site in the stem-loop structure of the probe (e.g. in the stem or loop of the probe), and circularised by ligation of the ends of the extended strand in a probe-templated ligation.

The target ROI is selected by providing a probe with a first target binding site which binds to (i.e. is capable of hybridising to) a region (a 3' flanking sequence or "complementary binding site") flanking the target ROI, which facilitates the production of a complement strand of the target nucleic acid molecule, i.e. the target ROI and flanking sequences (the sequences on either side of the ROI). To enable the extended probe (containing a complement of the ROI) to be circularised a second binding site homologous to a 5' flanking sequence flanking the target ROI (or "homologous sequence"), which binds to (i.e. is capable of hybridising to) the complement of the 5' flanking sequence, is provided by a nucleotide sequence in the loop of the stem-loop structure or in the second strand of a double-stranded probe. The region of the target nucleic acid molecule that is 'selected' is thus defined by the sequences of the complement of the first target binding site, and the second binding site in the probe, and the target ROI is the sequence between the two flanking sequences. Alternatively viewed, the complement of the region of the target nucleic acid molecule is 'selected', which is defined by the sequence of the first target binding site and the complement of the second binding site. Thus the sequences of the first target binding site and the second binding site of the probe determine the region of the target nucleic acid molecule that is 'selected' and incorporated into a circularised nucleic acid molecule.

In certain embodiments of the invention, the 5' flanking region may overlap with or comprise the ROI or a part thereof (i.e. the 5' portion of the ROI). In other words, the ROI, or the 5' part thereof may comprise or contain the flanking region, either in all or in part. Put another way, the ROI may be viewed, or may act, as the 5' flanking region as defined herein, i.e. the complement of the ROI may hybridise to the second binding site in order to form a circularisable structure for ligation. Thus, in one particular embodiment, the 5' flanking region may be viewed as being situated within the ROI, particularly at the 5' end of the ROI, such that the complement of the ROI comprises at its 3' end a sequence complementary to the 5' flanking region (and thus to the 5' end of the ROI), which sequence may hybridise to its complementary sequence in the second binding site of the probe. A complement of the ROI, or a portion thereof, may therefore hybridise to the second binding site in order to bring the 3' and 5' ends of the first extended strand of the probe into juxtaposition for ligation. In order for the circularisation of the probe to occur the target nucleic acid molecule must be removed (i.e. the interaction between the probe and target must be disrupted, e.g. denatured) to leave an extended probe comprising a complement of the target nucleic acid and a free 3' end. Furthermore, where the probe comprises a stem-loop structure, the stem-loop structure 3' to the second binding site is cleaved, which opens the stem-loop structure and results in the formation of a partially double-stranded construct comprising a first extended strand (which may be viewed as the "circularisable strand") comprising the target complement (i.e. a sequence that is complementary to the target nucleic acid), and a second strand (which may be viewed as the "ligation template strand") hybridised to the first strand via the "stem" region and comprising the released 3' end (which comprises the second binding site or homologous sequence). The stem region of the stem-loop structure may be defined as having first (i.e. 3') and second (i.e. 5') strands, or "stem sequences", which hybridise to form the stem of the stem-loop structure. The first extended (circularisable) strand also comprises a 5' end which is released by the cleavage (a "released 5' end). This end is conveniently hybridised in the stem structure remaining after cleavage. Accordingly the term "released 5' end" does not imply that the 5' end is free; it may be hybridised to the second strand in the construct. The term "released" merely conveys that the 5' end is a 5' end of the probe/strand after cleavage. The released 3' end of the probe (specifically of the second strand in the construct is a released free 3' end. Thus, upon cleavage of the stem-loop structure of the probe, the first stem sequence forms part of the circularisable strand and the second stem sequence forms part of the ligation template strand. Each strand in the partially double-stranded construct (i.e. the opened stem-loop structure) comprises a 3' overhang, and the strands are hybridised via the first and second stem sequences derived from the stem of the stem-loop structure (i.e. the sequences that formed the stem of the stem-loop structure prior to cleavage). The 3' overhang of the first strand (i.e. the extended strand or circularisable strand) of the "stem structure" (i.e. the partially double stranded construct) comprises the complement of the target molecule (including the complement of the 5' flanking sequence flanking the target ROI). The 3' overhang of the second strand (i.e. the ligation template strand) of the "stem structure" comprises the second binding site (or homologous sequence), which is capable of hybridising to the complement of the 5' flanking sequence flanking the target ROI. Thus the 3' overhang regions of the partially double-stranded nucleic acid construct comprise a region of complementarity to each other and allow the construct to undergo an intramolecular rearrangement such that the 3' and 5' ends of the first strand of the partially double-stranded construct are brought into juxtaposition for ligation (directly or indirectly), which is templated by the second strand (the ligation template strand) of the partially double-stranded construct. More particularly, intramolecular ligation of the first strand (the circularisable strand) is templated by the second binding site (or homologous sequence) of the probe, which forms part of the second strand (the ligation template strand) of the partially double-stranded construct. An example of the mechanism of a probe of the present invention is depicted in FIG. 1.

Where the probe is a partially double-stranded construct, it will be apparent that the extended probe (i.e. comprising a first, extended strand comprising at least the complement of the ROI and a second strand comprising at least the second binding site, said first and second strands being hybridised by a region of complementarity) is analogous to an extended probe comprising a stem loop structure as described above, having been cleaved in the stem loop structure 3' to the second binding site to release the 3' end of the first strand. Accordingly, the 3' overhang regions of the partially double-stranded nucleic acid construct comprise a region of complementarity to each other and allow the construct to undergo an intramolecular rearrangement such that the 3' and 5' ends of the first strand of the partially double-stranded construct are brought into juxtaposition for ligation, templated by the second strand of the partially double-stranded construct.

Thus, direct or indirect ligation of the ends of the extended (circularisable) strand of the probe may occur when the 3' end of the extended (circularisable) strand is hybridised to the second binding site on the ligation template strand. However, in some embodiments, the 5' flanking sequence flanking the target ROI may be internal to the 5' end of the target nucleic acid molecule, meaning that the extension product formed after probe binding and extension will comprise a region at its 3' end that is not complementary to the second binding site within the stem loop structure or second probe strand (i.e. the extended probe will contain a region that is complementary to the region beyond the 5' flanking sequence). Thus where a target nucleic acid molecule comprises a 5' flanking sequence internal to its 5' end, it is necessary to remove the sequence complementary to the region beyond the 5' flanking sequence (e.g. by cleavage, such as using a 3' exonuclease) in order for ligation to occur (see FIG. 5).

Thus the extension of the probe creates a region of intramolecular complementarity, i.e. a region at or towards the 3' end of the extended probe is complementary to the second binding site (the homologous sequence). However, these complementary regions are not able to interact until the target nucleic acid is removed and the stem-loop structure (if present) has been opened by cleavage, thereby reducing the chance of non-specific ligation from taking place.

Thus, at its broadest, the probe of the invention comprises a first target binding site and a second binding site as defined above, but may optionally comprise further sites or regions, e.g. sites or regions capable of binding to, or homologous to, a target nucleic acid molecule, and/or additional sequence elements to enable or facilitate various downstream applications. However, the method of the invention whereby a target ROI is selected based on its 3' and 5' flanking sequences is not reliant on the presence of any additional elements, which are provided to facilitate one or more aspects of the method of the present invention and which are discussed in more detail below. Representative probe designs and their modes of action are depicted in FIGS. 1-5 and 10-13.

As mentioned above, the intramolecular ligation of the probe may be direct, when the 3' and 5' ends of the extended strand (i.e. the circularisable strand, which is the first strand of the partially double-stranded "open" construct) are ligated directly together, or it may be indirect when the 3' end of the extended (circularisable) strand hybridises to the second binding site in the probe (in the ligation template strand) with a space (i.e. gap) or intervening sequence between it and the 5' end of the extended strand. As will be described in more detail below, this may occur when an additional sequence element (or "spacer sequence") is introduced in the probe. In such a configuration the gap between the ends of the extended strand may be filled, either by a "gap" oligonucleotide, which hybridises to the spacer sequence (i.e. the intervening sequence) between the second binding site in the probe and the second stem sequence (i.e. the stem sequence of the template ligation strand, which is the second strand of the partially double-strand "open" construct), or by extension of the hybridised 3' end of the fragment. The gap oligonucleotide may be provided pre-hybridised to the intervening or spacer sequence in the probe, or added separately, e.g. later during the method. It may also be provided in one or more parts.

The target ROI which is selected may be any desired sequence or subsequence in a target nucleic acid molecule. The ROI may thus alternatively be termed a "target sequence" in a target nucleic acid molecule. For example it may be a region of a nucleic acid in a sample which it is desired to amplify.

The term "selecting" is used broadly herein and includes any means of selecting, isolating and/or separating a nucleic acid sequence of interest, for example from a nucleic acid sample which contains other nucleic acid molecules, particularly other DNAs or RNAs, in addition to the target nucleic acid molecule or indeed from a longer nucleic acid molecule containing the target ROI.

The target nucleic acid molecule is thus any nucleic acid molecule containing the target ROI. As will be discussed in more detail below, it may thus be a genomic molecule or a fragment thereof, or any kind of synthetic or artificial nucleic acid molecule. In a preferred embodiment, the nucleic acid molecule is an RNA molecule or a fragment thereof. Thus "selecting" encompasses any means of practically, if not actually physically, "separating" the target ROI (or more particularly a complement thereof) from the other nucleic acids present in a sample, and/or from the rest of the target molecule. The complement of the selected ROI contained in the circularised probe may be subjected to amplification, e.g. by one of the many known methods of nucleic acid amplification, to amplify the ROI, for example for detection of the ROI or to enable further analysis, e.g. by sequencing, or to physical separation, e.g. capture, for example by immobilisation to a solid phase, optionally followed by amplification.

The method of the invention may thus include a further step of analysing the ROI, i.e. the complement of the selected ROI contained in the circularised probe or an amplicon thereof. As will be described further below, this may be by sequencing, or by a method of sequence analysis (e.g. detecting the presence or absence of a sequence variant or a particular nucleotide(s) in the ROI), or by hybridisation of a detection probe to the ROI, optionally with further detection and/or signal amplification steps.

Such an analysis step will allow a target ROI to be detected, for example in a sample containing nucleic acids. The target ROI may therefore in one embodiment be a target analyte.

Accordingly, in a still further aspect the invention can also be seen to provide a method of detecting a target ROI, for example using a probe of the invention to bind to a target nucleic acid molecule containing the ROI and to select the target ROI as hereinbefore described.

The term "detecting" is also used broadly herein and includes any means of identifying, detecting or determining or assaying for the presence of the target ROI, or any means of analysing the target ROI. Direct analysis of the target ROI (i.e. sequencing of all or any part of the target ROI) is encompassed by the term "detecting".

The method of the invention may be performed in "simplex" format to enrich for a single target ROI (i.e. a single species of target ROI, which will normally be present in many copies) or for a plurality of target ROIs which are sufficiently similar in sequence, or flanked by sufficiently similar, or identical, sequences so as to be possible to select them using the same probe. In this context it will be seen that the term "single" as used in relation to the probe means single in the context of a particular target ROI, namely that one probe (or more particularly one type or species of probe) is used for each target ROI (i.e. a single probe per target ROI). It is clear from the above that "single" probe means single species of probe and does not imply any limitation on the actual number of probe molecules used.

Alternatively, a plurality (i.e. a plurality of species) of probes may be used in a "multiplex" format simultaneously to enrich for a plurality of target ROIs, which may be in the same, or more typically, in different, target molecules. Hence, in such a latter aspect the method as defined above is for selecting a plurality of target ROIs, wherein a plurality of probes is provided, each designed to select a different target ROI. In such an embodiment each probe may have a different first target-binding site and/or second binding site, e.g. within its stem-loop or in the single-stranded regions at the 3' end regions of the first and second strands, i.e. the probes have different target-specificities. In such a multiplex method, for each target ROI of the plurality (i.e. each different type or species of target ROI) a single (i.e. in the sense of a single species of) probe may be used. Thus, a plurality of probes may be used, with a (different) probe for each target ROI. Thus in one embodiment each probe has a different first target binding site and/or second binding site, whereby a plurality of different target nucleic acid molecules (and thus a plurality of different target ROIs) may be selected. In another embodiment, different ROIs in the same target molecule (e.g. where the target molecule is derived from a plurality of sources) may be selected. In a still further embodiment, the same probe (i.e. comprising a single set of first and second binding sites) may be used to detect a plurality of different target ROIs that might be present within the same target nucleic acid molecule derived from a plurality (variety) of different sources.

The term "plurality" as used herein means 2 or more (or at least 2), more particularly 3 or more (or at least 3), or 4, 5, 6, 8, 10, 15, 20, 30, 50, 70 or 100 or more etc. In certain embodiments even higher numbers of probes may be used and very many different target ROIs may be selected, e.g. 500, 1,000, 2,000, 5,000 or 10,000 or more. For example, 10, 100, 1,000 or 10,000 different probes may simultaneously be used to detect or enrich for, respectively, 10, 100, 1,000 or 10,000 different target ROIs.

The target ROI may be any sequence it may be desired to detect, analyse or amplify, for example a nucleotide sequence or a nucleic acid or selected part thereof in a pool of nucleic acid molecules or nucleotide sequences, for example genomic nucleic acids, whether human or from any source, from a transcriptome, or any other nucleic acid (e.g. organelle nucleic acids, i.e. mitochondrial or plastid nucleic acids), whether naturally occurring or synthetic. The target nucleic acid molecule may therefore be any kind of nucleic acid molecule. Thus it may be DNA or RNA, or a modified variant thereof. Thus the nucleic acid may be made up of ribonucleotides and/or deoxyribonucleotides as well as synthetic nucleotides that are capable of participating in Watson-Crick type or analogous base pair interactions. Thus the nucleic acid may be or may comprise, e.g. bi-sulphite converted DNA, LNA, PNA or any other derivative containing a non-nucleotide backbone. The target molecule or ROI may thus be coding or non-coding DNA, for example genomic DNA or a sub-fraction thereof, or may be derived from genomic DNA, e.g. a copy or amplicon thereof, or it may be cDNA or a sub-fraction thereof, or an amplicon or copy thereof etc. Alternatively, the ROI or target molecule may be or may be derived from coding (i.e. pre-mRNA or mRNA) or non-coding RNA sequences (such as tRNA, rRNA, snoRNA, miRNA, siRNA, snRNA, exRNA, piRNA and long ncRNA). In a preferred embodiment, the target nucleic acid molecule is an RNA molecule. In a particularly preferred embodiment, the target nucleic acid molecule is a micro RNA (miRNA).

In certain embodiments the 5' end of the target molecule is defined. Thus, the 5' end of the target molecule is known, and/or comprises the 5' end of the ROI it is desired to detect. In such a situation the 5' flanking sequence may be (i.e. may form or provide) the 5' end of the molecule. In other embodiments or aspects the 5' end of the ROI may be (i.e. may form or provide) the 5' end of the molecule. Such target molecules include particularly RNA molecules e.g. miRNA molecules or a transcript or mRNA molecule. Thus the defined end may be the 5' end of a miRNA molecule or the 5' end of a transcript.

The probe may similarly be composed of or may comprise any nucleic acid as detailed above. The sequence of the target ROI may not be known, providing that the sequence of the regions flanking the target ROI are known in order to facilitate the design of the probe, which must be able to hybridise to the 3' flanking sequence, and the complement of the 5' flanking sequence, as defined and explained above. However, in certain embodiments the sequence of the target ROI may be known, e.g. where the probe contains a second binding site being homologous to the ROI, or where the ROI comprises the 5' flanking sequence. Thus, a sequence at a location 5' of the complement of the first binding site must be known in order to design a probe for use in the methods of the present invention. This may be the 5' flanking region, or the ROI or a part thereof.

The method of the present invention requires that the nucleic acid probe is extended in order to 'select' the target region of interest, whereby the target nucleic acid molecule acts as an extension template to generate a complement (i.e. viewed 5' to 3' the reverse-complementary sequence) of the target nucleic acid molecule. Any suitable polymerase may be used in the method of the present invention, such as RNA polymerases (DNA→RNA), DNA polymerases (DNA→DNA) or Reverse Transcriptase (RNA→DNA). However, the specific nucleic acid polymerase required for the extension of the 3' end of the probe may depend on the nature of the target nucleic acid molecule, the size of the target ROI, and the nature of the analysis that is to be performed on the selected target ROI.

The size of the target ROI is not critical and may vary widely. Thus in one embodiment of the present invention the target ROI may be at least 10 nucleotides, and preferably at least 15 nucleotides in length. Thus the target ROI may be at least 20, 25, 30, 40, 50, 60, 70, 80 or 90 nucleotides in length. It is also anticipated that the present method may be used to select a longer target ROI, for example where the target ROI is at least 100, 150, 200, 300, or 400 nucleotides in length, or up to 500, 1,000, 1,500, 2,000, 2,500, 3,000, 5,000, 10,000, 25,000, 50,000 or 100,000 nucleotides in length. Although RCA of nucleic acid circles may become less efficient as the size of the circle increases (e.g. above 5,000 or 10,000 nucleotides) it is still feasible. Thus representative ranges of ROI length include from any one of 10, 12, or 15 up to any one of 100,000, 50,000, 25,000, 10,000, 5,000, 2,000, 1,000, 800, 750, 700, 600 or 500 nucleotides. In particular embodiments, the size range may be from any one of 10, 12, or 15 to any one of 500, 400, 300, 200, 100 or 50 nucleotides.

The target nucleic acid molecule may be present within a sample. The sample may be any sample which contains any amount of nucleic acid, from any source or of any origin, from which it is desired to select a target ROI. A sample may thus be any clinical or non-clinical sample, and may be any biological, clinical or environmental sample in which the target nucleic acid molecule may occur. More particularly, the sample may be any sample that contains nucleic acid. The target nucleic acid molecule may occur in single-stranded or partially single-stranded or in double-stranded form. However, as noted above for the practice of the method the target molecule needs to be single-stranded at least in the regions where the probe hybridises. Where necessary, the method may therefore comprise a step of rendering the target nucleic acid at least partially single-stranded, as discussed further below.

As noted above, the selection of the target ROI by the method outlined herein requires the removal of the target nucleic acid molecule following the extension of the hybridised 3' end of the probe in order to render the complement of the target nucleic acid molecule single-stranded. The target nucleic acid molecule can be removed by any suitable means known in the art, depending on the type, size and nature of the target nucleic acid. For example, the target nucleic acid molecule may be removed by denaturation (for instance by altering the conditions in the sample or assay, such as by heating or altering the concentration of components, such as salts, or by the addition of a denaturing substance or agent such as urea, or any other denaturing or chaotropic agent) and/or by strand-specific chemical or enzymatic degradation of the target nucleic acid molecule.

As noted above, where the probe is provided as a partially double-stranded construct, or where it is cleaved before contacting with the target molecule, the step of removing the target molecule is done or performed in such a way that the second binding site remains in the probe. Thus in such a case a method which would result in denaturation of the probe is not used. In practice this may mean that a denaturation method is not used, particularly heat denaturation is not used. A method using a partially double-stranded probe, or cleaving the probe prior to target contact thus has particular utility in the case of an RNA target molecule, since a hybridised RNA molecule may readily be removed whilst leaving the extended probe intact. Accordingly where denaturation is not required or is not used to remove the target molecule, a probe comprising a stem-loop structure may be cleaved to open the loop at the start of the method, e.g. before contacting with the target, or more generally, before, during or after, the contacting step, the extension step or the removal step.

For example, alkaline hydrolysis or RNase digestion can be used to degrade an RNA target nucleic acid molecule, or Mung bean nuclease can be used to degrade a single-stranded DNA target molecule. In embodiments where the target nucleic acid molecule is RNA, any suitable RNase may find utility in the methods described herein. In a particularly preferred embodiment, the target nucleic acid molecule comprises RNA and the step of removing the target molecule comprises alkaline hydrolysis, e.g. contacting the sample or assay with a base, such as NaOH or KOH, which may denature the duplex between the target nucleic acid and the extended probe and also degrade the target nucleic acid. Degradation of a target nucleic acid molecule can also occur in addition to (i.e. before, simultaneously with, or after) a step of denaturation. Thus, in some embodiments, the step of removing the target nucleic acid molecule may comprise a first step of denaturing the duplex between the target nucleic acid and the extended probe followed by a second step of degrading (i.e. selectively degrading) the target nucleic acid molecule.

A separation step may optionally be employed following, or as part of, the removal of the target nucleic acid molecule to ensure that none of the target nucleic acid molecule is present in the sample before continuing with the method of the invention. Separation may include any means of specifically removing the unwanted target nucleic acid molecule or isolating the extended probe, for instance by immobilising the probe on a solid phase, washing the sample with a suitable buffer, gel electrophoresis, high performance liquid chromatography (HPLC) or preferentially precipitating either the target nucleic acid molecule or extended probe. Accordingly, in some embodiments the step of removing the target nucleic acid molecule may comprise a step of separating the extended probe from other nucleic acid molecules in the sample. Alternatively viewed, the method may comprise a step of isolating or purifying (partially or fully) the extended probe from other components in the sample, e.g. other nucleic acid molecules, particularly target nucleic acid molecules.

In one embodiment of the above method, the target ROI may be detected in situ, as it naturally occurs in the nucleic acid molecule in the sample. In such an embodiment the target nucleic acid molecule may be present in a sample at a fixed, detectable or visualisable position in the sample. The sample will thus be any sample which reflects the normal or native ("in situ") localisation of the target nucleic acid molecule, i.e. any sample in which it normally or natively occurs. Such a sample will advantageously be a cell or tissue sample. Particularly preferred are samples such as cultured or harvested or biopsied cell or tissue samples in which the target ROI may be detected to reveal the localisation of the target ROI relative to other features of the sample. As well as cell or tissue preparations, such samples may also include, for example, dehydrated or fixed biological fluids, and nuclear material such as chromosome/chromatin preparations, e.g. on microscope slides. The samples may be freshly prepared or they may be prior-treated in any convenient way such as by fixation or freezing. Accordingly, fresh, frozen or fixed cells or tissues may be used, e.g. FFPE tissue (Formalin Fixed Paraffin Embedded).

Thus, representative samples may include any material which may contain a target nucleic acid molecule, including for example foods and allied products, clinical and environmental samples etc. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include clinical samples, e.g. whole blood and blood-derived products such as plasma, serum and buffy coat, blood cells, other circulating cells (e.g. circulating tumour cells), urine, faeces, cerebrospinal fluid or any other body fluids (e.g. respiratory secretions, saliva, milk, etc.), tissues, biopsies, as well as other samples such as cell cultures, cell suspensions, conditioned media or other samples of cell culture constituents, etc.

Although the method of the present invention may be used to select a target ROI in a target nucleic acid molecule in an in situ (i.e. a native) setting, it is also contemplated that the method may be employed to select a target ROI in a target nucleic acid molecule in an in vitro detection system, i.e. where a target nucleic acid molecule has been isolated or purified from its native setting. The sample may thus be a direct product of a nucleic acid isolation procedure, or of a cell lysis procedure, or it may further be fractionated or purified in some way, e.g. it may contain nucleic acids which have been partially or fully separated from their native environment. The sample may also be treated in any way, e.g. to produce the cDNA reverse transcript of an RNA molecule.

Although a fragmentation step is not necessary, it may in the case of certain target nucleic acid molecules or certain samples, e.g. in the context of genomic DNA, be desirable or convenient to include a fragmentation step in the method, such that the nucleic acid in the sample, or the target molecule, is fragmented prior to the hybridisation of the probe. This may occur prior to or at the same time, or substantially the same time, as contacting the sample, or the target nucleic acid molecule with the probe. As mentioned above, where the target molecule is double-stranded, a step of rendering the molecule at least partially single-stranded is required. This step may be separate to the fragmentation step, e.g. after fragmentation, but may occur as part of the fragmentation step. Fragmentation may be required or helpful in order to allow the at least partially single-stranded nucleic acid to be prepared.

The term "fragmenting" is used broadly herein to include any means by which the nucleic acid in the sample, or more particularly the target molecule, may be fragmented or cleaved. Thus, fragmentation may be carried out enzymatically, e.g. using restriction or other endonucleases or nucleases such as DNase, and/or physically, e.g. by nebulisation or sonication or any shear-based methods. Such physical methods result in unpredictable, non-sequence-specific fragmentation, as do certain (non-restriction) endonucleases. Thus both random, and pre-determined (or site-specific) fragmentation is encompassed, but the latter is not necessary. Also encompassed by "fragmenting" is fragmentation of a nucleic acid sample which inherently may occur as a result of the age of a sample, the conditions in which it is stored and any treatment of the sample (e.g. fixation, such as in formalin-fixed paraffin-embedded samples), and the degradation to which these factors contribute. Any suitable class of restriction endonuclease may be used, including type II and type IIs enzymes. Alternatively, fragmenting may be achieved using a flap endonuclease (FEN), wherein an added nucleic acid or oligonucleotide is used to create a structure which is a substrate for such as structure-specific endonuclease, i.e. a structure having a protruding non-hybridised 5' end region. Fragmenting means may be used in combination, e.g. the use together of two or more endonucleases, more particularly two or more restriction endonucleases, or the use together of an enzymatic and a physical means. Furthermore, the nucleic acid sample may be differently fragmented in separate aliquots, which aliquots are then pooled and together subjected to the remaining steps of the method of the invention. In certain cases, it may be appropriate and sufficient to fragment using a single restriction endonuclease, but in other cases the use of additional restriction endonucleases may be preferred.

Hence, the fragmenting may be achieved by separating the nucleic acid sample into a plurality of aliquots and fragmenting the respective aliquots with different means or different combinations of means, such means being for example restriction enzymes. Any number of aliquots of the sample may be differently treated, e.g. 2 or more, or 3, 4, 5, 6, 7, 8, 9, 10, 11, 12, 13, 14, 15 or 20 or more etc. The aliquots are then subjected to the remaining steps of the method and may be pooled, for example before step (b).

Before the target molecule can hybridise with the probe, it must be at least partially single-stranded. This may be achieved, if necessary, by any means known in the art, such as denaturation, e.g. by heat or pH, or through the use of chemicals, e.g. alkali. Heat denaturation is preferred.

Thus, after or concomitantly with any fragmenting step, the nucleic acid in the sample, including the target nucleic acid molecule, may if necessary be rendered at least partially single-stranded, to allow probe hybridisation in step (b) to occur. Where the nucleic acid molecule is not made completely single-stranded, it is required that it is single-stranded at least in the portion(s) which comprise(s) the probe-complementary portion(s) (so as to allow binding to the probe), i.e. the complementary binding site of target nucleic acid molecule is single stranded to allow the first target binding site of the probe to bind. In some embodiments it may be particularly preferred that the region 5' to the probe binding site (the complementary binding site) that acts as the template for the extension of the probe is single stranded. However, in some embodiments the region 5' to the probe binding site (the complementary binding site) may be double stranded, for instance, when the probe is extended used a strand displacement polymerase, such as phi29 (i.e. a polymerase with strand displacement activity). Polymerases with strand displacement activity are well known in the art and any suitable strand displacement polymerase may find utility in the methods of the invention. As well as by denaturation, at least partial single-strandedness can be achieved by 3' or 5' exonucleolysis using an appropriate 3' or 5' exonuclease. Starting at a free double-stranded fragment end, such enzymes progressively degrade or digest one strand of a double-stranded nucleic acid, leaving the complementary strand and rendering the nucleic acid single-stranded along the length of the enzyme's action. The extent of exonucleolytic degradation (i.e. the length of the resulting single-stranded region) may be controlled by the duration of the reaction. The duration of the exonuclease reaction is chosen in order that an appropriate length of one end of the strands of the fragments is removed. The extent of digestion must be sufficient to allow hybridisation with the probe. Suitable exonucleases are known in the art and include, e.g. exonuclease III (3') and lambda exonuclease (5').

Further, in certain applications, for example in situ procedures, the duplex of a target nucleic acid molecule may be opened up to permit probe hybridisation, without fully denaturing the nucleic acid. Procedures for this are known in the art.

In some embodiments, the circularised strand may be detected by RCA, wherein it may be useful to facilitate localisation of the RCA product to its native position, e.g. such that the RCA product functions as a localised marker for the target nucleic acid molecule in the sample. For instance, the RCA product may be localised to the sample by immobilising the RCA product to the target nucleic acid or in proximity to the target nucleic acid. Methods for immobilising the RCA product are described further below. However, in a representative example, the probe may comprise a spacer (intervening) sequence that functions as an anchor or capture sequence. In some embodiments, the capture sequence may form part of the ligation template strand of the probe and may comprise a sequence that is capable of binding to the target nucleic acid molecule or a complement thereof directly or indirectly. More particularly, the capture sequence may bind to the target molecule at a site distinct from the ROI and flanking sequences, For example, the capture sequence may be complementary to the target nucleic acid or a complement thereof (e.g. if the target nucleic acid is a double stranded molecule, such as DNA, e.g. genomic DNA), e.g. a sequence that is complementary to a region flanking the ROI or one of the ROI flanking sequences (such as a sequence flanking the flanking sequence flanking the 3' end of the ROI). Thus, following the step of removing the target molecule (i.e. after step (d) of the method described above), the capture sequence may hybridise to the target molecule thereby directly immobilizing the ligation template strand to a location at or near the site of the ROI. As the ligation template strand may also function as the primer for RCA, the subsequent RCA product may be localised at or near the site of the ROI. Alternatively, the capture sequence may be complementary to a capture oligonucleotide that contains a region of complementarity to the target nucleic acid or a complement thereof and therefore is capable of immobilising the probe on the target nucleic acid molecule, and therefore, indirectly, immobilising the RCA product on the target nucleic acid molecule. It will be understood that where there is a second cleavage (i.e. where the 5' flanking sequence (or the ROI) is internal to the 5' end of the target molecule), the capture sequence will be located in the probe at a site or location which is internal to a second cleavage site in the probe (see further below). Such a capture sequence may be viewed as an anchor sequence. In particular, such a capture sequence serves to capture or anchor the extended probe, or more particularly an amplification product of the extended probe. Thus, this may be viewed as a localisation sequence, particularly a localisation sequence for an amplification product of the extended probe.

In another representative embodiment, the primer for RCA may be provided separately, wherein the primer contains a sequence capable of hybridising to the circularised strand of the probe and a sequence capable of hybridising to the target nucleic acid or a complement thereof, e.g. a sequence that is complementary to a region flanking the ROI or one of the ROI flanking sequences. Thus, upon RCA, the RCA product will be immobilised on the target molecule, e.g. at or near to the ROI, such as proximal to the ROI.

In some embodiments it is not necessary to actively immobilise the RCA product, e.g. to the target nucleic acid molecule, in order to produce a localised signal in situ (see e.g. Example 2 and FIG. 8). In this respect, whilst not wishing to be bound by theory, it is hypothesized that the RCA product rapidly becomes too large to readily diffuse away from its source, i.e. the RCA product is localised in its cell of origin even though it may not be directly or indirectly immobilized, e.g. to, or in proximity to, the target nucleic acid.

A number of different designs may be employed for the probe of the present invention. At its simplest, as depicted in FIG. 1, the probe is a hairpin or stem-loop probe comprising a single-stranded region at the 3' end, wherein the first target-binding site and the second binding site are separated by the stem of the stem-loop. Thus, the probe comprises at least a first 3' target binding site capable of hybridising to a flanking sequence flanking the 3' end of the target ROI, a stem-loop structure comprising a second binding site homologous to a flanking sequence flanking the 5' end of the target ROI and a cleavage site within the stem-loop structure (e.g. within the stem or loop), 3' of the second binding site. However, further designs of the probe may be employed which may comprise one or more additional target binding sites, additional regions of homology to portions of the target molecule, and/or one or more additional sequence elements which may act as spacers or enable or facilitate the selection of the target ROI.

It will be evident that the single-stranded region at the 3' end of the probe need not be completely single-stranded prior to its interaction with the target nucleic acid molecule. For instance, the 3' end of the probe may comprise a region of secondary structure, e.g. a hairpin at or near the 3' end. The 3' end of the probe must simply be capable of hybridising specifically to a flanking sequence flanking the 3' end of the target ROI and functioning as a primer for extension of the probe using the target nucleic acid molecule as a template for extension. Thus, for example, if the 3' end of the probe comprises a hairpin region, the interaction between the first binding site and the flanking sequence flanking the 3' end of the target ROI is more stable (i.e. thermodynamically more favourable) than the intramolecular hybridisation at the 3' end of the probe such that in the presence of the target nucleic acid molecule, the 3' end of the probe unfolds to allow the interaction between the probe and target nucleic acid. This may be particularly advantageous to reduce non-target specific binding and extension.

In a first variant embodiment, as depicted in FIG. 2, the probe may comprise a third binding site 5' to the stem-loop structure, said binding site having homology to a sequence immediately 5' to the 5' flanking sequence in the target molecule, and being capable of hybridising to a complement of said sequence. More specifically, the third binding region may lie in a 5' single stranded sequence (i.e. a 5' single-stranded end or region) of the probe. The extended probe is thus able to undergo an intramolecular hybridisation wherein the third binding site hybridises to its complementary binding site in the target complement, thereby generating a second double-stranded region in the extended probe. In one embodiment of the present invention, the third binding site may comprise a sequence capable of forming a second cleavage site when hybridised to its complementary sequence. Thus, such an embodiment has utility in the situation that the 5' flanking sequence in the target molecule (or the ROI) does not lie at the 5' end of the target molecule, but is internal to the 5' end of the molecule. In a preferred embodiment, the cleavage site is a restriction enzyme recognition sequence. In another preferred embodiment, the cleavage site is a nickase recognition sequence that templates the single-stranded cutting of the extended probe in the 3' strand of the second double-stranded region. In some embodiments, the sequence capable of forming a cleavage site (more particularly the second cleavage site) may be situated at or towards the end of the 3' end of the third binding site. Alternatively, the sequence capable of forming a cleavage site may be situated away from the 3' end of the third binding site (i.e. located at or towards the 5' end of the third binding site), such that part of the sequence complementary to the third binding site remains at the 3' end of the first strand of the probe (i.e. the first strand of the partially double stranded "open" probe or circularisable strand) following cleavage (see FIG. 3). In some embodiments where the sequence capable of forming the second cleavage site is situated away from the 3' end of the third binding site, the loop of the stem-loop structure may comprise an additional sequence (i.e. at or towards the 5' end of the loop) that is complementary to at least a portion of the sequence in the target complement which forms the complementary binding site for the third binding site, i.e. the loop of the stem-loop structure comprises a sequence which is complementary to the sequence that remains at the 3' end of the first strand of the probe (the circularisable strand) following cleavage at the second cleavage site. Alternatively viewed, the loop of the stem-loop structure comprises an additional sequence, at or towards the 5' end of the loop, which is homologous to at least a portion of a sequence adjacent (preferably directly adjacent) to the flanking sequence flanking the 5' end of the ROI.

Thus, in some embodiments, wherein when the 5' flanking sequence is internal to the 5' end of the target nucleic acid molecule, the probe further comprises a single-stranded region at the 5' end comprising a third binding site which is homologous to a cleavage sequence 5', e.g. immediately 5', to the 5' flanking sequence in the target molecule and is capable of hybridising to a complement of said cleavage sequence, wherein said third binding site is optionally separated from the 5' end of the stem by a spacer sequence and wherein step (e) of the method described above comprises:

(i) allowing the extended probe to undergo an intramolecular hybridisation wherein the third binding site hybridises to its complementary binding site in the target complement, thereby generating a second cleavage site;

(ii) cleaving the hybridised probe at the second cleavage site and at the cleavage site in the stem-loop structure (e.g. in the stem or loop 3' to the second binding site), thereby generating a partially double stranded construct comprising two strands hybridised at the stem, the first strand comprising the target complement and the second strand comprising the second binding site;

(iii) allowing the second binding site to hybridise to its complementary binding site in the target complement in the first strand, thereby bringing the 5' and 3' ends of the first, extended, strand into juxtaposition for ligation directly or indirectly to each other, using the second binding site as a ligation template.

In still further embodiments, the loop in the probe further comprises 5' to the second binding site a sequence complementary to a sequence from the complementary binding site in the target complement for the third binding site, which sequence remains at the 3' end of the first strand of the probe following cleavage at the second cleavage site.

Figure 10:
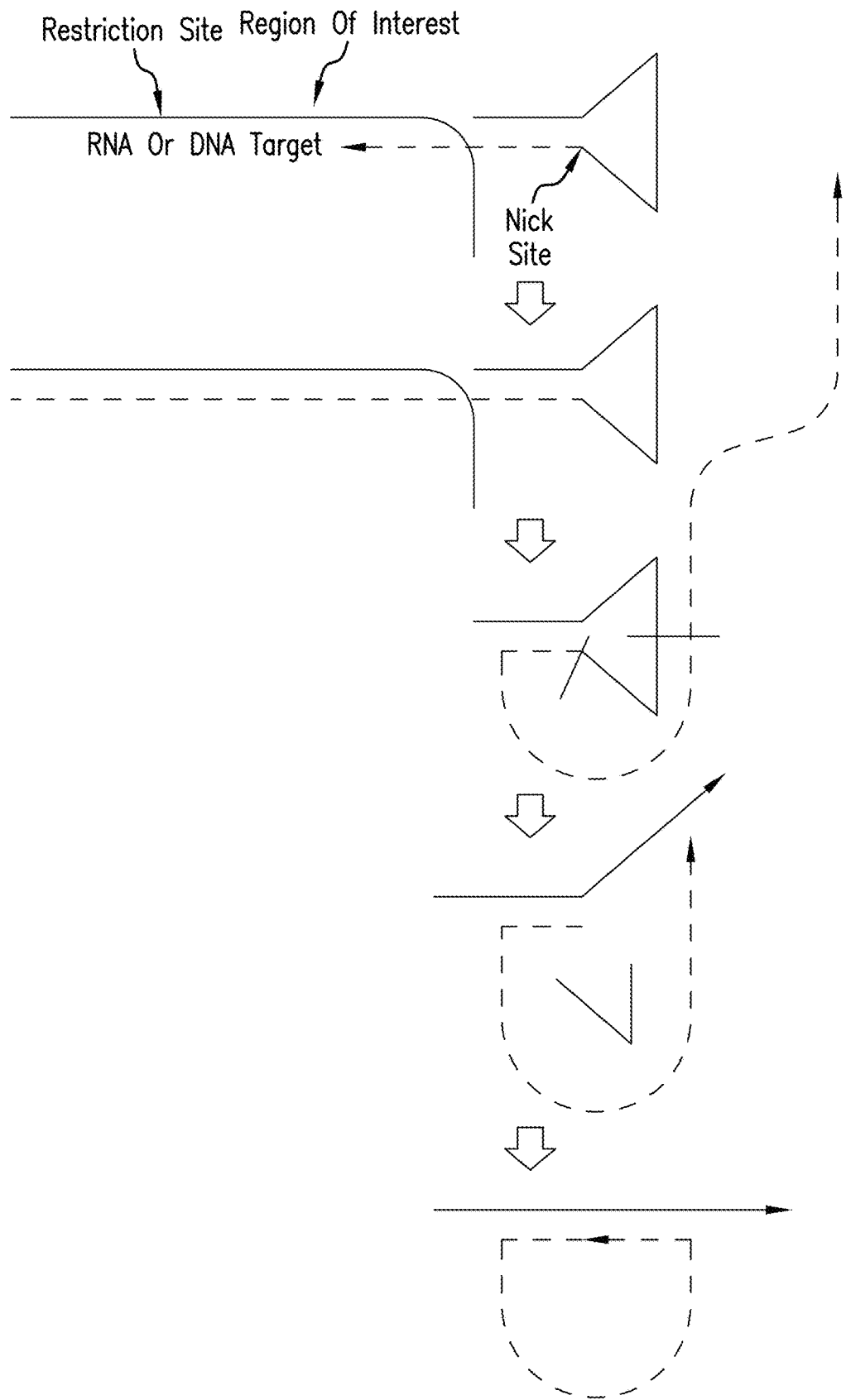

The third binding site need not, however, lie in a 5' single stranded region of the probe, and can be present in an alternative location. Thus, in a further embodiment, which has utility in the situation that the 5' flanking region is internal to the 5' end of the target molecule, the third binding site can be located in the loop of the stem-loop structure. This is illustrated in FIG. 10.

Accordingly, in further embodiments, wherein when the 5' flanking sequence is internal to the 5' end of the target nucleic acid molecule, the probe further comprises a third binding site which is homologous to a cleavage sequence 5', e.g. immediately 5', to the 5' flanking sequence in the target molecule and is capable of hybridising to a complement of said cleavage sequence, wherein said third binding site is in the stem-loop structure, preferably within the loop of the stem-loops structure, and is 3' to the second binding site, and wherein step (e) of the method described above comprises:

(i) allowing the extended probe to undergo an intramolecular hybridisation wherein the third binding site hybridises to its complementary binding site in the target complement, thereby generating a second cleavage site;

(ii) cleaving the hybridised probe at the second cleavage site and at the cleavage site in the stem-loop structure (namely the first cleavage site, e.g. in the stem or loop 3' to the second binding site), thereby generating a partially double stranded construct comprising two strands hybridised at the stem, the first strand comprising the target complement and the second strand comprising the second binding site;

(iii) allowing the second binding site to hybridise to its complementary binding site in the target complement in the first strand, thereby bringing the 5' and 3' ends of the first, extended, strand into juxtaposition for ligation directly or indirectly to each other, using the second binding site as a ligation template. It will be seen that in this embodiment the third binding site, which creates the second cleavage site, lies in the loop between the second binding site and the cleavage site in the stem-loop structure (namely the first cleavage site). Thus the third binding site is 5' of the cleavage site in the stem-loop structure. Where the cleavage site (i.e. first cleavage site) is in the loop, the third binding site is 5' of the cleavage site.

Where the third binding site that is used to template cleavage of the extension product lies in the loop, it may be important carefully to balance hybridisation strengths.

In further variant embodiments, the probe may comprise at least one (i.e. one, two, three or more) additional sequence elements (spacers or intervening sequences). For instance, one or more intervening sequences or spacers may be present between the first target binding site and the stem-loop structure, within the stem-loop structure, or 5' of the stem-loop structure, including in an optional single-stranded 5' region of the probe. An intervening sequence or spacer may also be present within the loop and/or stem sequence of the stem-loop structure. For instance, the intervening sequence could form a single stranded loop in the stem of the stem structure, e.g. the first stem sequence may comprise a region that is not complementary to the second stem sequence thereby forming a loop in the stem when the first and second stem sequences hybridise to each other. In a preferred embodiment, the spacer within the loop of the stem-loop structure is located 5' of the second binding site, i.e. between the second binding site and the second stem sequence of the stem-loop structure. Multiple intervening sequences or spacers may thus be present within the probe, interspersed between the various regions of the probe as defined herein. As noted above these may be used to introduce elements useful for or which facilitate downstream processing or handling, for example to introduce tag or detection sequences or elements allowing the probe and/or circularised fragment (i.e. the circularised complement of the ROI) to be captured, for example for immobilisation to a solid phase. In one embodiment this may be a capture, or anchor, sequence designed to immobilise an amplification product of the circularised strand, e.g. an RCA product in situ, e.g. to the target molecule from which it is derived.

Thus the probe may comprise an intervening sequence or spacer between the first target binding site and the stem-loop structure, and/or a spacer 5' of the stem loop structure (i.e. 5' of the second stem sequence, such as between the second stem sequence and the third binding site in a single-stranded 5' end region of the probe as described above or 5' of the second stem sequence and the third binding site, if present), and/or an intervening sequence or spacer within the loop of the stem-loop structure. For example, where the third binding site is in the loop an intervening sequence may lie 3' of the third binding sequence. In a further embodiment, the probe may comprise intervening sequences or spacers between both the first target binding site and the stem-loop structure, and 5' of the stem-loop structure. Where the probe comprises a third binding site, one or more intervening sequences or spacers may be present 3' or 5' of the third binding site. Thus, a spacer may be located at the 5' end of the third binding site, at the 3' end of the third binding site (e.g. between the third binding site and the stem-loop structure), or spacers may be present at both the 5' and 3' ends of the third binding site.

Figure 4:
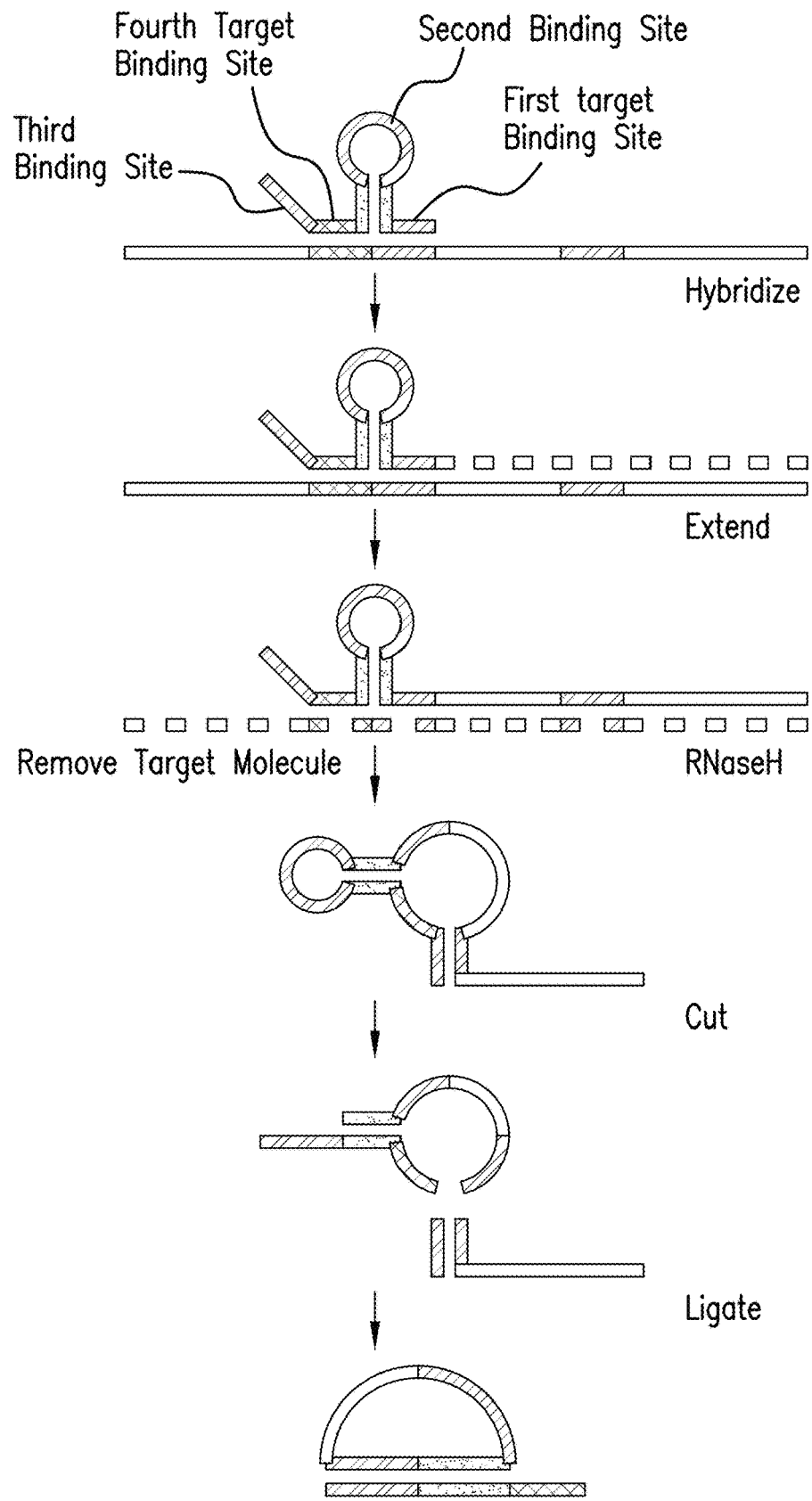

In some embodiments, an intervening sequence or spacer may be located between the third binding site and the stem-loop structure (i.e. 3' of the third binding site and 5' of the second stem sequence), and advantageously may comprise a fourth target binding site which is capable of hybridising to a complementary binding site in the target molecule lying 3', preferably immediately 3', of the 3' flanking sequence of the target molecule (see FIG. 4). The presence of a fourth binding site may stabilise the interaction between the probe and the target nucleic acid molecule, e.g. may improve the selectivity or specificity of the probe.

Thus, in some embodiments, the spacer sequence comprises a fourth target binding site which is capable of hybridising to a complementary binding site in the target molecule lying 3', preferably immediately 3', of the 3' flanking sequence of the target molecule, and step (b) of the method described above further comprises allowing the fourth target binding site to hybridise to its complementary binding site in the target molecule.

Figure 11:
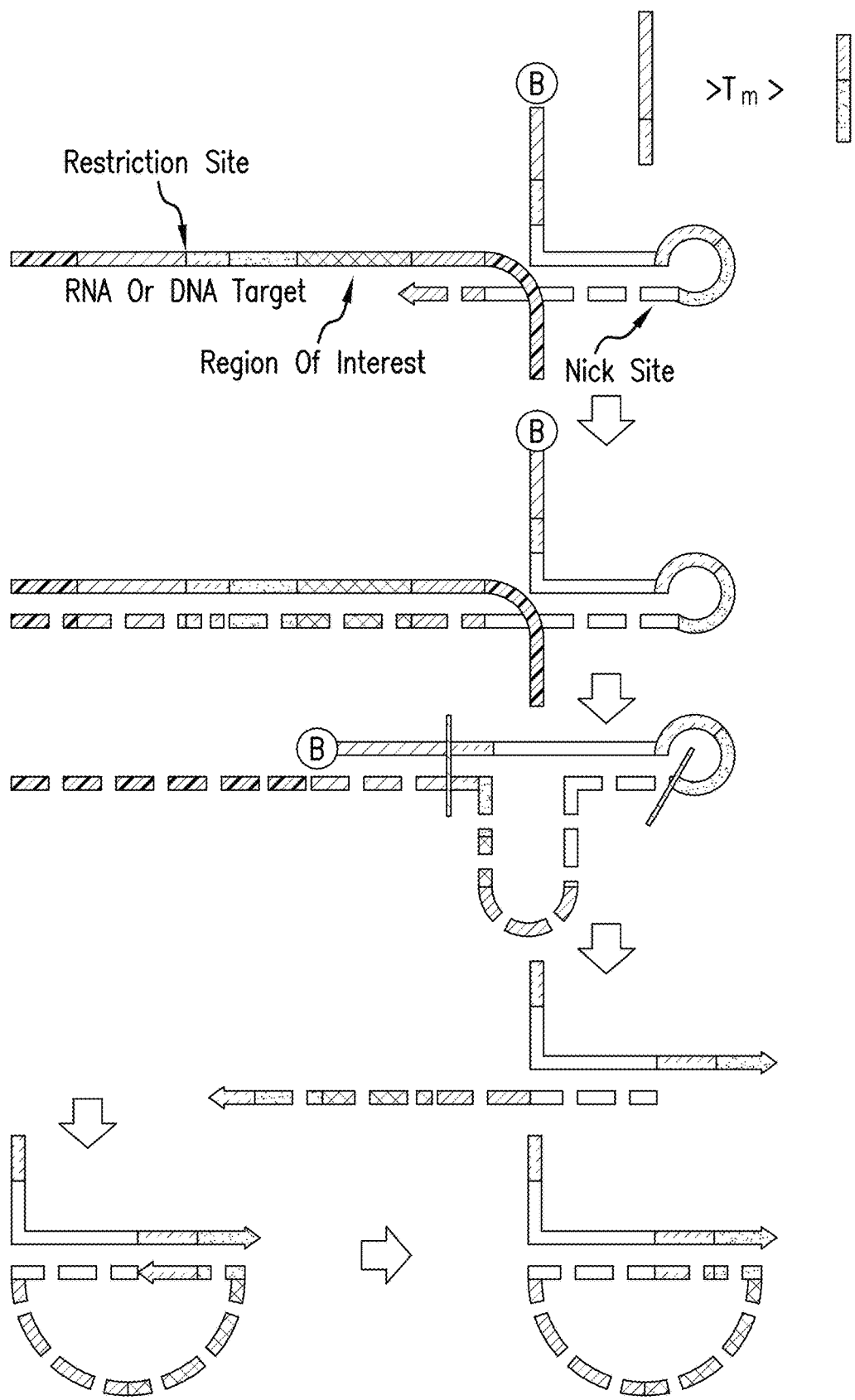
Figure 12:
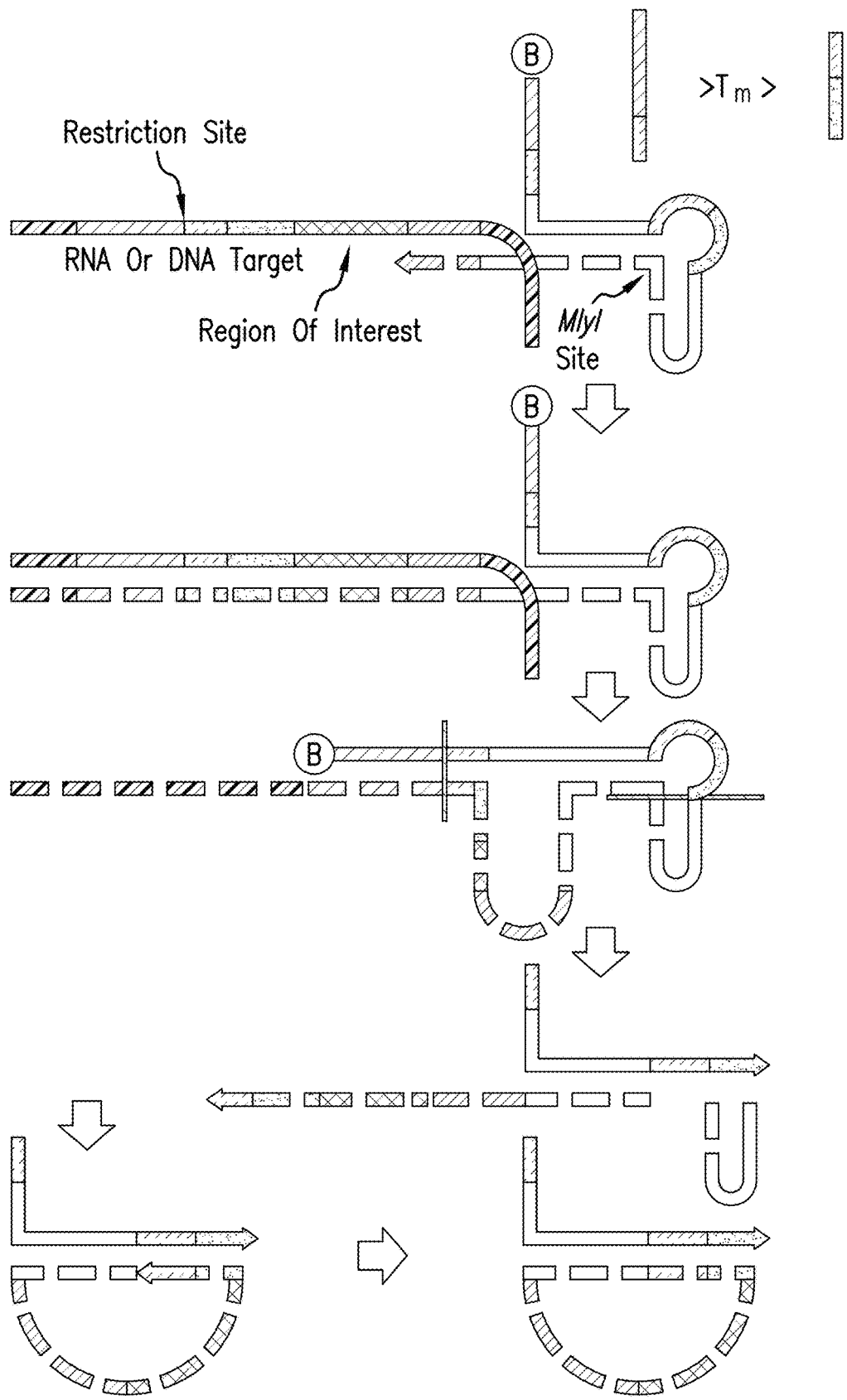

It will be apparent that any intervening sequence or spacer located between the second binding site and the second stem sequence of the stem-loop structure (i.e. at or towards the 5' end of the loop of the stem-loop structure) may result in there being a gap between the hybridised ends of the extended strand of the probe (the circularisable strand). This may occur, for example, if there is no additional sequence at the 3' end of the extended probe, 3' to the complement of the 5' flanking region, which is complementary to the intervening sequence or spacer. Such an additional sequence may e.g. result from cleavage of the cleavage site created by the third binding site; as noted above a sequence from the complementary binding site in the target complement in the extended probe for the third binding site may remain at the 3' end of the (extended) first strand of the probe following cleavage at the second cleavage site. If such an additional sequence is present, and this is complementary to a further (e.g. intervening) sequence in the loop 5' to the second binding site, there will be no gap. Accordingly the further or intervening sequence in the loop can be designed to be homologous (e.g. identical) to a sequence in the third binding site which is 3' to the site of cleavage and which remains at the 5' end of the second strand following cleavage. Such a configuration is depicted in FIGS. 11 and 12. However, alternatively, even in such an embodiment, the probe can be designed such that there is a gap.

As noted above, any such gap needs to be filled in order for ligation of the ends to take place. Such an intervening sequence or spacer may therefore be used to introduce a sequence into the circularised target molecule, for example a tag or detection sequence, e.g. a barcode or identificatory motif, or a binding site for a detection probe or primer. Indeed, any intervening sequence or spacer that forms part of the circularisable strand of the probe may be used to introduce a sequence into the circularised target molecule, for example a tag or detection sequence as described above. Tags such as barcodes/motifs or probe/primer binding sites may be designed with different needs/purposes, for example to introduce a universal or common sequence to enable different circularised target molecules in a multiplex setting to be processed together, e.g. to introduce a binding site for a universal or common amplification primer. This would enable different circularised target fragments to be amplified together, e.g. in a library amplification by PCR or RCA. Alternatively or additionally, a tag/barcode sequence may be used to "label" different circularised fragments so that they may readily be distinguished from one another (i.e. a "target" tag or marker), or to tag different samples etc., so that they may be pooled prior to common/universal amplification together (i.e. a "sample" tag or marker). Thus, in a multiplex setting different probes (i.e. probes for different target ROIs) may be provided with different tag sequences (e.g. different marker or detection sequences) and/or they may be provided with the same tag sequence(s), e.g. for the introduction of a common or universal sequence. Such tags may also be incorporated into the circularised strand by designing the stem sequences of the stem-loop structure to comprise a sequence that can be used as a tag or detection sequence. As noted above, in some embodiments, a tag may be incorporated in only into the first stem sequence.

As mentioned above, gap-filling may take place either by extending the hybridised 3' end of the target fragment, or more typically by hybridising one or more gap oligonucleotides into the gap. The gap oligonucleotide may be provided as part of the probe, e.g. pre-hybridised to the probe prior to contact with target nucleic acid, or it may be provided at the same or substantially the same time as contacting the probe with the target molecule, or it may be added at any time afterwards, e.g. after probe hybridisation, or after cleavage. The gap oligonucleotide may therefore be regarded as a detection, tag, barcode or ID motif oligonucleotide etc. As will be described in more detail below the gap oligonucleotide may comprise a region which is not complementary and does not hybridise to the intervening sequence or spacer such that when it is hybridised it contains a non-hybridised loop into which a tag, barcode, or ID motif sequence etc. may be incorporated.

In a further embodiment, the intervening or spacer sequences introduced into a probe of the invention may comprise a capture or "anchor" sequence element. Such elements may be combined with detection/ID elements between any of the sites. For example, capture elements may be present between the first target binding site and the stem-loop structure, within the stem or loop of the stem-loop structure, and/or 5' of the stem-loop structure (i.e. in a 5' single-stranded region). Such capture elements may be combined with a detection/ID element within the stem or loop of the stem-loop structure. In some embodiments such capture elements will be located between the first target binding site and the stem-loop structure. In an alternative embodiment, such capture elements will be located 5' of the stem-loop structure. In one embodiment of the invention where the probe comprises a third binding site 5' to the stem-loop structure separated from the 5' end of the stem by a spacer sequence, the spacer sequence may be a capture sequence element. In a further preferred embodiment the capture element may be located 5' of the third binding site or 5' of the stem sequence if the third binding site is not present. Such capture or anchor elements may be designed to hybridise to a cognate complementary binding site (i.e. a "bait" sequence), for example provided on a solid support or immobilised in situ (e.g. immobilised on the target nucleic acid as described above), to enable the probe and/or target fragment to be immobilised. This may thus enable the method to be carried out on a solid phase for one or more of the steps, for example the probe may be immobilised before or after hybridisation to the target molecule, or before or after the cleavage step. Advantageously, capture or anchor elements may be useful for in situ embodiments, e.g. for localised detection of a target nucleic acid molecule.

In some embodiments the capture or anchor element may be located within the third binding site. In other words the third binding site may comprise a capture sequence. In such a situation the capture/anchor sequence may be internal to the cleavage site (i.e. it may 3' of the cleavage site), such that it remains in the probe after cleavage (e.g. at the 5' end of the second strand). As noted above this may be useful when the capture or anchor sequence is used to localise the RCA product of RCA amplification of the circularised strand wherein the second strand acts as amplification primer. This is also illustrated in FIGS. 11 and 12, which show a capture sequence in the single-stranded 5' region of the probe, internal (3') to the cleavage site.

Thus the intervening or spacer sequence(s) may contain or carry an element by which the target fragment may be detected or separated, e.g. identified or amplified or captured. By "contains or carries" is meant that such an element may be contained within the nucleotide sequence of the oligonucleotide, e.g. a sequence tag (e.g. which can be used to identify a target fragment) or a probe or primer binding site or other nucleic acid-based affinity-binding site (for example a binding site for a hybridisation probe or for a DNA binding protein etc., which binding site may be viewed as a capture or detection element depending on the nature of the probe or affinity binding element, or a binding site for a sequencing primer, which sequencing primer binding site may accordingly be viewed as a detection element, or for an amplification primer, which amplification primer binding site may accordingly be viewed as an amplification element), may be contained within the nucleotide sequence of the oligonucleotide. Alternatively it may be attached or conjugated or in any way linked or coupled to or associated with the intervening sequence or spacer. For example, it may be a functional moiety (e.g. a chemical group or a molecule) which is attached etc. to the oligonucleotide, such as an immobilisation moiety or a detection moiety (e.g. a reporter or a label). An immobilisation moiety may for example be an affinity binding moiety or group, e.g. one member of an affinity binding pair (i.e. an affinity ligand e.g. biotin or a hapten), which is attached or conjugated etc. to said oligonucleotide, and is capable of binding to the other member of the affinity binding pair (i.e. its cognate binding partner e.g. streptavidin or an antibody) for the purposes of capture or separation, e.g. when the cognate binding partner is attached to a solid phase.

Such an attached or conjugated moiety as described above (i.e. a functional moiety for capture and/or detection) need not necessarily be attached to an intervening sequence or spacer, but may be provided in (i.e. attached or conjugated to) a different part of the probe e.g. a binding site. In particular the functional moiety (e.g. an affinity ligand or binding partner) may be provided attached to the second strand of the probe, or a part of the probe which will form the second strand. In one embodiment the functional moiety may be attached at the 5' end of the probe (or of the second strand of the probe), for example it may be attached at or to the third binding site, and in particular to the 5' end of a probe having a single-stranded 5' region comprising a third binding site.

Such an arrangement may conveniently be used to remove unreacted probes, as is shown for example in FIGS. 11 and 12. It may be desirable to remove unreacted probes to reduce or prevent (e.g. minimise) background. For example unreacted probes if present may act to prime unwanted reactions, for example they may hybridise to and may prime extension on RCA products resulting from RCA amplification of the circularised extended strand (e.g. potentially resulting in hyperbranched reaction products).

To remove the unreacted probes an affinity binding partner or ligand, e.g. biotin, which is capable of binding to a cognate binding partner (e.g. streptavidin), is provided at the 5' end of the probe, in particular at the 5' end of a 5' single-stranded region comprising a third binding site. Thus, the affinity binding partner is 5' of the cleavage site created by the third binding site and may be removed, or detached, from the probe by cleavage at the third binding site. Accordingly, any probe which has not bound to the target molecule and which has not been extended and cleaved will retain the affinity group. A probe which has bound to target and been extended (i.e. a reacted probe) will be cleaved by cleavage at the second cleavage site (created by the third binding site) and accordingly will not retain the affinity group (in other words, the affinity group will be removed or lost from the reacted probe by the second cleavage). Thus, unreacted probes may be selectively separated from reacted probes by virtue of the affinity group which is retained only on the unreacted probes, but which is removed by cleavage in the reacted probes. Accordingly to separate unreacted probes (e.g. unbound probes in the sense of unbound to target) the probes may be separated by binding of the probes to the cognate affinity groups (e.g. streptavidin) which allow the cognate affinity group-bound probes to be separated from unreacted probes which have lost the affinity group. Conveniently, this may be achieved by providing the cognate affinity group on a solid support. Thus the affinity group (i.e. affinity binding partner or ligand) provided in the probe may be an immobilisable group i.e. an "immobilisation element", and in particular an immobilisable group which is capable of binding to a cognate affinity group provided on a solid support.

The step of removal of unreacted probes in this manner may be conducted in different ways, or at different times or points in the method. For example in one embodiment the unreacted probes may be removed by contacting with a cognate affinity group (e.g. on a solid support) after step (e), e.g. after cleavage and rearrangement of the probe, or after ligation to circularise the rearranged probe (e.g. after step (f)). Alternatively, it may be performed before step (e), such that both reacted and unreacted probes are bound to the cognate affinity groups (e.g. removed from solution by binding to the cognate affinity group on a solid support, or put more simply, the probes are bound to a solid support), and reacted probes are released from the cognate affinity group (e.g. released into solution, or released from the solid support) by cleavage of the extended probes at the second binding site in step (e).

In certain embodiments, such a capture moiety for removal of unreacted probes may be combined with a further, separate, anchor sequence for localisation of the amplification product, as described above. For example such a capture moiety and anchor sequence may be provided in the third binding site, wherein the anchor sequence is internal to the cleavage site provided by the third binding site (e.g. internal, or 3' to the cleavage site). More particularly, the third binding site may be in a 5' single-stranded region of the probe, e.g. as depicted in FIGS. 11 and 12.

As discussed above, an affinity group provided in the probe in this manner may e.g. be biotin, or any ligand capable of binding to a cognate affinity group, for example a hapten for an antibody etc.

A detection element may, for example, include an identification element, namely an element which allows or permits identification, for example, of a particular target ROI, or of a sample (e.g. when samples are pooled), or indeed of an individual target nucleic acid molecule in the sample. Such an identification element or ID tag or motif may simply be a sequence tag or motif, e.g. a particular or unique nucleotide sequence. This may thus be viewed as a sequence marker. The design of such sequence tags/motifs or markers is well known in the art. For example barcode sequences/motifs for use as tags are widely used and known in the art, for tagging samples or molecules etc. Degenerate sequences may be used as the basis for such tags and again the use of degenerate sequence motifs in this way is known in the art.

A number of different tags may be included to mark or tag different aspects of the target nucleic acid molecule or ROI. For example a tag, e.g. a barcode motif, may be included as a sample tag, together with a tag for the particular target ROI for which the probe is designed to be selective. Advantageously, a "molecular" tag may be used to mark or tag (i.e. identify) an individual molecule in the sample, e.g. the initial complement of an original molecule of the sample. This can be particularly advantageous in the context of sequencing, and especially in NGS technologies, where it can be valuable to track sequence reads back to an original, molecule which is amplified for sequencing.

Thus, it will be seen that various types of identification element or tag may be used singly or in combination.

Sequence tag or barcodes can be in the region of 20 nucleotides, for example from 7 to 30 nucleotides, e.g. 7, 8, 9, 10, 11, 12, 13, 14, 15, 16, 17, 18, 19, 20, 21, 22, 23, 24, 25, 26, 27, 28, 29 or 30 nucleotides, in length. Sequence tags or barcodes can be randomly generated, for example a set of sequence tags may comprise tags with all possible sequence combinations of the total number of nucleotides in the tag sequence.

Thus, the probe may contain a sample sequence tag, e.g. a feature which allows a probe used in the method of the invention as performed on a particular sample to be distinguished from a probe used in the method as performed on a different sample and which thereby allows identification of the sample from which a given target fragment (i.e. the complement of the target fragment) has been circularised.

The sample tag allows identification of the sample from which a particular target fragment and hence ROI originates. The samples may, for example, correspond to patient samples. If the method is performed in multiplex for detection of a number of different target ROIs from different samples, then separate sample and "target" tags may be included in each probe. Utilising the methods and probes of the present invention, this feature advantageously allows the pooling of samples, for example after contact with the probes and ligation of the probes to tag each sample, different samples may be pooled.

A detection element may, as noted above, also be a binding site contained in the oligonucleotide sequence (e.g. a binding site for a detection probe or moiety or for a primer to be used in a detection reaction, e.g. a sequencing primer) or it may be a detection moiety which is carried in any way by the oligonucleotide, e.g. a reporter group or moiety or a label, which may be directly or indirectly signal-giving. For example it may be a visualisable label, such as a coloured or fluorescent or particulate label, or a moiety which contributes to or takes part in a signal-giving reaction, e.g. an affinity binding partner or ligand or a substrate or co-factor for an enzyme.

A capture element may be any element for the amplification and/or capture of the circularised target fragment. An "amplification element" may be used to amplify the circularised target fragment (i.e. the circularised strand of the probe containing the complement of the target ROI). Typically it will be an amplification primer binding site. It may also be a binding site for one of a number or set (e.g. pair) of amplification primers, for example to allow exponential amplification, e.g. a PCR primer or a primer for a PCR-based procedure. The primer binding site may also be used for the binding of a sequencing primer.

A "capture element" may be any moiety carried by (e.g. attached or conjugated to etc.) the probe, or any feature of the sequence of the probe (e.g. a binding site, spacer sequence), which may potentially be used selectively to attach an extended probe (e.g. a circularised probe containing a complement of the target fragment) to a solid phase or support, including for example a particle such as a bead, and/or in situ. Hence, a capture element may be viewed as an "immobilisation element". The extended probe, e.g. the circularised strand of the probe generated by the method of the invention, may be immobilised or captured directly, e.g. via a capture element that hybridises to a sequence in the circularised strand, such as an immobilised primer or the ligation template strand which may be immobilised, i.e. in some embodiments the ligation template strand contains a capture element. Alternatively, the extended probe may be immobilised or captured indirectly, e.g. via a capture element that binds to a binding site in the ligation template strand, which is bound to the circularised strand. Numerous examples of such elements are known in the art and include, e.g., an affinity binding partner, e.g. biotin or a hapten, capable of binding to its binding partner, i.e. a cognate binding partner, e.g. streptavidin or avidin, or an antibody, provided on the solid phase or support. A capture element may be a nucleotide sequence with complementarity to a corresponding "binding" or "receptor" oligonucleotide or nucleotide sequence provided on the solid support, or may be a functional moiety (e.g. a chemical group or a molecule) which is attached etc. to the oligonucleotide, e.g. biotin or a hapten. Said interaction between the probe and a solid phase (e.g. via an immobilised binding or receptor oligonucleotide, or binding partner e.g. streptavidin or an antibody) may particularly be mediated by click chemistry (Kolb H C et al, Angew Chem Int Ed Engl. 2001 Jun. 1; 40(11):2004-2021).

As discussed above, as well as a capture element for capture of an extended probe, the probe may alternatively or additionally be provided with a (separate) capture element for capture and selective removal of unreacted probes.

The solid phase may be any of the well-known supports or matrices which are currently widely used or proposed for immobilisation, separation etc. These may take the form of particles (e.g. beads which may be magnetic, paramagnetic or non-magnetic), sheets, gels, filters, membranes, fibres, capillaries, or microtitre strips, tubes, plates or wells etc. The support may be made of glass, silica, latex or a polymeric material. Suitable are materials presenting a high surface area for binding of the analyte. Such supports may have an irregular surface and may be, e.g. porous or particulate, e.g. particles, fibres, webs, sinters or sieves. Particulate materials, e.g. beads are useful due to their greater binding capacity, particularly polymeric beads. Conveniently, a particulate solid support used according to the invention will comprise spherical beads. The size of the beads is not critical, but they may, e.g. be of the order of diameter of at least 1 and preferably at least 2 µm, and have a maximum diameter of preferably not more than 10, and e.g. not more than 6 µm. Monodisperse particles, that is those which are substantially uniform in size (e.g. size having a diameter standard deviation of less than 5%) have the advantage that they provide very uniform reproducibility of reaction. For example, to aid manipulation and separation, magnetic or paramagnetic beads are advantageous. Other solid phases include very small particles which can efficiently contact a high proportion of the immobilisable oligonucleotides. Such particles may further be useful by retarding the movement of particle-attached target fragments (i.e. target fragment complements) through a gel, allowing separation from free, non-particle-attached (non-target) fragments. Alternatively, also preferred is the use of a chromatographic matrix modified with groups that can be reacted covalently or non-covalently with capture elements in the probe.

As described above, the "gap" oligonucleotide which may be hybridised to the intervening sequence or spacer located between the second binding site and the second stem sequence of the stem-loop structure contains regions of complementarity to the intervening sequence or spacer, which regions may be separated by a sequence that is not complementary to the intervening sequence or spacer. Hence, the two regions of complementarity to the intervening sequence or spacer are at the ends of the complementary oligonucleotide, and flank a region within the oligonucleotide that is not complementary to the intervening sequence. Consequently, the sequence that is not complementary to the intervening sequence forms a loop or bulge and may comprise a tag, for example a barcode sequence etc., e.g. for identifying a selected target ROI.

In one embodiment of the present invention, the probe of the invention comprises a hairpin structure, i.e. a stem-loop structure, which comprises the second binding site. It is necessary to unfold the probe to open the loop, which may be performed before, during or after the extension step, before the second binding site can become accessible and template the ligation of the extended strand of the probe. The loop of the hairpin may therefore contain a binding site such that it is not available for hybridisation to its complementary binding site at or towards the 3' end of the extended strand (the circularisable strand) of the probe until the probe has been opened to release the second binding site.

A hairpin structure may also be known as a hairpin-loop or a stem-loop and these terms are used interchangeably herein. A hairpin is an intra-molecular base-pairing pattern that can occur in a single-stranded DNA or RNA molecule. A hairpin occurs when two regions of the same strand, usually complementary in nucleotide sequence when read in opposite directions, base-pair to form a double helix (a duplex) that ends in an unpaired, i.e. single-stranded, loop. The resulting structure can be described as lollipop-shaped.

The hairpin may be unfolded or "opened" by cleavage, e.g. in or near the loop, such as in the stem or loop of the stem-loop structure, wherein cleavage occurs 3' of the second binding site. As described above, the double stranded element of the probe, i.e. the stem of the stem-loop structure, is retained (at least in part) in the opened structure, whereby the first strand comprises the extended strand (i.e. the circularisable strand containing the complement of the target nucleic acid molecule and any optional intervening sequences or spacers), and the second strand of the opened hairpin (the ligation template strand) comprises the second binding site and any optional additional intervening sequences or spacer elements, when the stem or loop of the hairpin structure is cleaved. Thus, it will be evident that the cleavage site must be located in the probe such that when cleavage occurs, the hairpin is able to open whilst retaining a sufficient amount of stem structure that allows the extended (circularisable) strand to maintain its interaction with the ligation template strand under the conditions of the method, i.e. the location of the cleavage site must enable the hairpin to open and the probe to form a partially double-stranded molecule. A discussion of the techniques which may be employed to unfold a hairpin structure is provided in WO2012/152942, which is incorporated herein by reference in its entirety. As discussed below, cleavage is preferably enzymatic cleavage.

In some embodiments, the stem of the hairpin (stem-loop) structure comprises a cleavage site (see e.g. probes ExCirc_2 (SEQ ID NO:2), ExCirc_hTert (SEQ ID NO:7) and ExCirc_miR208 (SEQ ID NO:11) in Examples 1-3, respectively). Preferably, the cleavage site (e.g. the cleavage recognition site) in the stem of the hairpin is located at or towards the 5' end of the first strand of the stem sequence (the first stem sequence) and advantageously cleavage will occur at or towards the 5' end of the first strand of the stem sequence. Thus, in some embodiments, the cleavage site in the stem is adjacent to the loop. Hence, following cleavage, only part or a portion of the original stem sequence will be retained in a duplex, i.e. a sufficient amount of stem sequence must be retained in a duplex to enable the extended (circularisable) strand and the ligation template strand to form a partially double stranded molecule. In embodiments where the cleavage site is in the stem of the stem-loop structure, cleavage must occur only in a single strand of the stem, i.e. the first stand of the stem (the part of the stem that will form part of the circularisable strand). Thus, in some embodiments, the cleavage site in the stem is a nickase cleavage site, i.e. a cleavage site that is recognised by a nickase enzyme as discussed below, wherein the nickase cleaves the first stem sequence of the stem-loop structure.

In some embodiments where the cleavage site is in the stem of the stem-loop structure, cleavage of the stem (the first stem sequence) may not directly or immediately cause the hairpin to unfold, e.g. the duplex may be stable under the conditions of the reaction even upon cleavage of a single strand. However, the hairpin may unfold upon the intramolecular rearrangement of the probe, wherein the interaction between the 3' end of the extended strand and the second binding site is more stable (i.e. thermodynamically more favourable) than the interaction of the stem sequences at the "loop end" of the stem. In other words, the 3' end of the extended strand may be seen to displace the 3' end of the cleaved first stem strand.

In some embodiments, the loop of the hairpin (stem-loop) structure comprises a cleavage site. In preferred embodiments, the cleavage site in the loop is adjacent to the stem. In some embodiments, the loop of the hairpin structure may comprise a region of intramolecular complementarity such that it is able to form a duplex within the loop, i.e. the loop contains a double stranded region (a duplex) that forms a protrusion from the loop and is therefore distinct from the "stem" of the hairpin structure. The internal duplex of the loop may comprise a cleavage site, e.g. a restriction endonuclease recognition site, wherein cleavage of the duplex within the loop results in unfolding of the hairpin structure (see e.g. probe ExCirc_1 in Example 1 (SEQ ID NO:1)). Thus, in some embodiments, an intervening sequence or spacer located 3' of the second binding site (more particularly between the first stem sequence and the second binding site) may contain a region of intramolecular complementarity. In such embodiments having a cleavage site in an internal duplex of the loop, both strands of the internal duplex may be cleaved.

In some embodiments the internal duplex in the loop contains a M/yl cleavage site. The cleavage site, e.g. M/yl cleavage site, may be positioned to allow cleavage in such a manner that the internal loop is removed. This is depicted in FIG. 12. The cleavage may leave the 5' end of the extended, first, strand, which is released by the cleavage, hybridised in the stem.

"Cleavage" is defined broadly herein to include any means of breaking or disrupting a nucleotide chain (i.e. a nucleotide sequence). Cleavage may thus involve breaking a covalent bond. Typically cleavage will involve cleavage of nucleotide chain (i.e. strand cleavage or strand scission), for example by cleavage of a phosphodiester bond. Cleavage of the cleavage site in the stem-loop structure of the probe, e.g. in the stem or loop, may be achieved by any convenient means but is preferably enzymatic cleavage, as described below.

For instance, the hairpin structure may comprise or may be engineered or modified to comprise a restriction endonuclease recognition sequence. In a preferred embodiment, e.g. where the hairpin structure comprises a restriction endonuclease recognition site, the restriction endonuclease will cleave only a single strand of the duplex portion of the hairpin structure. For example, this may be achieved by hybridising an oligonucleotide (termed herein a "restriction oligonucleotide") to the single-stranded loop of the hairpin structure to comprise a duplex within the loop. At least part of the formed duplex will comprise a restriction endonuclease recognition site, which can be cleaved resulting in unfolding of the hairpin structure. Any suitable restriction endonuclease may be used to unfold the hairpin structure. In other embodiments, cleavage may comprise breaking covalent bonds within one or more nucleotides in a nucleic acid sequence. In some embodiments a cleavage site may be created by incorporating one or more uracil residues into the stem and/or loop sequence. In a particularly preferred embodiment, the hairpin structure can be unfolded by treatment with a uracil-DNA glycosylase (UNG) enzyme in combination with an endonuclease enzyme capable of recognising apurinic/apyrimidinic (AP) sites of dsDNA, e.g. endonuclease IV.

In a further preferred embodiment the hairpin structure may be cleaved, and thereby unfolded, using a nickase enzyme, which cleaves only one strand in the duplex of the hairpin structure. Nickases are endonucleases which cleave only a single strand of a DNA duplex. As described above, a cleavage site may be introduced in the single-stranded loop of the hairpin structure, e.g. by annealing (hybridising) and oligonucleotide to said loop. In some embodiments, the stem of the stem-loop structure comprises a nickase cleavage site.

Some nickases introduce single-stranded nicks only at particular sites on a DNA molecule, by binding to and recognizing a particular nucleotide recognition sequence. A number of naturally-occurring nickases have been discovered, of which at present the sequence recognition properties have been determined for at least four. Nickases are described in U.S. Pat. No. 6,867,028, which is herein incorporated by reference in its entirety and any suitable nickase may be used in the methods of the invention.

In some preferred embodiments that utilise a nickase enzyme, the nickase enzyme is removed from the assay or inactivated following unfolding of the probe to prevent unwanted cleavage of ligation products.

As discussed above, the probe for use in the methods of the invention comprises at least a first target binding site which is complementary to the 3' flanking sequence flanking the target ROI in the target nucleic acid molecule. "Complementarity" as used herein refers to functional complementarity, i.e. capable of mediating hybridisation, and need not refer to 100% complementarity between two nucleic acid molecules. Hybridisation according the present invention includes the formation of a duplex between nucleotide sequences which are sufficiently complementary to each other, whether by Watson-Crick type base pairing or by any analogous base pairing. The hybridisation is a productive hybridisation, that is a hybridisation which is stable enough or strong enough for the probe to be able to perform its function, e.g. for probe/target molecule hybrid to be separated from the sample, or for the cleavage sites created to be cleaved, and for the target fragment to be able to be circularised by ligation.

Thus, complementary nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

As discussed above, the probe comprises at least one binding site which is homologous to a region of the target nucleic acid molecule, and is capable of hybridising to the complement of such sequences, as described above. It is apparent that the sequence of a binding site of the probe with homology to a region of the target nucleic acid molecule does not need to be identical to a sequence of the target nucleic acid molecule in order to be capable of hybridising to its complement. Thus, a binding site may be viewed as homologous to a corresponding region in the target molecule when it is effectively identical. For example, a binding site may share at least 75% sequence identity to a region of the target nucleic acid molecule, or at least 80%, 85% or 90% identity. In a preferred embodiment a binding site has at least 95% identity to a region of the target nucleic acid molecule, such as 96, 97, 98 or 99% identity. In a further embodiment, a binding site has 100% identity to a region of the target nucleic acid molecule. In particular, the sequence of the second binding site may not be identical to the 5' flanking sequence, as long as it is capable of binding to the complement of the 5' flanking sequence. Thus in one embodiment a single probe may be able to select a target ROI from a plurality of target molecules, wherein the target molecules have a degree of sequence variability in the 5' flanking sequence flanking the target ROI, or wherein the sequence of the 5' flanking sequence is not fully known.

It would be a matter of routine to the person skilled in this art appropriately to design the target binding sites in the probe, e.g. taking into account length of the sites, G/C content and Tm etc. Typically the target binding site is at least 5 nucleotides long, more typically at least 6, 7, 8, 9, 10, 11, 12, 13, 14, 15, 16, 17, 18, 19, 20, 30, 40 or 50 nucleotides in length or any integer between or up to or above any of these.

In order for the extended strand to undergo direct or indirect ligation in part (f) of the method of the present invention, the 3' end of the extended strand (i.e. the circularisable strand containing the complement of the 5' flanking sequence) must be capable of hybridising to the second binding site. In certain embodiments of the present invention when the 5' flanking sequence flanking the target ROI is located at the 5' end of the target nucleic acid molecule, for instance when the target nucleic acid molecule is a miRNA or a transcript, the 3' end of the extended probe can hybridise to its complementary sequence in the second binding site completely.

However, in some embodiments the 5' flanking sequence flanking the target ROI may be internal to the 5' end of the target nucleic acid molecule, and it may thus be necessary to remove the region of the extended strand of the probe that is complementary to the region immediately 5' to the 5' flanking sequence (i.e. the region at the 3' end of the extended probe that is not complementary to the second binding site) before ligation may take place. This sequence may be removed by any suitable means, e.g. degradation using a 3' exonuclease.

Thus, in embodiments when the 5' flanking sequence is internal to the 5' end of the target molecule, step (e) of the method described above may comprise:

(i) cleaving the extended probe at the cleavage site in the stem-loop structure of the probe to release a 3' end of the probe comprising the second binding site, thereby generating a partially double-stranded construct comprising a first extended strand comprising the target complement and a second strand hybridised to the first strand in the stem and comprising the released 3' end; and (ii) allowing the second binding site in the released 3' end in the second strand to hybridise to its complementary binding site in the target complement in the first strand, wherein the additional sequence at the 3' end of the first strand does not hybridise and forms a protruding single stranded end;

(iii) cleaving the protruding single stranded end to leave a 3' end of the first strand which is hybridised to the second binding site in the second strand, thereby to bring the 5' and 3' ends of the first, extended, strand into juxtaposition for ligation, directly or indirectly, to each other, using the second binding site as ligation template.

As discussed above, the probe of the present invention may comprise an additional sequence homologous to a sequence immediately 5' to the 5' flanking sequence in the target molecule and comprising a sequence capable of forming a second cleavage site when hybridised to the extended probe. After extension of the probe molecule the extended probe can undergo an intramolecular hybridisation wherein the third binding site hybridises to its complementary binding site in the target complement, thereby generating a second cleavage site. The cleavage site is positioned in such a way that the sequence 3' to the complement of the 5' flanking sequence is removed after cleavage. As discussed above, the cleavage site may be positioned at the 3' end of the third binding site, or may be positioned within the third binding site (i.e. in a position which would not remove the entirety of the sequence complementary to the third binding site). Where this is the case the loop of the stem-loop structure may comprise a sequence complementary to the sequence from the complementary binding site in the target complement for the third binding site, which sequence remains at the 3' end of the first strand of the probe following cleavage at the second cleavage site.

Cleavage of the second cleavage site, e.g. produced by the interaction of the third binding site and it complementary region at or towards the 3' end of the extended probe, may be achieved by any convenient means but is preferably enzymatic cleavage, as described above. Cleavage may also take place before, simultaneously with, or after cleavage of the loop of the stem-loop structure.

Thus, in a preferred embodiment, the second cleavage site created by the intramolecular rearrangement of the extended probe (following removal of the target nucleic acid) represents a cleavage recognition site, e.g. a sequence that is recognised by one or more enzymes capable of cleaving nucleic acid molecules. The cleavage sites in the rearranged probe may either be the same or different.

Any suitable cleavage enzyme may be used to cleave the second cleavage site to release the 3' end of the first strand (the circularisable strand) comprising the complementary binding site for the second binding site.

In a preferred embodiment, the second cleavage site is a restriction site. In this preferred embodiment the restriction endonuclease will cleave both strands of the second cleavage site. The endonuclease may alternatively cleave a single strand, namely the extended strand (the circularisable strand). In a further preferred embodiment the second cleavage site is a nickase recognition sequence that templates the single-stranded cutting of the extended strand of the second double-stranded region. Thus enzymatic cleavage at a specific site within the extended probe strand may release the 3' end of the extended strand, which is complementary to second binding site. In a further embodiment of the present invention where a plurality of different target ROIs are selected by a plurality of different probes, either a single cleavage enzyme, or a plurality of different cleavage enzymes may be used.

In an alternative embodiment where the 5' flanking sequence is internal to the 5' end of the target nucleic acid, the region of extended probe complementary to the second binding site may hybridise to the second binding site to form a circular nucleic acid construct with a protruding 3' end (i.e. the sequence complementary to the sequence 5' of the 5' flanking sequence). An enzyme with 3'→5' exonuclease activity (such as a polymerase with 3'→5' exonuclease "proofreading" activity) may be used to degrade the protruding 3' end, thereby releasing the 3' end of the extended probe.

In embodiments of the present invention in which the probe is provided as a partially double-stranded construct comprising a first strand comprising a single-stranded 3' end region comprising the first binding site at the 3' end thereof and a second strand hybridised at the 5' end of said first strand and comprising a single-stranded 3' end region comprising the second binding site (or wherein a stem-loop probe is cleaved before it is contacted with the target molecule, it will be apparent that no cleavage is required following extension of the probe in order to release second binding site. In such an embodiment, the second binding site (i.e. the 3' end of the second strand) is accessible for hybridisation to its complementary sequence in the target complement (i.e. the complement of the 5' flanking sequence) once extension has taken place.

Thus, in certain embodiments of the present invention in which the 5' flanking sequence lies at the 5' end of the target nucleic acid molecule, step (e) comprises allowing the second binding site in the second strand to hybridise to its complementary binding site in the target complement in the extended first strand, thereby bringing the 5' and 3' ends of the first, extended, strand into juxtaposition for ligation, directly or indirectly to each other, using the second strand as a ligation template.

In further embodiments of the present invention, wherein the 5' flanking sequence is internal to the 5' end of the target nucleic acid molecule, it may necessary to remove the region of the extended strand of the probe that is complementary to the region immediately 5' to the 5' flanking sequence (i.e. the region at the 3' end of the extended probe that is not complementary to the second binding site) before ligation may take place. This sequence may be removed by any suitable means.

Removal of the region of the extended strand that is complementary to the region immediately 5' to the 5' flanking sequence may be performed by generating a cleavage site, e.g. by hybridising a complementary nucleic acid molecule to a cleavage sequence immediately 5' to the 5' flanking sequence. This may be provided as a separate nucleic acid molecule (i.e. a molecule homologous to a portion of the target nucleic acid molecule), or may be provided as a further sequence within the probe.

Thus in one aspect, the second strand of the probe may further comprise a third binding site which is homologous to a cleavage sequence immediately 5' to the 5' flanking sequence in the target molecule and is capable of hybridising to a complement of said cleavage sequence in the additional sequence in the target complement in the extended first strand, which is 3' to the complement of the 5' flanking sequence. The third binding site may be located in the single-stranded 3' region of the second strand 3' to the second binding site, or may be located in a further single-stranded 5' region of the second strand, i.e. 5' to the double-stranded region.

Step (e) of the method of the invention may therefore comprise the following steps:
i) allowing the extended probe to undergo an intramolecular hybridisation wherein the third binding site hybridises to its complementary binding site in the target complement, thereby generating a cleavage site;
ii) cleaving the hybridised probe at the cleavage site, thereby generating a released 3' end of the first extended strand;
iii) allowing the second binding site to hybridise to its complementary binding site in the target complement in the first strand, thereby bringing the 5' end and the released 3' end of the first, extended, strand into juxtaposition for ligation directly or indirectly to each other, using the second binding site as a ligation template.

In a further aspect, the probe may comprise 3' to the second binding site a further probe sequence that is homologous to the 3' flanking sequence of the target nucleic acid molecule, and thus that is complementary to the first binding site. Such a sequence may hybridise to the first binding site (or a part thereof) following extension of the probe, and may be used to template the circularisation of the extended probe in combination with the second binding site (which hybridise to the 3' flanking sequence, and 5' flanking sequence, respectively). The further probe sequence may overlap partially with the second binding site, or in other words, the second binding site may comprise a region of homology to the 5' flanking sequence (which may be a part of the ROI), and a region of homology to the 3' flanking sequence.

Such a probe may be of particular utility where the second binding site is homologous to the ROI (or the 5' end of the ROI), and is capable of hybridising to a complement of the ROI. The second binding site and the further probe sequence may thus form an extended region of complementarity to the 3' end of the extended probe (the target complement). However, the above probe may also be of utility, however, where the second binding site is homologous to the 5' flanking sequence in the target nucleic acid molecule (i.e. where the second binding site is not homologous to the ROI). The complements of the 3' and 5' flanking sequences may hybridise to the second binding site and the further probe sequence, with the sequence between the 3' and 5' flanking regions (i.e. the ROI) forming a loop.

Thus, in a further embodiment of the present invention, the probe may comprise a further probe sequence which lies 3' of the second binding site and is homologous to the 3' flanking sequence and complementary to the first binding site, wherein when said probe comprises a stem-loop structure said further probe sequence is located in the loop, or when said probe is a double-stranded construct the further probe sequence is located at the 3' end of the second strand; and wherein in step (e) of the method the invention the further probe sequence hybridises to the first binding site and acts as a ligation template together with the second binding site.

As discussed above, the second binding site templates the ligation and thereby circularisation of the extended strand (the circularisable strand), whereby the second target binding site may hybridise to its complementary binding site in the extended strand, thereby to bring the ends of the extended strand into juxtaposition for ligation.

As discussed above, the ends of the extended strand (the circularisable strand) may be positioned directly adjacent to each other, and thus ligation may take place directly between the ends of the extended strand. Alternatively, the ends of the extended strand may not be positioned directly adjacent to each other, i.e. where there is an intervening sequence or spacer between the 5' end of the second binding site and the second stem sequence of the probe. In such instances, the ends of the extended strand may be ligated indirectly, e.g. via one or more gap oligonucleotides or after the "gap-fill" extension of the 3' end of the oligonucleotide. The gap oligonucleotide will be complementary to the intervening sequence between the second binding site and the second stem sequence, and may either be added to the sample separately to the probe, or may be hybridised to the probe prior to the selection of the target ROI.

The ligation step may be performed by procedures well known in the art. Enzymes appropriate for the ligation step are known in the art and include, e.g. Tth DNA ligase, Taq DNA ligase, *Thermococcus* sp. (strain 9°N) DNA ligase (9° N™ DNA ligase, New England Biolabs), Ampligase™ (Epicentre Biotechnologies) and T4 DNA ligase.

A target ROI (i.e. the complement of the target ROI) circularised according to the method herein may be directly separated, analysed or detected, or may instead first be amplified. Indeed it may be detected by means of the amplification. Amplification of the target ROI may be performed by any suitable method for amplifying nucleic acids and in particular circular nucleic acids. Amplification may be linear or exponential, as desired, where representative amplification protocols of interest include, but are not limited to: polymerase chain reaction (PCR); isothermal amplification, rolling-circle amplification (RCA), and their well-known variants, such as hyperbranched RCA, etc. Other nucleic acid amplification methods may include Loop mediated isothermal amplification (LAMP), SMart Amplification Process (SMAP), Nucleic acid sequence based amplification (NASBA), or ligase chain reaction (LCR). Where the detection step includes an amplification, the amplification product may be detected, to detect the target ROI.

Amplification methods based on RCA represent one preferred embodiment and in a particular aspect the amplification may involve a second round of RCA, for example a superRCA (sRCA) reaction as described in WO2014/076209, herein incorporated by reference. In such a sRCA reaction a secondary RCA reaction is performed using a further RCA template circle and the RCA is primed by a primer which is hybridised to the primary RCA product (here the amplicon of a first RCA step using the circularised probe containing a complement of the target fragment as template). The primer is provided in such a way that it remains hybridised to the first RCA product throughout the secondary RCA, such that the secondary RCA product is localised to the primary RCA product. In a further preferred embodiment of a localised super RCA reaction, the secondary RCA reaction may be templated by a padlock probe which hybridises to the primary RCA product and is ligated to form a circle which is then subjected to a secondary RCA reaction (a so-called "Padlock sRCA" which is described in our co-pending GB patent application No. 1320145.4).

In such sRCA reactions the secondary RCA product is unrelated to the primary RCA template, i.e. the first circle, which in this case is the circularised target fragment (more particularly the circularised target fragment complement). Thus a sRCA is used as a means of signal amplification, e.g. in a detection method, rather than as means of amplifying the target ROI in, e.g. a preparative method. For such purposes, a circle-to-circle RCA reaction (as described in WO/2003/012119) may be used to enhance the amount of product generated by the RCA, which is essentially a linear amplification process, or a hyperbranched RCA.

Alternatively an exponential amplification reaction such as PCR may be used. Amplification of the circularised target fragment (i.e. the circularised target fragment complement) by PCR represents another preferred embodiment. As discussed above, binding sites for PCR primers may conveniently be provided by a gap oligonucleotide incorporated into the circularised molecule. Alternatively, amplification primers may be designed to bind elsewhere in the target fragment. In multiplex embodiments universal or common PCR primer binding sites may be introduced and used to amplify different circularised target fragments in parallel using a single primer pair. Such use of a single primer pair has been demonstrated in other contexts and applications, e.g. for Selector probes as disclosed in U.S. Pat. No. 7,883,849 as discussed above.

It will be apparent that the portions of the probe that template the ligation of the target ROI (i.e. the second binding site and second stem sequence) can remain bound to the circularisable strand (e.g. to the complement of the target ROI) after ligation and circularisation have taken place. Thus in one embodiment of the present invention, the second binding site of the probe may act as a primer to initiate rolling circle amplification. In an alternative embodiment, a primer may be added to the sample to initiate rolling circle amplification.

Although amplification of the circularised target fragment is convenient and in many applications of the method it may be preferred, it is possible also to separate the circularised target fragment (i.e. the circularised strand containing the complement of the target ROI) in other ways, for example by digesting any linear molecules present using an exonuclease, thereby to enrich for circular nucleic acids, or by other nucleic acid separation or fractionation procedures known in the art.

It is further apparent that the method outlined above can be used to generate a circularised molecule comprising the complement of the target ROI in solution. Thus the method may be performed in a homogenous format. However in an alternative embodiment the probe may be immobilised on a solid support prior to, or after, hybridisation to the target nucleic acid molecule, or indeed at any stage of the method. Means for immobilising the probe or target fragment may be introduced by way of an intervening sequence or spacer element in the probe, as discussed above.

The intervening sequence or spacer element may be between the first target binding site and the stem-loop structure, 5' of the stem-loop structure, or located within the loop of the stem-loop structure, between the 5' end of the second binding site and the second stem sequence, and may be hybridised to a complementary nucleic acid molecule, thereby forming a partially double-stranded nucleic acid probe. In a first embodiment the intervening sequence or spacer element may be attached to a solid support. In a second embodiment the complementary nucleic acid molecule can be attached to a solid support. In some embodiments, the second stem sequence may be attached directly or indirectly to a solid support. In a further embodiment, the intervening sequence or spacer element may be 5' of a third binding site, and may be hybridised to a complementary nucleic acid molecule, thereby forming a partially double-stranded nucleic acid probe, and either the probe or its complementary nucleic acid molecule can be attached to a solid support.

In some embodiments one or more spacer sequences may be located 3' of the stem of the stem-loop structure.

By analogy, where the probe is partially double-stranded, an intervening sequence or spacer element may be between the first target binding site and the double-stranded region of the probe, in the second strand 5' of the double-stranded region, or located in the first strand 5' of the double-stranded region, and may be hybridised to a complementary nucleic acid molecule, thereby forming a partially double-stranded nucleic acid probe comprising more than one double-stranded region. The intervening sequence or its complement may similarly be attached to a solid support, as discussed above.

In a further specific embodiment, the present invention also provides a method of selecting a target region of interest (ROI) in a target nucleic acid molecule, wherein said ROI lies at the 5' end of the target molecule, said method comprising:
  (a) providing a probe comprising
    (i) a first target-binding site at a 3' end region of said probe, which binding site is capable of hybridising to a complementary binding site in the target molecule, said complementary binding site being a 3' flanking sequence flanking the 3' end of the ROI, and is capable of being extended to generate a complement of the target molecule in a target-templated extension reaction, said target complement comprising the complement of said 3' flanking sequence and the ROI; and
    (ii) a second binding site which is homologous to the ROI, or to the 5' end thereof, and is capable of hybridising to a complement of the ROI, or of the 5' end thereof, in said target complement;
    (iii) a further probe sequence, lying 3' of the second binding site, which is homologous to the 3' flanking sequence and complementary to the first binding site;
  wherein said probe is provided as an oligonucleotide comprising a stem-loop structure which comprises the second binding site and the further probe sequence in the loop of the structure and further comprises a cleavage site 3' of the second binding site and further probe sequence, which is cleavable to open the loop to render the second binding site and further probe sequence available for binding, and a single-stranded region at the 3' end of the probe comprising the first binding site at the 3' end thereof; or
  wherein said probe is provided as a partially double-stranded construct comprising a first strand comprising a single-stranded 3' end region comprising the first binding site at the 3' end thereof and a second strand hybridised at the 5' end of said first strand and comprising a single-stranded 3' end region comprising the second binding site and the further probe sequence at the 3' end of the single-stranded region;
  (b) contacting the probe with the target molecule and allowing the first target-binding site at the 3' end of the probe to hybridise to its complementary binding site in the target molecule, wherein the target molecule is at least partially single stranded including in the region comprising the complementary binding site, and optionally the ROI;
  (c) extending the hybridised 3' end of the probe using the target molecule as an extension template to generate a complement of the target molecule;
  (d) removing the target molecule, leaving an extended probe comprising 3' to 5' in the extended region a complement of the ROI, and the 3' flanking sequence of the target molecule, wherein the second binding site remains in the probe;
  (e) allowing the extended probe to undergo an intramolecular rearrangement such that the second binding site hybridises to its complementary binding site in the target complement, being the complement of the ROI, or of the 5' end of the ROI, and the further probe sequence hybridises to the first binding site,
  wherein if said probe comprises a stem-loop structure the rearrangement comprises cleavage of the extended probe at the cleavage site in the stem-loop structure of the probe to release a 3' end of the probe comprising the second binding site and the further probe sequence, thereby generating a partially double-stranded construct comprising a first extended strand comprising the target complement and a released 5' end, and a second strand hybridised to the first strand in the stem and comprising the released 3' end which is then able to hybridise to its complementary binding sites in the first strand,
  such that the, optionally released, 5' end of the first, extended, strand and the 3' end of the first, extended, strand are brought into juxtaposition for ligation directly or indirectly to each other, using the second binding site and further probe sequence as ligation template;
  (f) ligating the ends of the extended strand of the probe directly or indirectly to one another to circularise the extended strand of the probe;
  (g) amplifying or separating the circularised extended strand, thereby to select the ROI.

In a particular aspect, the second binding site is homologous to the 5' end of the ROI, and is capable of hybridising to a complement of the 5' end of the ROI.

Also provided is a probe for use in the methods of the present invention, said probe comprising:
  (i) a first target-binding site at a 3' end region of said probe, which binding site is capable of hybridising to a complementary binding site in the target molecule, said complementary binding site being a 3' flanking sequence flanking the 3' end of the ROI, and is capable of being extended to generate a complement of the target molecule in a target-templated extension reaction, said target complement comprising the complement of said 3' flanking sequence and the ROI; and
  (ii) a second binding site which is homologous to the ROI, or to the 5' end thereof, and is capable of hybridising to a complement of the ROI, or of the 5' end thereof, in said target complement;

(iii) a further probe sequence, lying 3' of the second binding site, which is homologous to the 3' flanking sequence and complementary to the first binding site.

In one aspect, the probe may be provided as an oligonucleotide comprising a stem-loop structure which comprises the second binding site and the further probe sequence in the loop of the structure and further comprises a cleavage site 3' of the second binding site and further probe sequence, which is cleavable to open the loop to render the second binding site and further probe sequence available for binding, and a single-stranded region at the 3' end of the probe comprising the first binding site at the 3' end thereof.

In a further aspect, the probe may be provided as a partially double-stranded construct comprising a first strand comprising a single-stranded 3' end region comprising the first binding site at the 3' end thereof and a second strand hybridised at the 5' end of said first strand and comprising a single-stranded 3' end region comprising the second binding site and the further probe sequence at the 3' end of the single-stranded region.

The circularised target fragment complement which is selected according to the method of the invention, or an amplicon thereof, may be detected. The detection may be by nucleic acid readout platform, including sequencing or any sequence-analysis procedure, real-time PCR and sRCA. A selected and amplified target ROI can be detected or analysed using a number of known means, e.g. by hybridisation of a detection probe to the amplified product which may be labelled, or which may take part in further signal-giving or signal-amplification reaction, e.g. a ligation-based reaction, e.g. a padlock probe, or a probe for an OLA assay. Padlock probes may be detected in further amplification reactions, e.g. in a sRCA reaction.

Thus the amplified products of an amplification reaction may be detected using any convenient protocol, which may detect the amplification products non-specifically or specifically, as described in greater detail below. Representative non-specific detection protocols of interest include protocols that employ signal producing systems that selectively detect double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating $Tb^{3+}$ and $Eu^{3+}$, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR Green, EvaGreen, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

In yet other embodiments, a signal producing system that is specific for the amplification product, as opposed to double stranded molecules in general, may be employed to detect the amplification. In these embodiments, the signal producing system may include a detection probe that specifically binds to a sequence found in the amplification product, where the detection probe may be labelled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3-CTP, Cy5-CTP) etc. Fluorescent moieties which may be used to tag nucleotides for producing labelled probes include, but are not limited to: fluorescein, the cyanine dyes, such as Cy3, Cy5, Alexa 555, Bodipy 630/650, and the like. Other labels, such as those described above, may also be employed as are known in the art.

In certain embodiments, the specifically labelled detection probes are labelled with "energy transfer" labels. As used herein, "energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer, or through direct energy transfer. The exact energy transfer mechanisms in these two cases are different. It is to be understood that any reference to energy transfer in the instant application encompasses all of these mechanistically-distinct phenomena. As used herein, "energy transfer pair" refers to any two molecules that participate in energy transfer. Typically, one of the molecules acts as a fluorescent group, and the other acts as a fluorescence-modifying group. "Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another. As used herein, "fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength, or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group, or can do so only poorly. As used herein "direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others' electronic structure. If the fluorescence-modifying group is a quenching group, this will result in the quenching group preventing the fluorescent group from even emitting light.

The energy transfer labelled detection probe, e.g. oligonucleotide, may be structured in a variety of different ways, so long as it includes a donor, acceptor and target nucleic acid binding domains. As such, the energy transfer labelled oligonucleotides employed in these embodiments of the method are nucleic acid detectors that include a fluorophore domain where the fluorescent energy donor, i.e., donor, is positioned and an acceptor domain where the fluorescent energy acceptor, i.e., acceptor, is positioned. As mentioned above, the donor domain includes the donor fluorophore. The donor fluorophore may be positioned anywhere in the nucleic acid detector, but is typically present at the 5' terminus of the detector. The acceptor domain includes the fluorescence energy acceptor. The acceptor may be positioned anywhere in the acceptor domain, but is typically present at the 3' terminus of the nucleic acid detector or probe.

In addition to the fluorophore and acceptor domains, the energy transfer labelled probe oligonucleotides also include a target nucleic acid binding domain, which binds to a target nucleic acid sequence (e.g. a tag, for example a barcode sequence) found in the amplification product of interest (as described above). Specific examples of such labelled oligonucleotide probes include the Tag Man® type probes, as described in U.S. Pat. No. 6,248,526, the disclosure of which is herein incorporated by reference (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). Examples of other types of probe structures include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117,635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes.

The next step in the subject methods is signal detection from the labelled amplification products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the target ROI (or more particularly the complement of the ROI). Depending on the particular label employed, detection of a signal may indicate the presence or absence of the target ROI.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter, or where the sample is a tissue sample on a microscope slide, fluorescence may be detected using a fluorescence microscope. Fluorescence is suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time. Thus, in some embodiments multiple targets may be detected in parallel, whereas in other embodiments multiple targets may be detected sequentially.

Where the detection protocol is a real time protocol, e.g., as employed in real time PCR reaction protocols, data may be collected in this way at frequent intervals, for example once every 3 minutes, throughout the reaction. By monitoring the fluorescence of the reactive molecule from the sample during each cycle, the progress of the amplification reaction can be monitored in various ways. For example, the data provided by melting peaks can be analysed, for example by calculating the area under the melting peaks and these data plotted against the number of cycles.

The spectra generated in this way can be resolved, for example, using "fits" of pre-selected fluorescent moieties such as dyes, to form peaks representative of each signalling moiety (i.e. fluorophore). The areas under the peaks can be determined which represents the intensity value for each signal, and if required, expressed as quotients of each other. The differential of signal intensities and/or ratios will allow changes in labelled probes to be recorded through the reaction or at different reaction conditions, such as temperatures. The changes are related to the binding phenomenon between the detection probe and the target sequence or degradation of the detection probe bound to the target sequence. The integral of the area under the differential peaks will allow intensity values for the label effects to be calculated.

Screening the mixture for a change in fluorescence provides one or more assay results, depending on whether the sample is screened once at the end of the primer extension reaction, or multiple times, e.g., after each cycle, of an amplification reaction (e.g., as is done in real time PCR monitoring).

The data generated as described above can be interpreted in various ways. In its simplest form, an increase or decrease in fluorescence from the sample in the course of or at the end of the amplification reaction is indicative of an increase in the amount of the target present in the sample, e.g., as correlated to the amount of amplification product detected in the reaction mixture, suggestive of the fact that the amplification reaction has proceeded and therefore the target was in fact present in the initial sample. Quantification is also possible by monitoring the amplification reaction throughout the amplification process. Quantification may also include assaying for one or more nucleic acid controls in the reaction mixture, as described above.

The method of the invention may have a number of uses and applications. One such use may be the preparation of substrates or templates for sequencing or other sequence analysis. As discussed above, the method may also be used for detection, e.g. for identification of a target ROI or for detection of the presence or absence, or amount or level, of a particular target ROI in a given sample. Thus the method may be used for the detection of a target organism, e.g. a pathogen in a sample, which may be useful clinically or for research or other purposes, e.g. epidemiological studies or for studying microbial resistance etc. Further the method may find utility in screening for or detecting rare mutations, e.g. when screening for minimal residual disease in cancer (e.g. in circulating tumour cells), particularly when combined with sensitive detection strategies such as sRCA.

As discussed above, the method of the invention has a number of advantages, including for use in such applications. For instance it does not require the correct 5' and 3' ends of a probe to be present in order for selection to take place, provided that the first target binding region is capable of binding to its complementary sequence. N-1 and N-2 deletions are commonly present in synthesised nucleic acids, particularly when longer oligonucleotides are used. For circularisation it is also required that the 5' end of the oligonucleotide to be circularised is phosphorylated. 5' phosphorylation of probes is a technical hurdle and expensive if large numbers of probes are used. Synthesised nucleic acid probes can often lack a phosphate group at their 5' end, which can prevent ligation and circularisation of a target nucleic acid molecule once it has been selected, for example in the context of a Selector probe. The present invention therefore bypasses both of these obstacles to the selection of target nucleic acid sequences, reducing the cost associated with ensuring that highly homogeneous phosphorylated nucleic acid probes are used.

Advantageously, the present invention can as mentioned above be in homogenous (non-solid phase) or in solid phase-based formats. A selected target nucleic acid can therefore be identified either in situ or in an array-based assay using any one of a number of techniques known in the art. Use of a solid phase may enable or facilitate washing steps to be included.

The probes, and optionally other components for performing the method of the invention may conveniently be provided in kit form.

Accordingly, in a further aspect the invention provides a kit, more particularly a kit for selecting a target ROI in a target nucleic acid molecule, said kit comprising:

(a) a probe of the invention as hereinbefore defined; and optionally one or more further components selected from:

(b) means for cleaving the cleavage site within the stem-loop structure of the probe, e.g. one or more restriction enzymes or nickase enzymes;

(c) means for cleaving the second cleavage site, if present, e.g. one or more cleavage enzymes as discussed above;

(d) means for degrading the 3' end of the extended probe when the 5' flanking sequence is internal to the 5' end of the target molecule, e.g. a 3'→5' exonuclease enzyme;

(e) means for extending the probe, e.g. a polymerase, which may have strand displacement activity;

(f) a ligase enzyme;

(g) one or more gap oligonucleotides;

(h) means for amplification of the circularised extended strand comprising the complement of the target fragment, e.g. one or more amplification primers, (e.g. PCR primers) and/or amplification enzymes (e.g. a polymerase, for example phi29 or another strand displacing polymerase for RCA, or a polymerase suitable for PCR, as known in the art);

(i) means for detecting the circularised extended strand (comprising the target fragment complement) or an amplicon thereof, e.g. one or more detection probes, or labels, or means for a further detection reaction, e.g. means for performing a sRCA reaction, for example a primer for the sRCA reaction, a template for the sRCA reaction or a padlock probe etc. as described above.

The kit components may be present in separate containers, or one or more of the components may be present in the same container, where the containers may be storage containers and/or containers that are employed during the assay for which the kit is designed.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, flash drive, etc., on which the information has been recorded. Yet another means that may be present is a website address which may be used via the internet to access the information at a removed site. Any convenient means may be present in the kits.

Figure 1B:
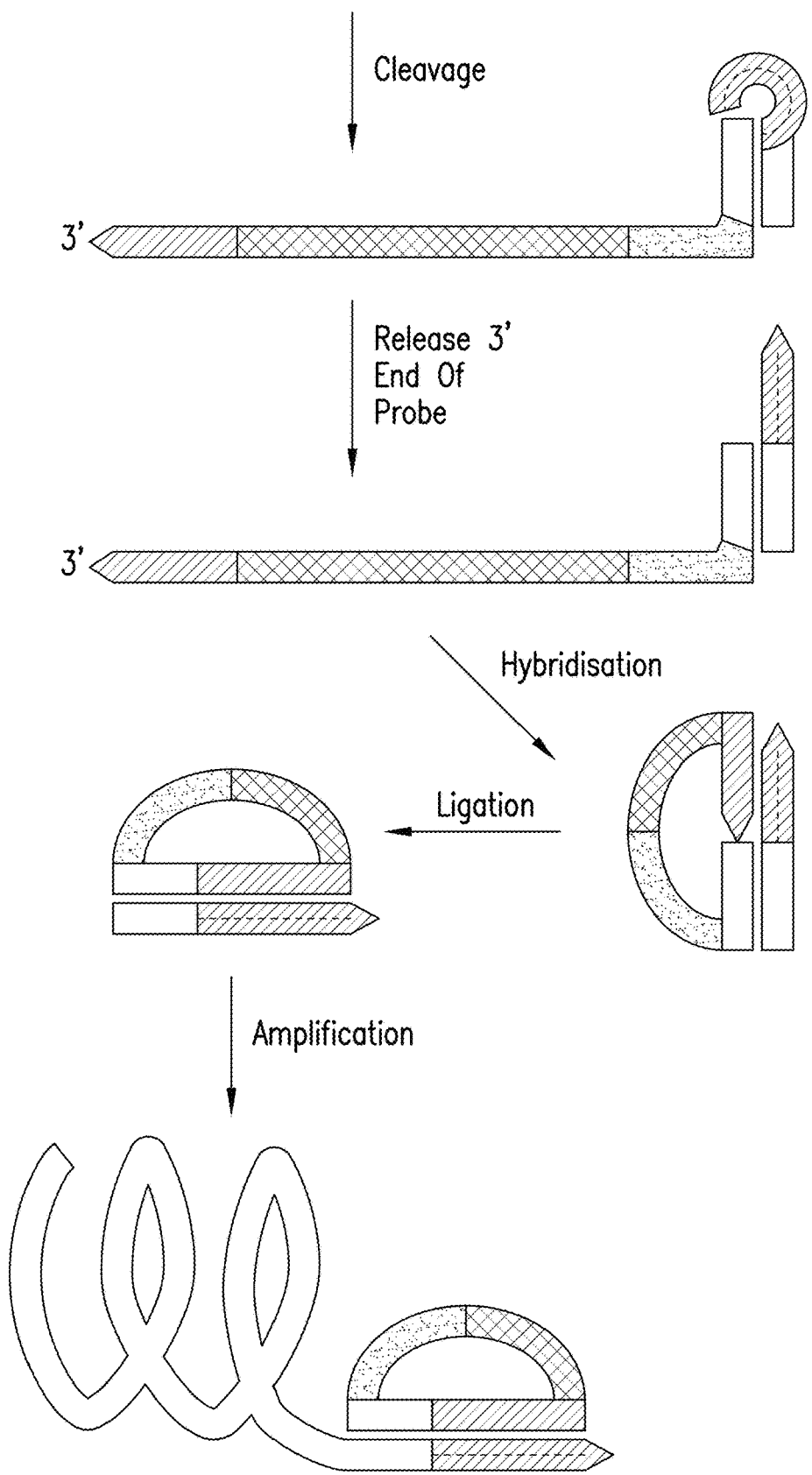

The invention will be further described in the following non-limiting Examples with reference to the drawings in which:

FIGS. 1A and 1B illustrate the method of the invention for a target nucleic acid molecule where the 5' flanking sequence flanking the target ROI is at the end of the target molecule. The probe of the invention binds to the 3' flanking sequence flanking the target ROI, and is extended to generate a complement of the target molecule. The target molecule is then removed. Cleavage of the stem or loop of the stem-loop structure releases the 3' end of the probe comprising the second binding site, and allows it to hybridise to its complementary binding site in the extended strand. The ends of the extended strand are then ligated, and the circularised extended strand may be amplified or separated. Dotted lines indicate sequences with the same orientation (5'→3') as the target ROI.

Figure 2A:
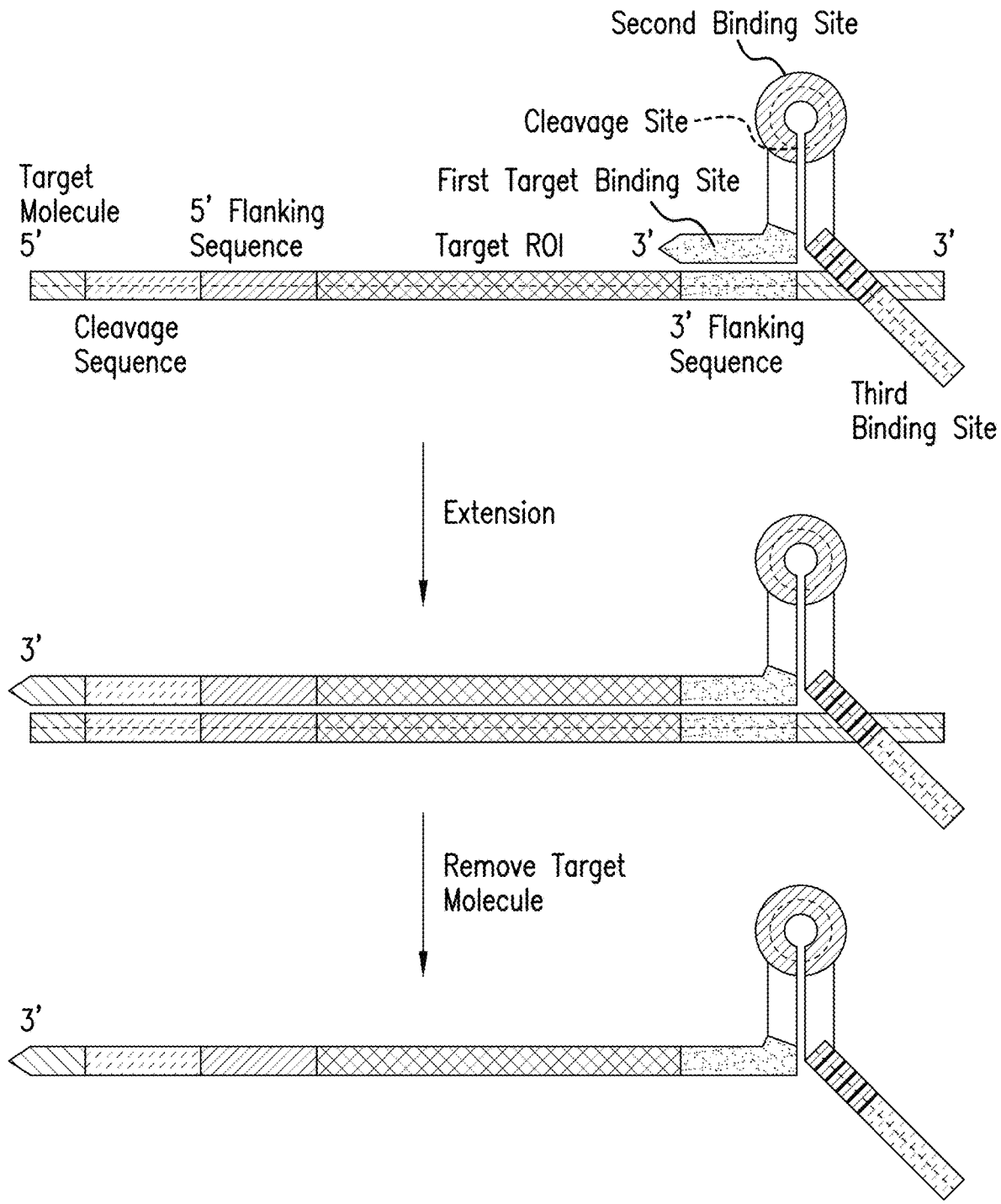
Figure 2B:
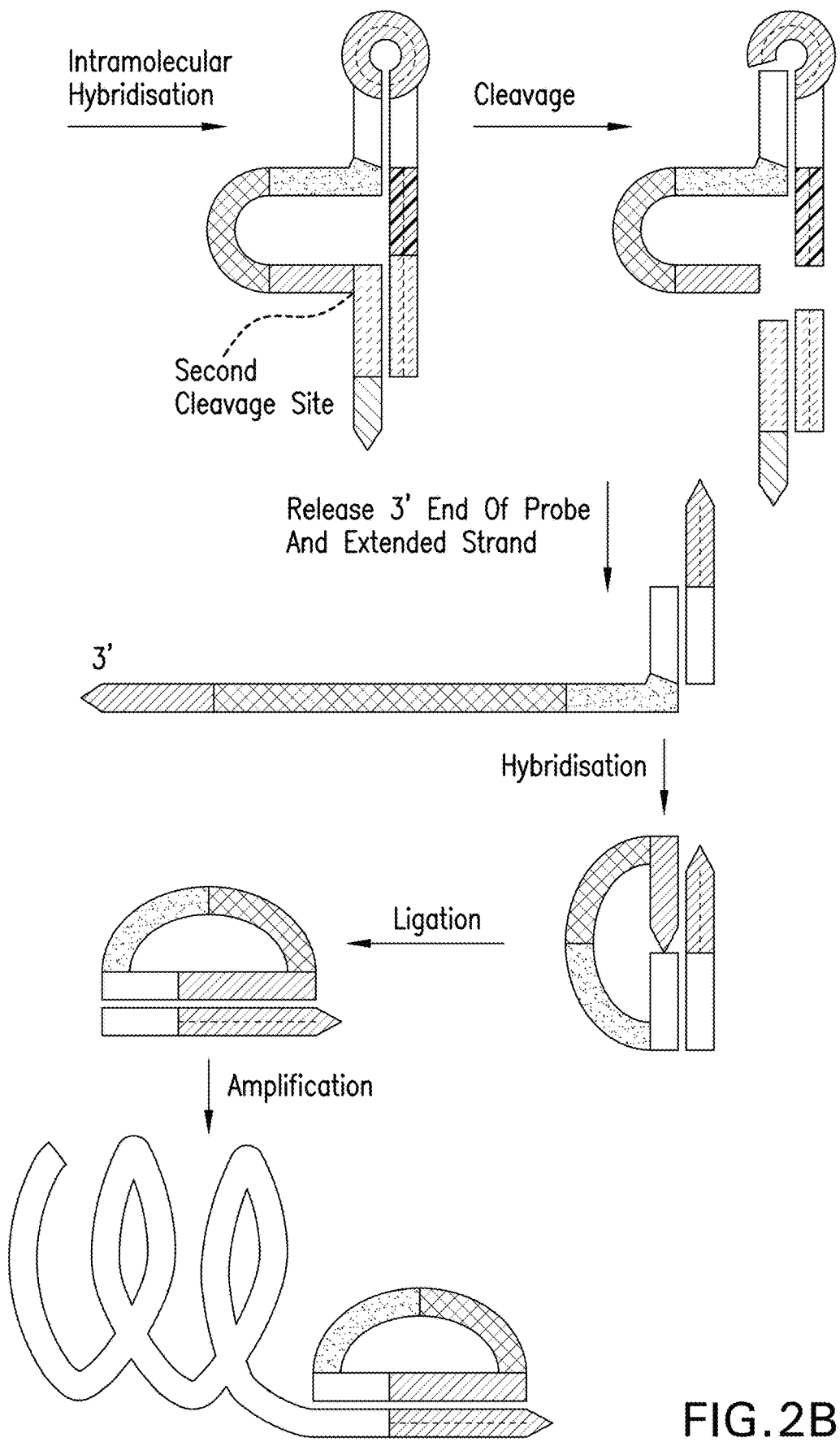

FIGS. 2A and 2B illustrate the method of the invention for a target nucleic acid molecule where the 5' flanking sequence flanking the target ROI is internal to the 5' end of the target molecule. The probe may comprise a third binding site which is homologous to a cleavage sequence immediately 5' to the 5' flanking sequence. The complement of the 5' flanking region is capable of hybridising to the third binding site, generating a second cleavage site. Cleavage of the hybridised probe at the second cleavage site and at the cleavage site in the stem or loop of the stem-loop structure releases the 3' end of the extended strand, which can be circularised as outlined in FIGS. 1A and 1B. Dotted lines indicate sequences with the same orientation (5'→3') as the target ROI.

Figure 3:
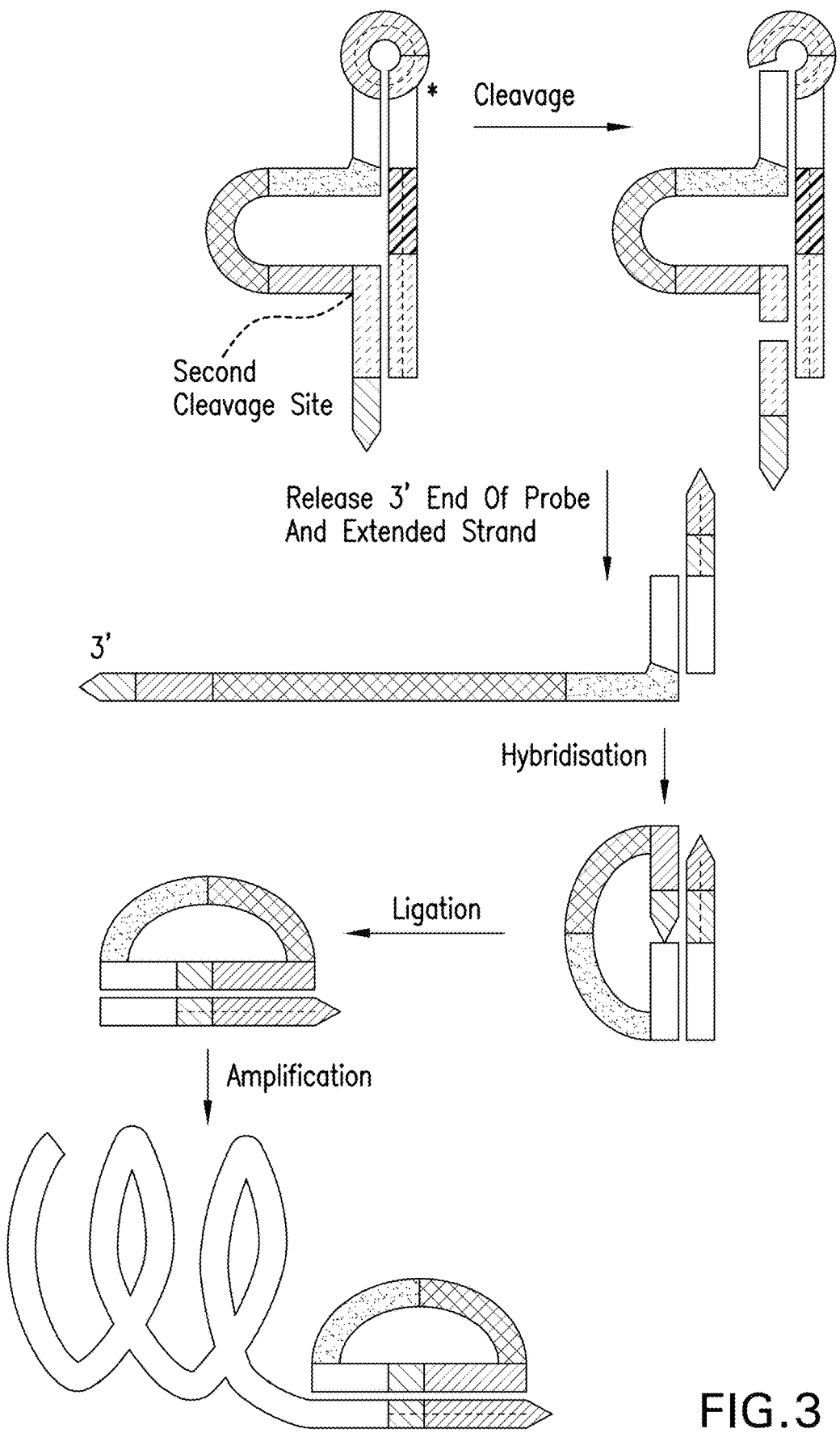

FIG. 3 illustrates the method of the invention wherein the second cleavage site is not situated at the 3' end of the third binding site, and a portion of sequence remains at the 3' end of the first strand following cleavage. The probe comprises 5' to the second binding site a sequence complementary to a sequence in the target complement that is complementary to the third binding site (marked with a *). Cleavage of the second cleavage site and stem or loop occurs as illustrated in FIG. 2. Dotted lines indicate sequences with the same orientation (5'→3') as the target ROI.

FIG. 4 illustrates the method of the invention wherein the probe comprises a fourth target binding sequence 5' of the stem-loop structure, which is complementary to the region immediately 3' of the 3' flanking sequence flanking the target ROI.

Figure 5A:
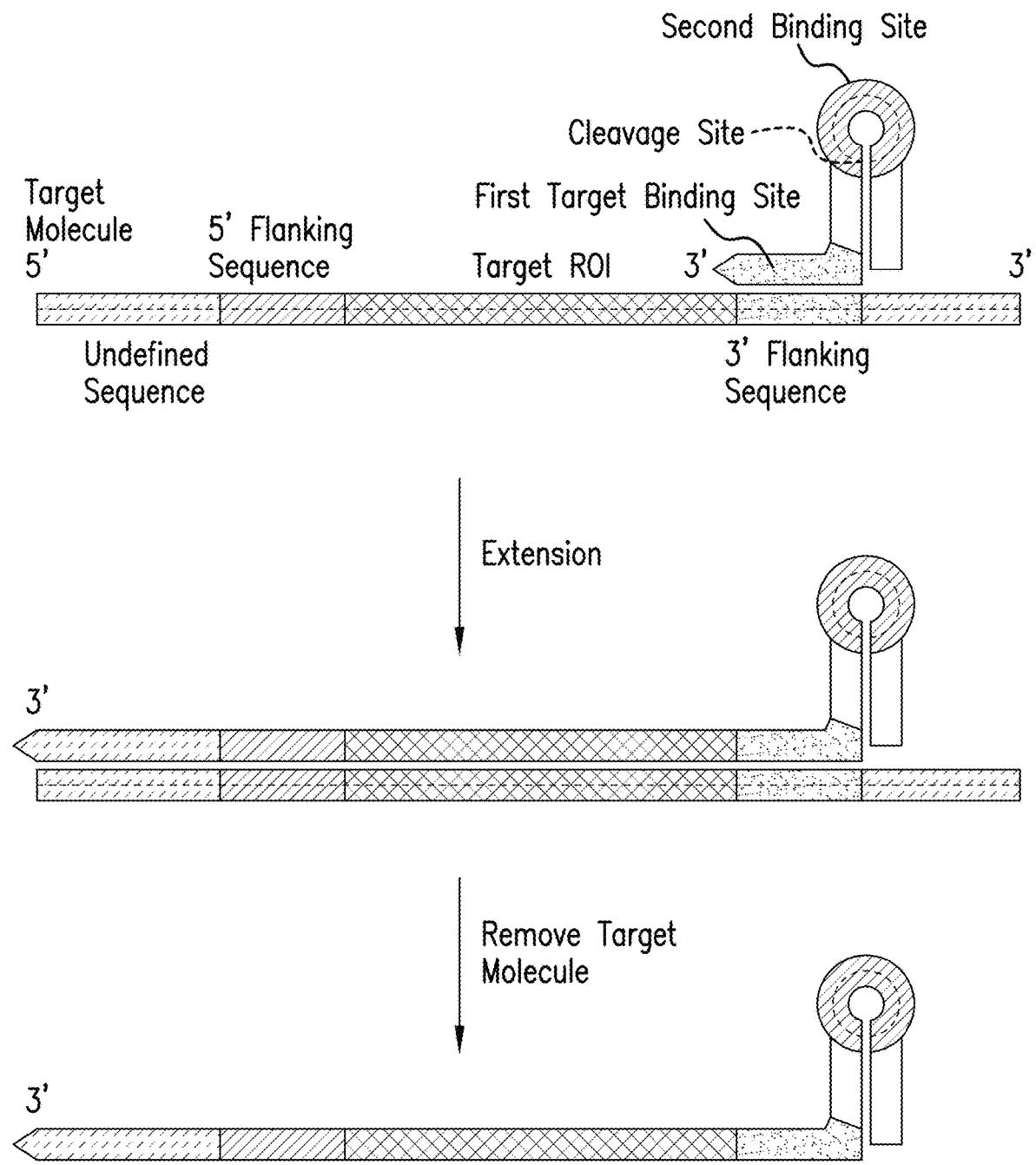
Figure 5B:
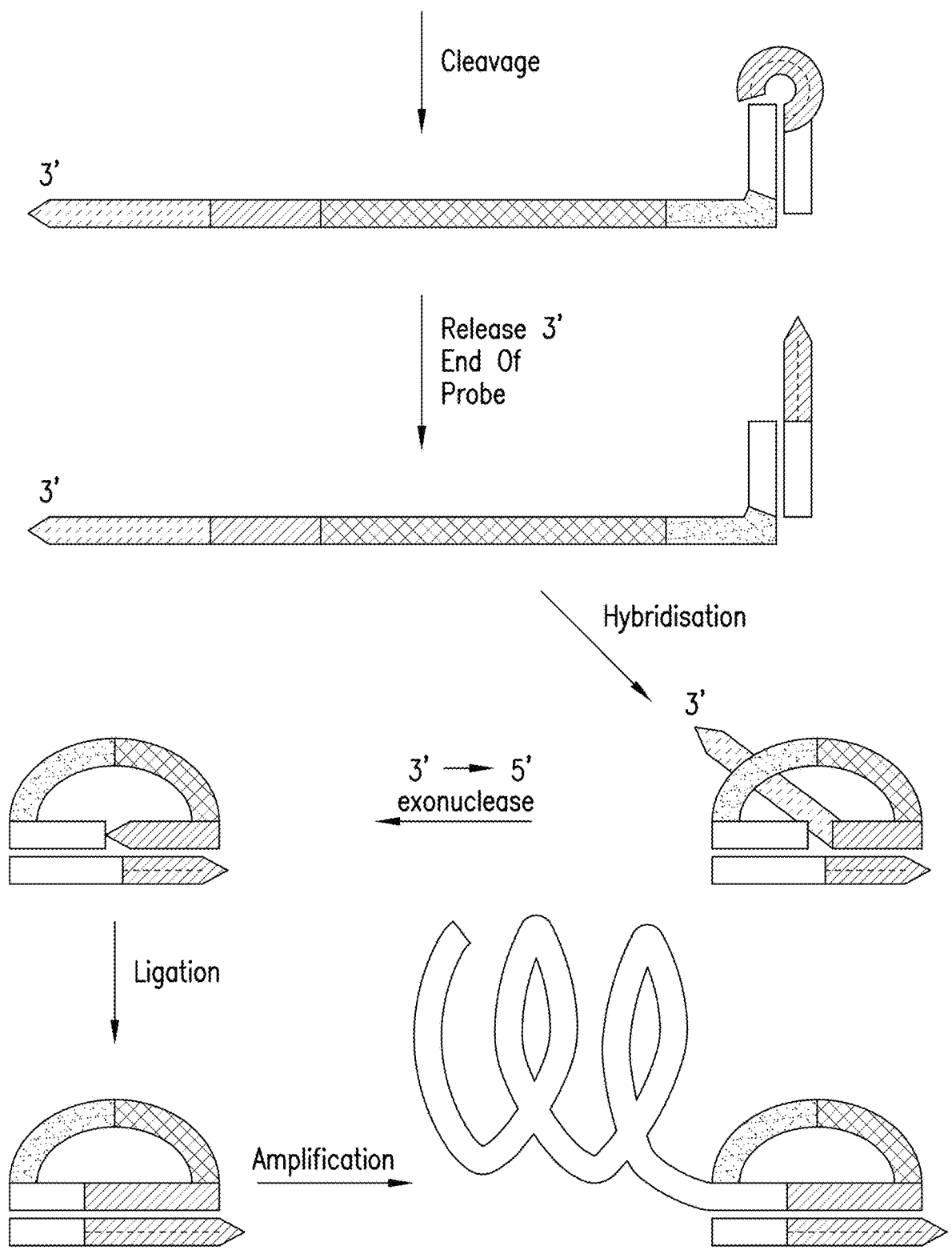

FIGS. 5A and 5B illustrate the method of the invention for a target nucleic acid molecule wherein the 5' flanking sequence flanking the target ROI is internal to the 5' end of the target molecule, and the probe does not comprise a third binding site. Cleavage of the stem or loop in the stem-loop structure takes place as illustrated in FIGS. 1A and 1B, and the complement of the 5' flanking sequence hybridises to the second binding site, forming a circular structure with a protruding 3' overhang. The overhang can be digested by any enzyme with 3'→5' exonuclease activity. Dotted lines indicate sequences with the same orientation (5'→3') as the target ROI.

Figure 6A:
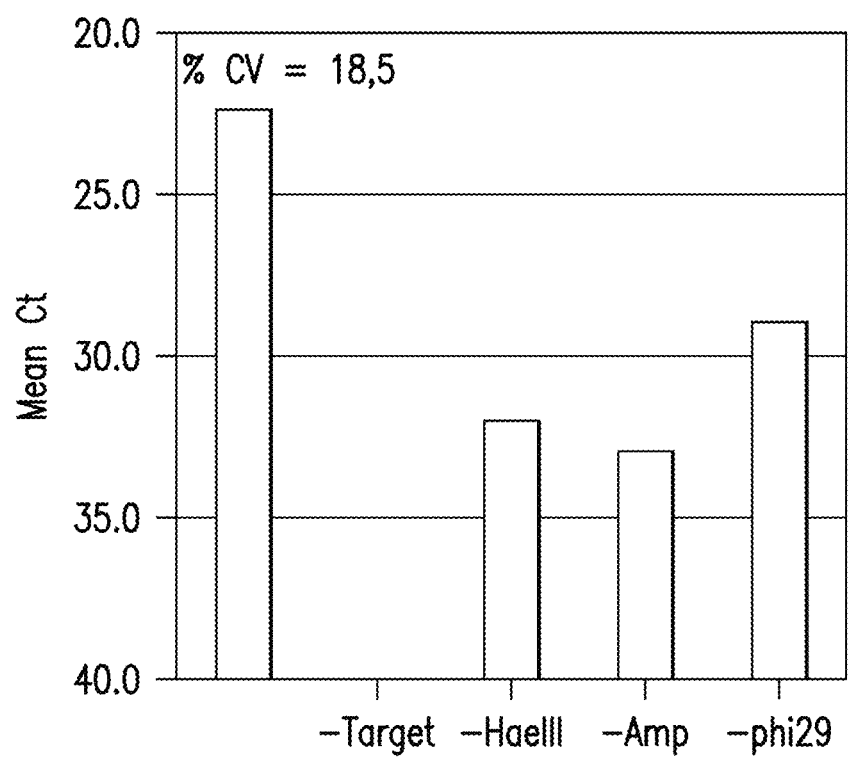
Figure 6B:
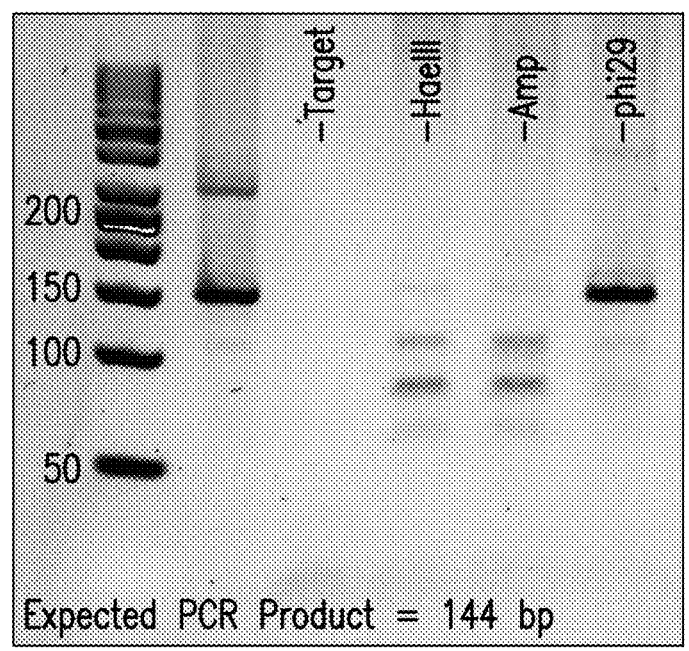

FIGS. 6A and 6B show the results of detecting genomic DNA by the method of the present invention, using probes with a restriction enzyme cleavage site within the loop of the stem-loop structure. FIG. 6A: Positive signals were observed only when targets, restriction enzymes and ligase were present. Decrease of signals from reactions without RCA amplification (−phi29) in comparison to reactions with RCA amplification indicates successful circularization of extended probes after enzymatic cleavage followed by RCA. CV ~18.5% was calculated for duplicate measurements. FIG 6B: PCR products were validated by 4% agarose gel.

Figure 7A:
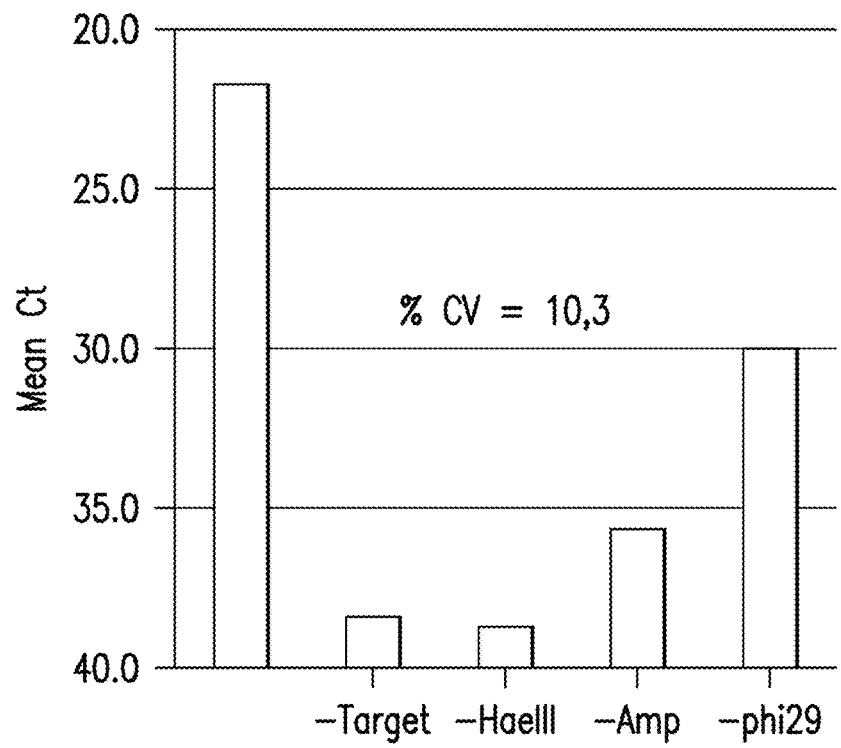
Figure 7B:
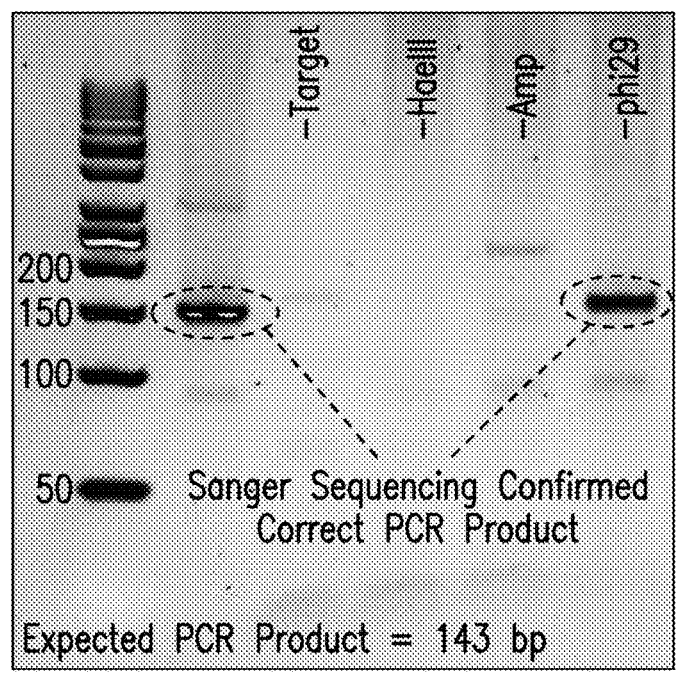

FIGS. 7A-7C show the results of detecting genomic DNA by the method of the present invention, using probes with a nickase cleavage site within the stem of the stem-loop structure. FIG. 7A: Positive signals were observed only when targets, restriction enzymes and ligase were present. Decrease of signals from reactions without RCA amplification (−phi29) in comparison to reactions with RCA amplification indicates successful circularization of extended probes after enzymatic cleavage followed by RCA. CV ~10.3% was calculated for duplicate measurements. PCR products were validated by 4% agarose gel (FIG. 7B) and Sanger sequencing (FIG. 7C).

Figure 8A:
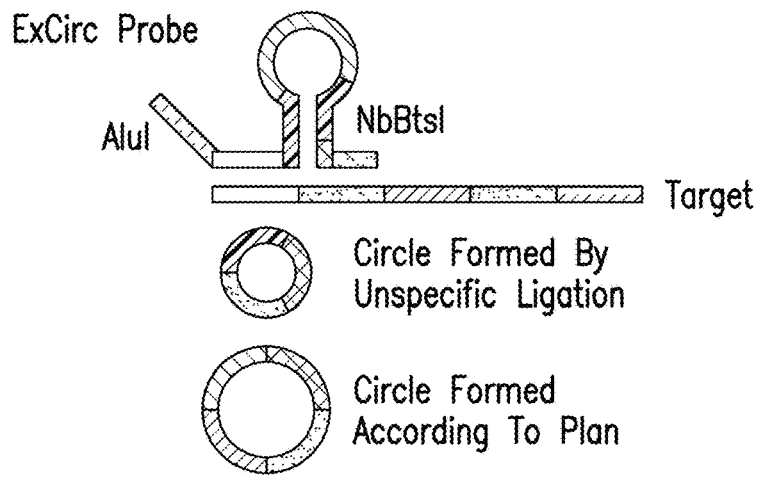
Figure 8B:
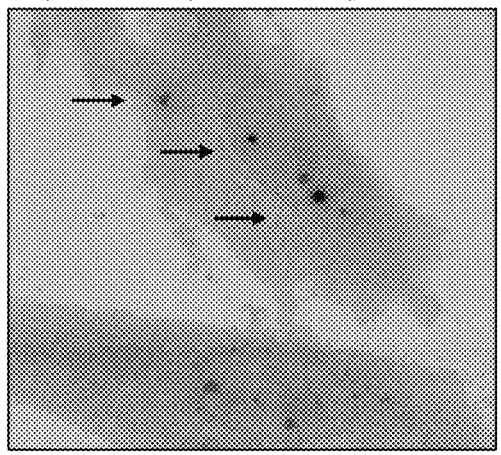
Figure 8B:
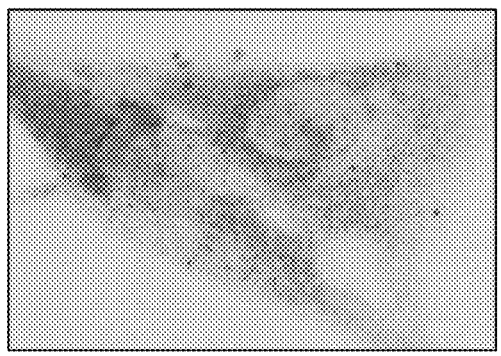
Figure 8B:
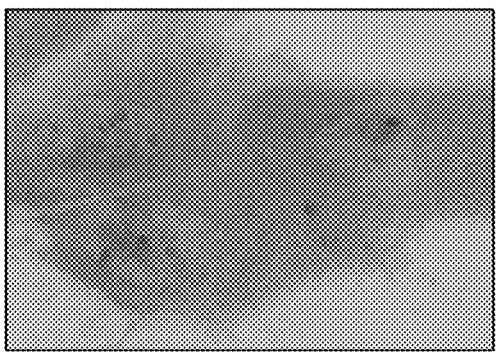

FIGS. 8A and 8B show the results of detecting hTERT mRNA in situ by the method of the present invention. FIG. 8A shows RCA products were labelled with two different fluorophores; one was designed specifically for labelling correctly selected target fragment, and the other was designed for labelling embedded sequences in probes. Correct signals were expected to contain both colours and FIG. 8B shows that correct signals were observed only when all enzymes were present.

Figure 9:
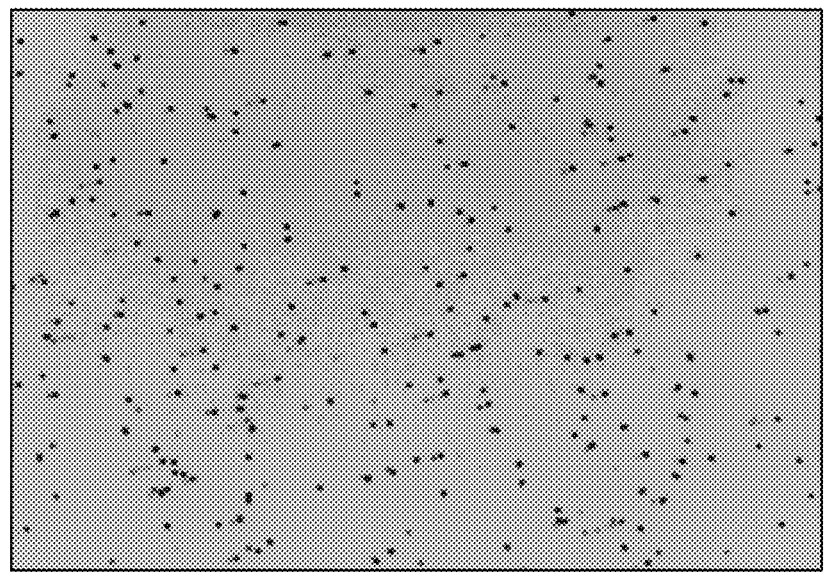
Figure 9:
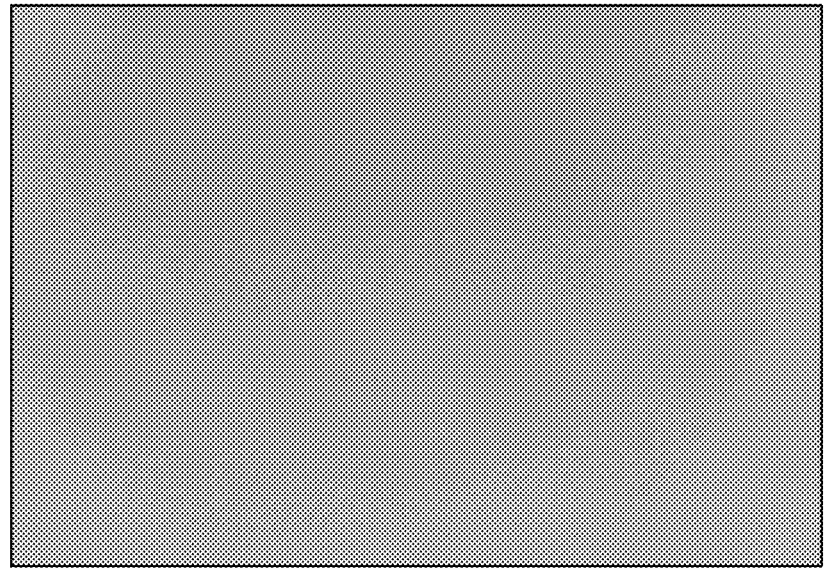

FIG. 9 shows the results of detecting microRNA by the method of the present invention using a probe immobilised on a solid support by its 5' end. Positive signals were observed only when targets were present.

FIG. 10 illustrates a method of the invention in which the probe comprises the third binding site in the loop of the stem loop structure, between the second binding site and the cleavage site in the stem-loop structure. Thus the third binding site is 5' of the cleavage site in the stem-loop structure. The third binding site templates the cleavage of the excess sequence 3' to the target complement, releasing the 3' end of the target complement for ligation.

FIG. 11 illustrates a method of the invention for a target nucleic acid molecule where the 5' flanking sequence flanking the target ROI is internal to the 5' end of the target molecule. The probe comprises at its 5' end a biotin moiety, which may be used to selectively remove uncleaved probes from the sample, and an additional sequence 3' to the cleavage site which may be used to immobilise the cleaved and extended probe (e.g. for in situ detection).

FIG. 12 illustrates the method of the invention of FIG. 11, wherein the probe comprising in the loop of the stem loop structure a further hairpin structure which may be cleaved by a restriction enzyme, in this case Mlyl.

FIG. 13 illustrates a method of the invention in which the probe comprises in its loop a further probe sequence, being homologous to the 3' flanking region of the target nucleic acid molecule (and being complementary to the first binding site. The probe further comprises (5' to the further binding site) a second binding site which is homologous to the ROI. Together, the second binding site and the further probe sequence are able to hybridise to the complement of the target nucleic acid molecule (i.e. complement of the 3' flanking region and the complement of the ROI) to template the circularisation of the first, extended, strand of the probe.

EXAMPLE 1—DETECTION OF GENOMIC DNA

A target ROI within a portion of genomic DNA was detected using the method of the present invention. The target nucleic acid molecule comprised a Haelll cleavage site 5' of the 5' flanking sequence flanking the target ROI, and detection was performed using probe comprising a third binding site homologous to this region. Probes with a restriction enzyme cleavage site (ExCirc_1) and a nickase cleavage site (ExCirc_2) in the stem-loop structure were used to select the target ROI. The sequences of the probes used to detect the KRAS target region of interest are shown in Table 1. The stem of the stem-loop structure is shown in italics. The ExCirc_1 probe was designed to bind to a portion of the KRAS_1 target sequence, and the ExCirc_2 probe was designed to bind to a portion of the KRAS_2 target sequence. Target sequences are shown in Table 2. Approximately 1e5 human genomes (Promega) and 100 nM of probes of the invention were mixed in 20 µl of extension mix consisting of 1× EINAR buffer (50 mM KAc, 20 mM Tris-HAc pH 7.6, 3 mM MgAC$_2$), 0.06 U/µl Platinum Taq DNA polymerase (Invitrogen), 0.2 mM d(A, T, G, C)TP (Thermo Scientific). The extension was carried out at 95° C. for 5 min and 60° C. for 1 min. 1 µl of Proteinase K (Thermo Scientific) was added in each reaction, followed by incubation at 37° C. for 30 min and 95° C. for 20 min. ExCirc_1 (comprising a restriction enzyme cleavage site) and ExCirc_2 (comprising a nickase cleavage site) are defined in Table 1. Cleavage sites within the probe are indicated in bold.

TABLE 1

List of probes used to select KRAS target ROI.

| SEQ ID NO: | Probe name | Cleavage sites | Sequence |
|---|---|---|---|
| 1 | ExCirc_1 | MlyI, HaeIII | CATTATTTTTATTATAAGGCCTGGCGCAT GCGTCCTCCTGCTGAAAATGACTGGGGGG ACTCGAAAACGAGTCCCCCCAGGACGCAT GCGCCCTCTATTGTTGGATCATATTCGTC CAC |
| 2 | ExCirc_2 | Nb. BtsI, HaeIII | GTCACATTTTCATTATTTTTATTATAAGG CCTGCGTGCTTGTGCAGTGCCTGCTGAAA ATGACCAGGCACTGCACAAGCACGGAA TTGTTGGATCATATTCGTCCA |

TABLE 2

List of KRAS target sequences.

| SEQ ID NO: | Target | Target sequence |
|---|---|---|
| 3 | KRAS_1 | CATTATTTTTATTATAAGGCCTGCTGAAAATGACTGAAT ATAAACTTGTGGTAGTTGGAGCTGGTGGCGTAGGCAAGA GTGCCTTGACGATACAGCTAATTCAGAATCATTTTGTGG ACGAATATGATCCAACAATAGAG |
| 4 | KRAS_2 | GTCACATTTTCATTATTTTTATTATAAGGCCTGCTGAAA ATGACTGAATATAAACTTGTGGTAGTTGGAGCTGGTGGC GTAGGCAAGAGTGCCTTGACGATACAGCTAATTCAGAAT CATTTTGTGGACGAATATGATCCAACAATAGAG |

For the ExCirc_1 probe, 5 µl of cutting and ligation mix consisting of 1× EINAR buffer, 1 U/µl of each restriction enzyme (HaeIII (NEB) and MlyI (NEB)), 2.5 mM NAD (Sigma-Aldrich), 0.1 U/µl Ampligase (Epicenter Biotechnology) were added to each extension reaction, followed by incubation at 37° C. for 30 min and 55° C. for 20 min.

For the ExCirc_2 probe, 5 µl of cutting mix consisting of 1× EINAR buffer, 1 U/µl HaeIII and 1 UM Nb.BtsI (NEB) were added to each extension reaction, followed by incubation at 37° C. for 30 min and 85° C. for 20 min.

5 µl of ligation mix consisting of 1× EINAR buffer, 3 mM NAD, 0.12 U/µl ampligase were added to each of the cutting products, followed by incubation at 55° C. for 15 min. After circularization, 10 µl RCA mix consisting of 1× EINAR buffer, 0.4 µg/µl BSA (NEB), 0.5 mM d(A, T, G, C)TP, 0.04 U/µl phi29 DNA polymerase (Thermo Scientific) were added to 10 µl of ligation products, followed by incubation at 37° C. for 60 min and 65° C. for 15 min. After RCA, 10 µl of PCR mix consisting of 1× EINAR buffer, 200 nM CLR_Kras forward and reverse primers (see Table 3), 1×SYBR (Molecular probes), 0.12 U/µl Platinum Taq DNA polymerase, 0.4 mM d(A, U, G, C)TP (Thermo Scientific), 0.004 U/µl UNG (Thermo Scientific) were added to 10 µl of RCA products. Real time PCR was carried out in Stratagene MX3005 PCR machine (Agilent Technologies) using a thermal profile with an initiation at 95° C. for 2 min followed by 45 cycles of 95° C. for 15 sec and 60° C. for 1 min.

TABLE 3

List of PCR primers used to detect KRAS target ROI.

| SEQ ID NO: | Primer name | Sequence |
|---|---|---|
| 5 | CLR_KRAS_1 | CGTGCCTTGACGATACAGCTAA |
| 6 | CLR_KRAS_2 | CAAGGCACTCTTGCCTACG |

The results of the detection of genomic DNA using probes comprising restriction enzyme and nickase cleavage sites within the loop of the stem-loop structure are shown in FIGS. 6 and 7, respectively. Part (A) of both figures shows that a positive signal is only detected when the target nucleic acid and first and second cleavage enzymes are used in the detection method. Part (B) of both figures indicates that the target ROI was selected in both cases, and that selection did not take place when the target nucleic acid molecule, HaeIII or ampligase (DNA ligase) was absent. FIG. 7 part (C) indicates that the correct sequence was selected, and was detectable either with or without rolling circle amplification of the circularised extended strand.

EXAMPLE 2—DETECTION OF IN SITU MRNA

BJhTERT Cells were grown on Superfrost Plus Gold slides (Thermo Scientific) and fixed in 3% (w/v) paraformaldehyde (Sigma-Aldrich) in 1× PBS at room temperature for 30 min. After fixation, cells were washed twice in DEPC-treated 1× PBS and dehydrated with ethanol series. After being air-dried, the slides were stored at −80° C. Prior to probing, secure-Seal™ Spacers (d=8 mm) (Life Technologies) were used for creating 50 µl reaction chambers on the slides. Throughout the protocol, two washes with DEPC-treated 1× PBS, 0.05% Tween-20 were carried out between each incubation and addition of new reaction mix. First, cells were incubated with blocking buffer consisting of 2×SSC, 1 U/µl RiboLock RNase Inhibitor (Thermo Scientific), 1 µg/µl BSA, 1 µg/µl Salmon sperm DNA (Invitrogen), 1 µg/µl E. coli tRNA (Sigma-Aldrich) at 37° C. for 1 h.

50 µl of 100 nM of the ExCirc_hTERT probe in blocking buffer was added to the cells, followed by incubation at 37° C. for 1 h. This probe comprised a fourth binding site 5' of the stem-loop structure. The sequence of the probe used is shown in Table 4—cleavage sites are indicated in bold. The stem of the stem-loop structure is shown in italics. The sequence of the hTERT target sequence is shown in Table 5. Next, 50 µl of extension mix consisting of 1× RT buffer (Thermo Scientific), 0.2 µg/µl BSA (NEB), 0.5 mM d(A, T, G, C)TP (Thermo Scientific), 10 U/µl RevertAid H Minus Reverse Transcriptase (Thermo Scientific), 1 U/µl RiboLock RNase Inhibitor were added to cells, followed by incubation at 55° C. for 60 min.

TABLE 4

Sequence of probe used to detect hTERT mRNA.

| SEQ ID NO: | Probe name | Cleavage sites | Sequence |
|---|---|---|---|
| 7 | ExCirc_hTERT | Nb. BtsI, AluI | TACGGCGACATGGAGAACAAGCTGTTTTTTT TTTTTTTTTTTTTTTT*CGTGCTTGTGCAGTG CTGTTTGCGGGGATTACAG*CACTGCACAA GCACGGAAGAGTGAATGCGAGTCCGTCTCAA CAAGAAATCATCCACCAAACGCAGGAG |

TABLE 5

Sequence of hTERT target sequence.

| SEQ ID NO: | Target | Target sequence |
|---|---|---|
| 8 | hTERT | TACGGCGACATGGAGAACAAGCTGTTTGCGGGA TTCGGCGGGACGGGCTGCTCCTGCGTTTGGTGGA TGAT |

After a post fixation with 3.7% (w/v) paraformaldehyde at room temperature for 5 min, 50 µl of cutting mix consisting of 1× CutSmart buffer (NEB), 0.5 U/µl Nb.BtsI, 0.1 U/µl RNaseH (Thermo Scientific), 0.5 U/µl AluI and 1 U/µl RiboLock RNase Inhibitor were added to the cells, followed by incubation at 37° C. for 30 min. After cutting, 50 µl of ligation mix consisting of 1× CutSmart buffer, 0.3 U/µl T4 DNA ligase and 0.5 mM ATP was added to the cells, followed by incubation at 37° C. for 30 min. Next, 50 µl of RCA mix consisting of 1× phi29 buffer (Thermo Scientific), 0.2 µg/µl BSA, 0.25 mM d(A, T, G, C)TP, 2.5% glycerol (Sigma-Aldrich) and 0.5 U/µl phi29 DNA polymerase was added to the cells, followed by incubation at 37° C. for 60 min.

The RCA products were visualized by incubation with 50 µl detection mix containing 100 nM detection oligonucleotides in 2× SSC, 20% Formamide (Sigma-Aldrich) at 37° C. for 20 min. The slides were mounted with anti-fade medium containing 100 ng/ml DAPI (Olink) and imaged using 40× oil objective of an Axioplan II epifluorescence microscope (Zeiss) with excitation and emission filters for Cy3 and Cy5 with exposure time of 2000 ms and 8000 ms, respectively. Detection oligonucleotides were designed to detect a specific sequence within the target ROI (ExCirc_hTERT_Detection1) (see Table 5, underlined sequence) or a sequence element introduced into the probe (ExCirc_hTERT_Detection2) (see Table 4, underlined sequence), and are shown in Table 6.

TABLE 6

Detection oligonucleotides used to detect hTERT target ROI.

| SEQ ID NO: | Oligonucleotide name | Sequence |
|---|---|---|
| 9 | ExCirc_hTERT_Detection1 | Cy3-CAGCCCGTCCCGCCG |
| 10 | ExCirc_hTERT_Detection2 | Cy5-TGCGAGTCCGTCTUUU |

Non-specific ligation of the probe resulted in the formation of a circular nucleic acid molecule comprising the sequence element introduced into the probe, but not the target ROI, and the amplification product was only detected in the Cy5 channel. Specific ligation (i.e. according to the method of the invention) resulted in the formation and amplification of a circular nucleic acid molecule comprising both the sequence element introduced into the probe, and the target ROI sequence. The amplification product was detected in both the Cy3 and Cy5 channels (see FIG. 8).

EXAMPLE 3—DETECTION OF SYNTHETIC MICRORNA 1 pM 50 µl of a 5' biotinylated probe of the invention (ExCirc_miR208b, see Table 7) was immobilized on a streptavidin-coated Codelink slide (SurModics) in 1× PBS at 37° C. for 60 min. The stem of the stem-loop structure is shown in italics. Secure-Seal™ Spacer (d=8 mm) was used for creating 50 µl reaction chambers on the slides. Throughout the protocol, two washes with 1× PBS, 0.05% Tween20 were carried out between each incubation and addition of new reaction mix.

TABLE 7

Sequence of probe used to detect miRNA.

| SEQ ID NO: | Probe name | Cleavage site | Sequence |
|---|---|---|---|
| 11 | ExCirc_miR208b | Nb.BtsI | TTTTTTTTTTTTTTTTTTTTCTCTCTCT CAGCTCACTGGCAGTGATAAGACGAATTA *TCACTGC*CAGTGAGCTAGACTTATTGC GGAGTGAATGCGAGTCCGTCTACAAACCT TTTG |

100 nM of synthetic microRNA (Synthetic_RNA_miR208b—see Table 8) were applied to the slides and incubated at 37° C. for 60 min to allow hybridisation. Next, 50 µl of extension mix consisting of 1× RT buffer, 0.2 µg/µl BSA, 0.5 mM d(A, T, G, C)TP, 10 U/µl RevertAid H Minus Reverse Transcriptase were added to the slides, followed by incubation at 37° C. for 30 min.

TABLE 8 miRNA detected in the method of the present invention.

| SEQ ID NO: | miRNA name | Sequence |
|---|---|---|
| 12 | Synthetic_RNA_miR208b | AUAAGACGAACAAAAGGUUUGU |

50 µl of cutting mix consisting of 1× NEBuffer 4 (NEB), 0.5 µg/µl BSA, 0.5 U/µl Nb.BtsI were added to the slides, followed by incubation at 37° C. for 30 min. 50 µl of ligation mix consisting of 1× NEBuffer 4, 0.5 µg/µl BSA, 0.3 U/µl T4 DNA ligase, 0.5 U/µl RNaseH, 0.5 mM ATP were added to the slides, followed by incubation at 37° C. for 30 min. Next, 50 µl of RCA mix consisting of 1× phi29 buffer, 0.25 mM d(A, T, G, C)TP and 0.5 U/µl phi29 DNA polymerase were added to the slides, followed by incubation at 37° C. for 30 min.

The RCA products were visualized by incubation with 50 µl detection mix containing 100 nM detection oligonucleotides (ExCirc_miR208b_Detection—see Table 9) in 2× SSC, 20% formamide at 37° C. for 20 min. The slides were mounted with anti-fade medium (Olink) and imaged using 20× objective of an Axioplan II epifluorescence microscope (Zeiss) with excitation and emission filters for Cy3 with exposure time of 800 ms.

TABLE 9

Detection oligonucleotide used to detect miR208 miRNA.

| SEQ ID NO: | Oligonucleotide name | Sequence |
|---|---|---|
| 13 | ExCirc_miR208b_Detection | Cy3-CAGTGAATGCGAGTCCGTCT |

Amplification products were only detected on slides where target miRNA had been added to the immobilised oligonucleotide (see FIG. 9).

The invention claimed is:

1. A method of selecting a target region of interest (ROI) in a target nucleic acid molecule, said ROI being flanked by a 3' flanking sequence and a 5' flanking sequence in the target molecule, said method comprising:
   (a) providing a probe comprising
      (i) a first target-binding site at a 3' end region of said probe, which target-binding site is capable of hybridising to a complementary binding site in the target molecule, said complementary binding site being the 3' flanking sequence flanking the 3' end of the ROI, and is capable of being extended to generate a complement of the target molecule in a target-templated extension reaction, said target complement comprising the complement of said 3' flanking sequence and at least of the ROI and the 5' flanking sequence; and
      (ii) a second binding site which is homologous to the 5' flanking sequence flanking the 5' end of the ROI and is capable of hybridising to a complement of said 5' flanking sequence in said target complement;
   wherein said probe is provided as an oligonucleotide comprising a stem-loop structure which comprises the second binding site in the loop of the structure and further comprises a cleavage site 3' of the second binding site which is cleavable to open the loop, and a single-stranded region at the 3' end comprising the first binding site; or
   wherein said probe is provided as a partially double-stranded construct comprising a first strand comprising a single-stranded 3' end region comprising the first binding site at the 3' end of the first strand, and a second strand hybridised at the 5' end of said first strand and comprising a single-stranded 3' end region comprising the second binding site;
   (b) contacting the probe with the target molecule and allowing the first target-binding site to hybridise to its complementary binding site in the target molecule, wherein the target molecule is at least partially single stranded including in the region comprising the complementary binding site, and optionally the ROI and the 5' flanking sequence;
   (c) extending the hybridised 3' end of the probe using the target molecule as an extension template to generate a complement of the target molecule;
   (d) removing the target molecule, leaving an extended probe comprising 3' to 5' in the extended region complements of the 5' flanking sequence, the ROI and the 3' flanking sequence of the target molecule, wherein the second binding site remains in the probe;
   (e) allowing the extended probe to undergo an intramolecular rearrangement such that the second binding site hybridises to its complementary binding site in the target complement, being the complement of the 5' flanking sequence of the target molecule,
   wherein if said probe comprises a stem-loop structure, the rearrangement comprises cleavage of the extended probe at the cleavage site in the stem-loop structure of the probe to release a 3' end of the probe comprising the second binding site thereby generating a partially double-stranded construct comprising a first extended strand comprising the target complement and a second strand hybridised to the first strand in the stem and comprising the released 3' end which is then able to hybridise to its complementary binding site in the first strand, and
   wherein if said 5' flanking sequence is internal to the 5' end of the target molecule and the target complement in the first extended strand contains an additional sequence 3' of the complement of the 5' flanking sequence, the rearrangement comprises a cleavage in or of the additional sequence to release the 3' end of the first strand comprising the complementary binding site for the second binding site, such that the, optionally released, 5' end of the first, extended, strand and the, optionally released, 3' end of the first, extended, strand are brought into juxtaposition for ligation directly or indirectly to each other, using the second binding site as ligation template;
(f) ligating the ends of the extended strand of the probe directly or indirectly to one another to circularise the extended strand of the probe;
(g) amplifying or separating the circularised extended strand, thereby to select the ROI.

2. The method of claim 1, being a method of selecting a target ROI in a target nucleic acid molecule, said method comprising;
(a) providing a probe comprising a stem-loop structure and a single-stranded region at the 3' end, wherein said 3' end region comprises a first target-binding site which is capable of hybridising to a complementary binding site in the target molecule, said complementary binding site being a flanking sequence flanking the 3' end of the ROI, and said loop comprises a second binding site which is homologous to a flanking sequence flanking the 5' end of the ROI and is capable of hybridising to a complement of said 5' flanking sequence, and wherein said stem-loop structure further comprises a cleavage site 3' of said second binding site such that cleavage allows the loop to open;
(b) contacting the probe with the target molecule and allowing the first target-binding site at the 3' end of the probe to hybridise to its complementary binding site in the target molecule, wherein the target molecule is at least partially single stranded including in the region comprising the complementary binding site, and optionally the ROI and the 5' flanking sequence;
(c) extending the hybridised 3' end of the probe using the target molecule as an extension template to generate a complement of the target molecule;
(d) removing the target molecule, leaving an extended probe comprising 3' to 5' in the extended region complements of the 5' flanking sequence and the ROI, and the 3' flanking sequence of the target molecule;
(e) allowing the second binding site to hybridise to its complementary binding site in the target complement, being the complement of the 5' flanking sequence of the target molecule, wherein the rearrangement comprises cleavage of the extended probe at least at the cleavage site in the stem-loop structure of the probe to release a 3' end of the probe comprising the second binding site, thereby generating a partially double-stranded construct comprising a first extended strand comprising the target complement and a released 5' end, and a second strand hybridised to the first strand in the stem and comprising the released 3' end which hybridises to its complementary binding site in the first strand, and if said 5' flanking sequence is internal to the 5' end of the target molecule and the target complement in the first extended strand contains an additional sequence 3' of the complement of the 5' flanking sequence, also a second cleavage in or of the additional sequence to release the 3' end of the first strand comprising the complementary binding site for the second binding site, such that the released 5' end of the first, extended, strand and the optionally released 3' end of the first, extended, strand are brought into juxtaposition for ligation directly or indirectly to each other, using the second binding site as ligation template;
(f) ligating the ends of the extended strand of the probe directly or indirectly to one another to circularise the extended strand of the probe;
(g) amplifying or separating the circularised extended strand, thereby to select the ROI.

3. The method of claim 2, wherein
(A) the 5' flanking sequence lies at the 5' end of the target nucleic acid molecule and step (e) comprises
(i) cleaving the extended probe at the cleavage site in the stem-loop structure of the probe to release a 3' end of the probe comprising the second binding site, thereby generating a partially double-stranded construct comprising a first extended strand comprising the target complement and a second strand hybridised to the first strand in the stem and comprising the released 3' end; and
(ii) allowing the second binding site in the released 3' end in the second strand to hybridise to its complementary binding site in the target complement in the first strand, thereby to bring the 5' and 3' ends of the first, extended, strand into juxtaposition for ligation, directly or indirectly, to each other, using the second binding site as ligation template; or
(B) the 5' flanking sequence is internal to the 5' end of the target nucleic acid molecule, and the probe further comprises a single-stranded region at the 5' end comprising a third binding site which is homologous to a cleavage sequence immediately 5' to the 5' flanking sequence in the target molecule and is capable of hybridising to a complement of said cleavage sequence, wherein said third binding site is optionally separated from the 5' end of the stem by a spacer sequence and wherein step (e) comprises:
(i) allowing the extended probe to undergo an intramolecular hybridisation wherein the third binding site hybridises to its complementary binding site in the target complement, thereby generating a second cleavage site;
(ii) cleaving the hybridised probe at the second cleavage site and at the cleavage site in the stem-loop structure, thereby generating a partially double stranded construct comprising two strands hybridised at the stem, the first strand comprising the target complement and the second strand comprising the second binding site; and
(iii) allowing the second binding site to hybridise to its complementary binding site in the target complement in the first strand, thereby bringing the 5' and 3' ends of the first, extended, strand into juxtaposition for ligation directly or indirectly to each other, using the second binding site as ligation template.

4. The method of claim 3, wherein the 5' flanking sequence is internal to the target nucleic acid molecule, and wherein the loop in the probe further comprises 5' to the second binding site a sequence complementary to a sequence from the complementary binding site in the target complement for the third binding site, which sequence remains at the 3' end of the first strand of the probe following cleavage at the second cleavage site, and/or wherein the spacer sequence comprises a fourth target binding site which is capable of hybridising to a complementary binding site in the target molecule lying 3' of the 3' flanking sequence of the target molecule, and wherein step (b) further comprises allowing the fourth target binding site to hybridise to its complementary binding site in the target molecule.

5. The method of claim 3 wherein the 5' flanking sequence lies at the 5' end of the target nucleic acid molecule and the target molecule is a micro RNA or a RNA transcript.

6. The method of claim 2, wherein the 5' flanking sequence is internal to the 5' end of the target nucleic acid molecule, wherein
  (A) the probe further comprises within the stem-loop structure a third binding site which is homologous to a cleavage sequence immediately 5' to the 5' flanking sequence in the target molecule and which is capable of hybridising to a complement of said cleavage sequence, wherein said third binding site is 3' to the second binding site and wherein step (e) comprises:
    (i) allowing the extended probe to undergo an intramolecular hybridisation wherein the third binding site hybridises to its complementary binding site in the target complement, thereby generating a second cleavage site;
    (ii) cleaving the hybridised probe at the second cleavage site and at the cleavage site in the stem-loop structure, thereby generating a partially double stranded construct comprising two strands hybridised at the stem, the first strand comprising the target complement and the second strand comprising the second binding site; and
    (iii) allowing the second binding site to hybridise to its complementary binding site in the target complement in the first strand, thereby bringing the 5' and 3' ends of the first, extended, strand into juxtaposition for ligation directly or indirectly to each other, using the second binding site as ligation template; or
  (B) step (e) comprises:
    (i) cleaving the extended probe at the cleavage site in the stem-loop structure of the probe to release a 3' end of the probe comprising the second binding site, thereby generating a partially double-stranded construct comprising a first extended strand comprising the target complement and a second strand hybridised to the first strand in the stem and comprising the released 3' end;
    (ii) allowing the second binding site in the released 3' end in the second strand to hybridise to its complementary binding site in the target complement in the first strand, wherein the additional sequence at the 3' end of the first strand does not hybridise and forms a protruding single stranded end; and
    (iii) cleaving the protruding single stranded end to leave a 3' end of the first strand which is hybridised to the second binding site in the second strand, thereby to bring the 5' and 3' ends of the first, extended, strand into juxtaposition for ligation, directly or indirectly, to each other, using the second binding site as ligation template.

7. The method of claim 1, being a method of selecting a target region of interest (ROI) in a target nucleic acid molecule, said method comprising;
  (a) providing a probe being a partially double-stranded construct having a first strand comprising single-stranded 3' end region comprising a first target-binding site at the 3' end thereof, wherein said first target binding site is capable of hybridising to a complementary binding site in the target molecule, said complementary binding site being a flanking sequence flanking the 3' end of the ROI, and a second strand hybridised to said first strand at the 5' end thereof and comprising a single-stranded 3' end region comprising a second binding site, wherein the second binding site is homologous to a flanking sequence flanking the 5' end of the ROI and is capable of hybridising to a complement of said 5' flanking sequence;
  (b) contacting the probe with the target molecule and allowing the first target-binding site at the 3' end of the first strand of the probe to hybridise to its complementary binding site in the target molecule, wherein the target molecule is at least partially single stranded including in the region comprising the complementary binding site, and optionally the ROI and the 5' flanking sequence;
  (c) extending the hybridised 3' end of the first strand of the probe using the target molecule as an extension template to generate a complement of the target molecule;
  (d) removing the target molecule without denaturing the probe, leaving an extended probe comprising 3' to 5' in the extended region complements of the 5' flanking sequence, the ROI and the 3' flanking sequence of the target molecule;
  (e) allowing the extended probe to undergo an intramolecular rearrangement such that the second binding site in the second strand is able to hybridise to its complementary binding site in the target complement in the extended first strand, being the complement of the 5' flanking sequence of the target molecule, wherein if said 5' flanking sequence is internal to the 5' end of the target molecule and the target complement in the first extended strand contains an additional sequence 3' of the complement of the 5' flanking sequence, the rearrangement comprises a cleavage in or of the additional sequence to release the 3' end of the first strand comprising the complementary binding site for the second binding site,
  such that the 5' end of the first, extended, strand and the optionally released 3' end of the first, extended, strand are brought into juxtaposition for ligation directly or indirectly to each other, using the second binding site as ligation template;
  (f) ligating the ends of the extended strand of the probe directly or indirectly to one another to circularise the extended strand of the probe;
  (g) amplifying or separating the circularised extended strand, thereby to select the ROI.

8. The method of claim 7, wherein:
  (A) the 5' flanking sequence lies at the 5' end of the target nucleic acid molecule and step (e) comprises:
  allowing the second binding site in the second strand to hybridise to its complementary binding site in the target complement in the extended first strand, thereby to bring the 5' and 3' ends of the first, extended, strand into juxtaposition for ligation, directly or indirectly to each other, using the second binding site as ligation template; or
  (B) the 5' flanking sequence is internal to the 5' end of the target nucleic acid molecule, and the second strand of the probe further comprises a third binding site which is homologous to a cleavage sequence immediately 5' to the 5' flanking sequence in the target molecule and is capable of hybridising to a complement of said cleavage sequence in the additional sequence in the target complement in the extended first strand which is 3' to the complement of the 5' flanking sequence, wherein said third binding site is located in the single-stranded 3' end region of the second strand 3' to the second binding site, or in a further single-stranded 5' end region of the second strand;

and wherein step (e) comprises:
(i) allowing the extended probe to undergo an intramolecular hybridisation wherein the third binding site hybridises to its complementary binding site in the target complement, thereby generating a cleavage site;
(ii) cleaving the hybridised probe at the cleavage site, thereby generating a released 3' end of the first extended strand; and
(iii) allowing the second binding site to hybridise to its complementary binding site in the target complement in the first strand, thereby bringing the 5' end and the released 3' end of the first, extended, strand into juxtaposition for ligation directly or indirectly to each other, using the second binding site as ligation template.

9. The method of claim 8, wherein the 5' flanking sequence lies at the 5' end of the target nucleic acid molecule and the target molecule is a micro RNA or an RNA transcript.

10. The method of claim 1, wherein the probe comprises a further probe sequence which lies 3' of the second binding site and is homologous to the 3' flanking sequence and complementary to the first target-binding site, wherein when said probe comprises a stem-loop structure said further probe sequence is located in the loop or when said probe is a double-stranded construct the further probe sequence is located at the 3' end of the second strand; and wherein in step (e) of said method the further probe sequence hybridises to the first target-binding site and acts as ligation template together with the second binding site.

11. The method of claim 1, wherein the 5' flanking sequence is internal to the 5' end of the target nucleic acid molecule and wherein the probe comprises an immobilisable affinity binding group or capture sequence element at the 5' end of a stem-loop probe or at the 5' end of the second strand of a partially-stranded probe, wherein said imobilisable group or sequence element is located at the 5' end of a 5' single-stranded region of the probe comprising a third binding site, and wherein said immobilisable group or sequence element is cleaved from extended probes upon cleavage at the cleavage site created by the third binding site allowing unreacted probes which have not been extended and cleaved at the third binding site and which retain the immobilisable group or sequence element to be removed or separated by virtue of the immobilisable group or sequence element.

12. The method of claim 1, wherein the probe comprises a stem loop structure and wherein the cleavage site is in the loop of the probe.

13. The method of claim 1, wherein the probe comprises a stem loop structure and wherein the cleavage site is in the stem of the probe.

14. The method of claim 1, wherein the stem or double-stranded region of the probe comprises one or more tag sequences.

15. The method of claim 1, wherein the target molecule is RNA and it is removed in step (d) by RNase digestion or alkaline hydrolysis.

16. The method of claim 1, wherein the probe comprises a stem loop structure and wherein the target molecule is removed in step (d) by denaturation.

17. The method of claim 1, wherein a plurality of probes are used to select a plurality of target regions of interest within the same target molecule derived from a variety of sources.

18. The method of claim 1, wherein a single probe is used to select a plurality of different target regions of interest within the same target molecule derived from a variety of sources.

19. The method of claim 1, wherein the probe further comprises one or more spacer sequences between the first target-binding site and the second binding site, or 5' of the second binding site.

20. The method of claim 19, wherein
a) the probe comprises a stem loop structure and one or more spacer sequences is located between the first target binding site and the stem-loop structure, within the stem-loop structure, 5' of the stem loop structure, in the stem and/or in the loop; or
b) the probe is a partially double-stranded structure and comprises one or more spacer sequences in the first strand between the first target binding site and the double-stranded region or 5' to the double-stranded region, or in the second strand 5' to the double-stranded region or 3' to the double-stranded region.

21. The method of claim 19, wherein the probe comprises a third binding site, and further comprises one or more spacer sequences 3' or 5' to said third binding site.

22. The method of claim 19, wherein
a) the probe comprises a stem loop structure and the one or more spacer sequences is located 3' of the stem of the stem-loop structure; or
b) the probe is a partially double-stranded structure and comprises one or more spacer sequences in the first strand 3' of the double-stranded region.

23. The method of claim 19, wherein the spacer sequence is a capture sequence.

24. The method of claim 23, wherein the capture sequence hybridises to a cognate complementary binding site provided on a solid surface.

25. The method of claim 23, wherein the capture sequence or a complementary oligonucleotide hybridised thereto is attached to an affinity binding moiety.

26. The method of claim 23, wherein
a) the probe comprises a stem loop structure and a capture sequence is provided 5' of the stem of the stem-loop structure; or
b) the probe is a partially double-stranded structure and comprises a capture sequence in the second strand 5' of the double-stranded region.

27. The method of claim 19, wherein the spacer sequence is or comprises a tag sequence or a complement thereof, wherein the tag sequence is selected from a detection sequence or an identification sequence element or a binding site for a primer or detection probe.

28. The method of claim 27, wherein the tag sequence is an identification element for the target ROI or a sample identification sequence.

29. The method of claim 19, wherein the probe comprises a stem loop structure and the spacer sequence is located within the loop of the stem-loop structure and is located 5' of the second binding site thereby creating a gap between the respective ends of the extended strand when they are both hybridised to the second binding site in step (e), and wherein the gap is filled prior to ligation by one or more gap oligonucleotides which hybridise in the gap between the ends of the extended strand, or by gap-fill extension of the 3' end of the hybridised extended strand using a polymerase, such that the extended strand and any gap oligonucleotides if present may be ligated into a circular molecule comprising the complement of the target fragment.

30. The method of claim 29, wherein the gap oligonucleotide(s) comprise(s) a tag sequence complementary to a tag sequence complement in the spacer sequence.

31. The method of claim 29, wherein the gap oligonucleotide comprises a region which is not complementary to the spacer sequence, and wherein the region of non-complementarity comprises a tag sequence.

32. The method of claim 29, wherein the gap oligonucleotide comprises a detection sequence or an identification sequence element, or a binding site for an amplification primer or a detection probe.

33. The method of claim 32, wherein the amplification primer is a universal amplification primer.

34. The method of claim 29, which is performed in multiplex using a plurality of different probes and wherein the gap oligonucleotide for each probe comprises the same tag sequence.

35. The method of claim 29, wherein the gap oligonucleotide is pre-hybridised to the probe prior to contacting the probe with the target nucleic acid molecule.

36. The method of claim 29, wherein the gap oligonucleotide is separately provided at the same time or after contacting the probe with the target molecule.

37. The method of claim 1, wherein the probe comprises a stem loop structure and the loop of the stem-loop structure comprises a region of intramolecular complementarity such that it is able to form a duplex within the loop.

38. The method of claim 1, wherein the cleavage is enzymatic cleavage.

39. The method of claim 38, wherein the enzymatic cleavage comprises a uracil-DNA glycosylase (UNG) enzyme in combination with an endonuclease enzyme capable of recognising apurinic/apyrimidinic sites of dsDNA.

40. The method of claim 39, wherein the endonuclease enzyme is capable of recognising apurinic/apyrimidinic sites of dsDNA is endonuclease IV.

41. The method of claim 1, wherein the cleavage site is recognized by a nickase or a restriction endonuclease.

42. The method of claim 41, wherein the nickase enzyme is removed from the assay or inactivated following cleavage.

43. The method of claim 1, wherein amplification of the circularised extended strand of the probe is by PCR or Rolling Circle Amplification (RCA).

44. The method of claim 43, wherein amplification is by RCA, and wherein amplification further comprises a second round of RCA.

45. The method of claim 1 further comprising a step of detecting the circularised extended strand or an amplicon thereof.

46. The method of claim 45, wherein the amplified product is detected by hybridising a detection probe labelled with a directly or indirectly detectable label to the amplification product.

47. The method of claim 46, wherein the detection label is a fluorescent label.

48. The method of claim 46, wherein the extended strand or amplicon thereof is detected by sequencing analysis.

49. A probe for use in the method of claim 1, said probe comprising a stem-loop structure and a single-stranded region at the 3' end, wherein said 3' end region comprises a first target-binding site which is capable of hybridising to a complementary binding site in the target molecule, said complementary binding site being a flanking sequence flanking the 3' end of the ROI, and said loop comprises a second binding site which is homologous to a flanking sequence flanking the 5' end of the ROI and is capable of hybridising to a complement of said 5' flanking sequence, and wherein said stem-loop structure further comprises a cleavage site 3' of said second binding site such that cleavage allows the loop to open.

50. A kit for selecting a target region of interest in a target nucleic acid molecule, said kit comprising:
 (a) a probe as defined in claim 49; and optionally one or more further components selected from:
 (b) means for cleaving the cleavage site within the stem-loop structure of the probe;
 (c) means for cleaving the second cleavage site;
 (d) means for degrading the 3' end of the extended probe, e.g. when the 5' flanking sequence is internal to the 5' end of the target molecule;
 (e) means for extending the probe, e.g. a polymerase enzyme;
 (f) a ligase enzyme;
 (g) one or more gap oligonucleotides;
 (h) means for amplification of the circularised extended strand;
 (i) means for detecting the circularised extended strand or an amplicon thereof.

51. A probe for use in the method of claim 1, said probe being a partially double-stranded construct having a first strand comprising single-stranded 3' end region comprising a first target-binding site at the 3' end thereof, wherein said first target binding site is capable of hybridising to a complementary binding site in the target molecule, said complementary binding site being a flanking sequence flanking the 3' end of the ROI, and a second strand hybridised to said first strand at the 5' end thereof and comprising a single-stranded 3' end region comprising a second binding site, wherein the second binding site is homologous to a flanking sequence flanking the 5' end of the ROI and is capable of hybridising to a complement of said 5' flanking sequence.

52. A kit for selecting a target region of interest in a target nucleic acid molecule, said kit comprising:
 (a) a probe as defined in claim 51; and optionally one or more further components selected from:
 (b) means for cleaving the cleavage site within the stem-loop structure of the probe;
 (c) means for cleaving the second cleavage site;
 (d) means for degrading the 3' end of the extended probe, e.g. when the 5' flanking sequence is internal to the 5' end of the target molecule;
 (e) means for extending the probe, e.g. a polymerase enzyme;
 (f) a ligase enzyme;
 (g) one or more gap oligonucleotides;
 (h) means for amplification of the circularised extended strand;
 (i) means for detecting the circularised extended strand or an amplicon thereof.

* * * * *

UNITED STATES PATENT AND TRADEMARK OFFICE
CERTIFICATE OF CORRECTION

| | | |
|---|---|---|
| PATENT NO. | : 11,352,658 B2 | |
| APPLICATION NO. | : 15/500418 | |
| DATED | : June 7, 2022 | |
| INVENTOR(S) | : Ulf Landegren et al. | |

It is certified that error appears in the above-identified patent and that said Letters Patent is hereby corrected as shown below:

On the Title Page

Item (30), change "1413718" to --1413718.6--.

In the Claims

Column 61, Line 60, change "binding" to --target-binding--.

Column 61, Line 64, change "binding" to --target-binding--.

Signed and Sealed this
Twenty-third Day of August, 2022

Katherine Kelly Vidal
Director of the United States Patent and Trademark Office